(12) United States Patent
Lively et al.

(10) Patent No.: US 7,157,585 B2
(45) Date of Patent: Jan. 2, 2007

(54) SERINE PROTEASE INHIBITORS

(75) Inventors: Sarah Elizabeth Lively, Congleton (GB); Bohdan Waszkowycz, Wilmslow (GB); Martin James Harrison, Didsbury (GB); Christopher Neil Farthing, Macclesfield (GB); Keith Michael Johnson, Cheadle Hulme (GB)

(73) Assignee: Tularik Limited, London (GB)

( * ) Notice: Subject to any disclaimer, the term of this patent is extended or adjusted under 35 U.S.C. 154(b) by 43 days.

(21) Appl. No.: 11/126,309

(22) Filed: May 11, 2005

(65) Prior Publication Data

US 2005/0215587 A1    Sep. 29, 2005

Related U.S. Application Data

(62) Division of application No. 10/148,174, filed as application No. PCT/GB00/04764 on Dec. 13, 2000, now Pat. No. 6,916,957.

(30) Foreign Application Priority Data

Dec. 14, 1999  (GB)  .................................. 9929552.9
Jun. 13, 2000  (WO)  ..................... PCT/GB00/02291

(51) Int. Cl.
  *C07D 277/62*   (2006.01)
  *A61K 31/425*   (2006.01)
  *C07C 233/64*   (2006.01)
  *A61K 31/16*    (2006.01)

(52) U.S. Cl. .................. 548/180; 548/181; 548/311.4; 548/490; 548/491; 548/531; 548/538; 546/112; 546/139; 546/189; 546/277.1; 549/69; 549/70; 544/358

(58) Field of Classification Search ........... 514/252.12, 514/299, 315, 330, 365, 385, 414, 415, 408, 514/419, 432, 448, 367, 423; 544/358; 546/139, 546/189, 112, 277.1; 548/490, 491, 492, 548/180, 531, 538, 181, 311.4; 549/69, 70
See application file for complete search history.

(56) References Cited

U.S. PATENT DOCUMENTS 6,262,069 B1   7/2001   Liebeschuetz et al.
6,740,682 B1   5/2004   Liebeschuetz

FOREIGN PATENT DOCUMENTS

| WO | WO98/47876 | 10/1998 |
| WO | WO99/11657 | 3/1999 |
| WO | WO99/11658 | 3/1999 |
| WO | WO99/55661 | 11/1999 |

*Primary Examiner*—Shailendra Kumar
(74) *Attorney, Agent, or Firm*—Martin A. Hay

(57) ABSTRACT

Compounds of formula (I)

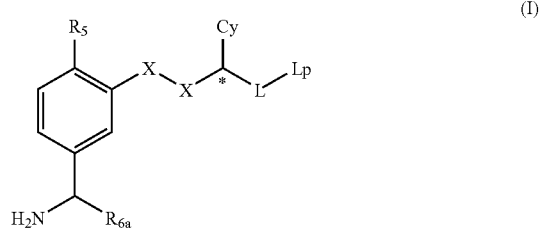

where $R_5$, $R_{6a}$, each X, L, Cy and Lp are as defined in the specification, are tryptase inhibitors useful as antiinflammatory agents.

27 Claims, No Drawings

SERINE PROTEASE INHIBITORS

This application is a divisional of application Ser. No. 10/148,174, now U.S. Pat. No. 6,916,957 which is a 371 of PCT/GB00/04764 filed Dec. 13, 2000.

This invention relates to compounds which are inhibitors of the serine protease, tryptase, to pharmaceutical compositions thereof and to their use in the treatment of the human or animal body. More particularly it relates to compounds for use in the treatment of mast cell mediated diseases such as asthma and other allergic and inflammatory conditions, to pharmaceutical compositions thereof and to their use in the treatment of the human or animal body.

Asthma, the most prevalent of all mast cell mediated conditions affects about 5% of the population in industrialised countries and there is evidence that its incidence and severity are on the increase. Furthermore, the incidence of childhood asthma is rising and there are suggestions of a link between environmental pollutants and the onset of the disease.

Initially, it was believed that bronchoconstriction, i.e. the narrowing of the airways in the lungs, was the major feature of asthma. However, it is now recognised that inflammation in the lungs is an integral part of the development of the disease.

The inhalation of an allergen by an asthmatic generates a strong immune system response which triggers release of various inflammatory mediators, including histamine and leukotrienes from inflammatory cells. These increase the permeability of the blood vessel walls, attract inflammatory cells into the tissues and contract the smooth muscle around the airways. As a result, fluid leaks from the blood and the tissues swell, further narrowing the airways. The inflammatory cells cause damage to the epithelial cells lining the airways exposing nerve endings which stimulates secretion of mucous as well as augmenting the inflammation by causing the release of neurokinins.

Thus asthma is a complex disease frequently characterised by progressive developments of hyper-responsiveness of the trachea and bronchi as a result of chronic inflammation reactions which irritate the epithelium lining the airway and cause pathological thickening of the underlying tissues.

Leukocytes and mast cells are present in the epithelium and smooth muscle tissue of the bronchi where they are activated-initially by binding of specific inhaled antigens to IgE receptors. Activated mast cells release a number of preformed or primary chemical mediators of the inflammatory response in asthma as well as enzymes. Moreover, secondary mediators of inflammation are generated by enzymatic reactions of activated mast cells and a number of large molecules are released by degranulation of mast cells.

It has therefore been proposed that chemical release from mast cells probably accounts for the early bronchiolar constriction response that occurs in susceptible individuals after exposure to airborne allergens. The early asthmatic reaction is maximal at around 15 minutes after allergen exposure, recovery occurring over the ensuing 1 to 2 hours. In approximately 30% of individuals, the early asthmatic reaction is followed by a further decline in respiratory function which normally begins within a few hours and is maximal between 6 and 12 hours after exposure. This late asthmatic reaction is accompanied by a marked increase in the number of inflammatory cells infiltrating bronchiolar smooth muscle and epithelial tissues, and spilling into the airways. These cells are attracted to the site by release of mast cell derived chemotactic agents.

The most straightforward way of dealing with an asthma attack is with a bronchodilator drug which causes airways to expand. The most effective bronchodilators are the β-adrenergic agonists which mimic the actions of adrenalin. These are widely used and are simply administered to the lungs by inhalers. However, bronchoconstrictor drugs are primarily of use in short term symptomatic relief, and do not prevent asthma attacks nor deterioration of lung function over the long term.

Anti-inflammatory drugs such as cromoglycate and the corticosteroids are also widely used in asthma therapy. Cromoglycate has anti-inflammatory activity and has been found to be extremely safe. Although such cromolyns have minimal side effects and are currently preferred for initial preventive therapy in children, it is well known that they are of limited efficacy.

The use of corticosteroids in asthma therapy was a major advance since they are very effective anti-inflammatory agents, however, steroids are very powerful, broad spectrum anti-inflammatory agents and their potency and non-specificity means that they are seriously limited by adverse side effects.

Localising steroid treatment to the lungs using inhaler technology has reduced side effects but the reduced systemic exposure following inhalation still results in some undesirable effects. Hence, there is a reluctance to use steroids early in the course of the disease.

There therefore still remains a need for an alternative asthma therapy which is a safe, effective, anti-inflammatory or immunomodulatory agent which can be taken to treat chronic asthma.

Tryptase is the major secretory protease of human mast cells and is proposed to be involved in neuropeptide processing and tissue inflammation. Tryptase is one of a large number of serine protease enzymes which play a central role in the regulation of a wide variety of physiological processes including coagulation, fibrinolysis, fertilization, development, malignancy, neuromuscular patterning and inflammation. Although a large number of serine proteases have been widely investigated, tryptase still remains relatively unexplored.

Mature human tryptase is a glycosylated, heparin-associated tetramer of catalytically active subunits. Its amino-acid structure appears to have no close counterpart among the other serine proteases which have been characterised. Tryptase is stored in mast cell secretory granules and after mast cell activation, human tryptase can be measured readily in a variety of biological fluids. For example, after anaphylaxis, tryptase appears in the blood stream where it is readily detectable for several hours. Tryptase also appears in samples of nasal and lung lavage fluid from atopic subjects challenged with specific antigen. Tryptase has been implicated in a variety of biological processes where activation and degranulation of mast cells occur. Accordingly, mast cell tryptase inhibition may be of great value in the prophylaxis and treatment of a variety of mast cell mediated conditions. Mast cells can degranulate by both IgE-dependent and independent mechanisms thereby implicating tryptase in both atopic and non-atopic inflammatory conditions. Tryptase can activate proteases such as pro-urokinase and pro-MMP3 (pro-matrix metalloprotease 3, pro-stromelysin), thereby indicating a pathological role in tissue inflammation and remodelling. Furthermore, the recent evidence that tryptase can activate certain G-protein coupled receptors (eg PAR2) and induce neurogenic inflammation points to a broader physiological role, for example in modulating pain mechanisms. Given tryptase's multiple mechanisms of action, it has been proposed that tryptase inhibitors may be beneficial in a broad range of diseases. These include conditions such as: asthma (specifically influencing the inflammatory component, the underlying hyperreactivity, and the chronic fibrotic damage due to smooth muscle thickening); chronic obstructive pulmonary disease (COPD) and pulmonary fibrotic diseases; rhinitis; psoriasis; urticaria; dermatitis; arthritis; Crohn's disease; colitis; angiogenesis; atherosclerosis; multiple sclerosis; interstitial cystitis; migraine headache; neurogenic inflammation and pain mechanisms; wound healing; cirrhosis of the liver; Kimura's disease; pre-eclampsia; bleeding problems associated with menstruation and the menopause; cancer (particularly melanoma and tumour metastasis); pancreatitis; and certain viral infections (Yong, Exp. Toxic Pathol, 1997, 49, 409; Steinhoff et al., Nat. Med., 2000, 6, 151; Downing and Miyan, Immunol. Today, 2000, 21, 281; Tetlow and Wooley, Ann. Rheum. Dis., 1995, 54, 549; Jeziorska, Salamonsen and Wooley, Biol. Reprod., 1995, 53, 312; Brain, Nat. Med., 2000, 6, 134; Olness et al., Headache, 1999, 39, 101.) The underlying principle is that a tryptase inhibitor should have utility where mast cells have being induced to degranulate by whatever mechanism, including anaphylactic reactions due to exogenous substances, e.g. morphine-induced bronchoconstriction (Bowman and Rand, Textbook of Pharmacology, $2^{nd}$ edt., 1980.)

In WO96/09297, WO95/32945, WO94/20527 and U.S. Pat. No. 5,525,623 a variety of peptide based compounds are suggested as potential inhibitors of the mast cell protease tryptase. In WO95/03333 a tryptase inhibitor is provided by a polypeptide obtainable from the leech hirudo medicinalis. In WO96/08275 secretory leukocyte protease inhibitor (SLPI) and active fragments thereof have been found to inhibit the proteolytic activity of tryptase. In WO99/55661 certain 4-aminomethylbenzoic ester derivatives are proposed as potential tryptase inhibitors.

We have now found that certain aromatic compounds carrying lipophilic side chains are particularly effective as inhibitors of the serine protease, tryptase.

It is envisaged that the compounds of the invention will be useful not only in the treatment and prophylaxis of asthma but also of other allergic and inflammatory conditions mediated by tryptase such as allergic rhinitis, skin conditions such as eczema, psoriasis, atopic dermatitis and urticaria, rheumatoid arthritis, conjunctivitis, inflammatory bowel disease, neurogenic inflammation, atherosclerosis and cancer.

Thus viewed from one aspect the invention provides a tryptase inhibitor compound of formula (I)

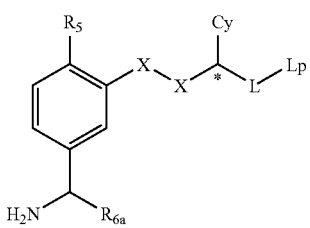

(I)

where:

$R_5$ represents amino, hydroxy, aminomethyl, hydroxymethyl or hydrogen;

$R_{6a}$ represents hydrogen or methyl;

X—X is selected from —CH=CH—, —CONR$_{1a}$—, —NH—CO—, —NR$_{1a}$—CH$_2$—, —CH$_2$—NR$_{1a}$—, —CH$_2$O—, —OCH$_2$—, —COO—, —OC=O— and —CH$_2$CH$_2$—;

$R_{1a}$ represents hydrogen, (1–6C)alkyl or phenyl(1–6C)alkyl;

L is CO or CONR$_{1d}$(CH$_2$)$_m$ in which m is 0 or 1 and $R_{1d}$ is hydrogen, (1–6C)alkyl or phenyl(1–6C)alkyl;

Cy is a saturated or unsaturated, mono or poly cyclic, homo or heterocyclic group, preferably containing 5 to 10 ring atoms and optionally substituted by one or more groups $R_{3a}$— or $R_{3i}X_i$—;

each $R_{3a}$ independently is hydrogen, hydroxyl, (1–6C) alkoxy, (1–6C)alkyl, (2–6C)alkenyl, (2–6C)alkynyl, (1–6C) alkanoyl, (1–6C)alkylaminoalkyl, hydroxy(1–6C)alkyl, carboxy, (1–6C)alkoxyalkyl, (1–6C)alkoxycarbonyl, (1–6C) alkylaminocarbonyl, amino(1–6C)alkyl CONH$_2$, CH$_2$CONH$_2$, aminoacetyl, (1–6C)alkanoylamino, (1–6C) alkoxycarbonylamino, amino, halo, cyano, nitro, thiol, (1–6C)alkylthio, (1–6C) alkylsulphonyl, (1–6C)alkylsulphenyl, imidazolyl, hydrazido, (1–6C)alkylimidazolyl, (1–6C)alkylsulphonamido, (1–6C) alkylaminosulphonyl, aminosulphonyl, (1–6C) haloalkoxy, or (1–6C) haloalkyl;

$X_i$ is a bond, O, NH or CH$_2$; and $R_{3i}$ is phenyl optionally substituted by $R_{3a}$;

provided that the compound of formula I is not 3-aminomethylbenzoyl-D-phenylglycine-4-aminomethylcyclohexyl-methylamide or 3-aminomethylbenzoyl-D-phenylglycine-1-adamantylamide;

or a physiologically tolerable salt thereof, e.g. a halide, phosphate or sulphate salt or a salt with ammonium or an organic amine such as ethylamine or meglumine.

Compounds of formula I have surprisingly been found to be particularly effective as inhibitors of tryptase and to show a surprising selectivity for tryptase over other serine proteases.

In the compounds of the invention, $R_5$ preferably represents amino or hydrogen, more preferably hydrogen.

$R_{6a}$ preferably represents hydrogen.

In the compounds of the invention, the alpha atom (*) preferably has the conformation that would result from construction from a D-α-aminoacid NH$_2$—CH(Cy)-COOH where the NH$_2$ represents part of X—X.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. $C_{1-6}$ or $C_{1-3}$; cyclic groups preferably have ring sizes of 3 to 8 atoms; and fused multicyclic groups preferably contain 8 to 16 ring atoms.

$R_{1a}$ is preferably hydrogen.

X—X may, for example, be selected from —CH=CH—, —CONR$_{1a}$—, —NH—CO—, —NH—CH$_2$—, —CH$_2$—NH—, —CH$_2$O—, —OCH$_2$—, —COO—, —OC=O— and —CH$_2$CH$_2$—.

Preferably, the X moiety nearest to the alpha atom is an NH or O atom, most preferably an NH group. The X moiety alpha to the aromatic ring is preferably a carbon based group such as CH$_2$ or CO, preferably CO. Thus a particularly preferred linker X—X is —CONH—.

Examples of particular values for $R_{1d}$ are:

hydrogen;

for (1–6C)alkyl: methyl or ethyl; and for phenyl(1–6C)alkyl: benzyl or phenylethyl.

$R_{1d}$ is preferably hydrogen.

Examples of particular values for L are CO, CONH, CON(CH$_3$) and CONHCH$_2$, more preferably CO, CONH or CON(CH$_3$).

It will be appreciated by those skilled in the art that a diverse range of organic groups are lipophilic, and that it is therefore impractical to define with precision each and every structure that may be incorporated into a serine protease inhibitor according to the invention. Accordingly, it is being assumed that the addressee of this specification will not require an exhaustive computer listing of structures of lipophilic groups, but will instead make use of the structures of lipophilic groups disclosed in the specification, especially those exemplified; the test systems described herein for identifying tryptase inhibitors; and common general knowledge of the lipophilicity, synthesis and stability of organic compounds, to obtain novel inhibitor compounds of formula (I).

The lipophilic group may be, for example, an alkyl, alkenyl, carbocyclic or heterocyclic group, or a combination of two or more such groups linked by a spiro linkage or a single or double bond or by C=O, O, OCO, COO, S, SO, SO$_2$, CONR$_{1e}$, NR$_{1e}$—CO— or NR$_{1e}$ linkage (where R$_{1e}$ is as defined for R$_{1a}$), optionally substituted by one or more oxo or R$_3$ groups in which R$_3$ is an amino acid residue, N-(1–6C)alkylaminocarbonyl, N,N-di(1–6C)alkylaminocarbonyl, N-(1–6C)alkylaminoalkanoyl, N-(1–6C)alkanoylamino(1–6C)alkanonyl, C-hydroxyamino(1–6C)alkanoyl, hydroxy(2–6C)alkanoylamino(1–6C)alkanoyl, di(1–6C)alkylaminosulfonyl, hydrogen, hydroxyl, (1–6C)alkoxy, (1–6C)alkanoyloxy, (1–6C)alkyl, (2–6C)alkenyl (2–6C)alkynyl, (3–6C)alkenyloxycarbonyl, (1–6C)alkanoyl, amino(1–6C)alkyl, amido(CONH$_2$), amino(1–6C)alkanoyl, aminocarbonyl(1–5C)alkanoyl, hydroxy(1–6C)alkyl, carboxy, hydroxy(1–6C)alkanoyl, (1–6C)alkoxy(1–6C)alkyl, (1–6C)alkoxycarbonyl(1–5C)alkyl, (1–6C)alkoxycarbonyl, (1–6C)alkanoylamino, amino, halo, cyano, nitro, thiol, (1–6C)alkylthio, (1–6C)alkylsulfonyl, (1–6C)alkylsulphenyl and hydrazido.

Preferably the lipophilic group is a carbocyclic or heterocyclic group, or a combination of a carbocyclic or heterocyclic group with one or more alkyl, alkenyl, carbocyclic or heterocyclic groups, linked by a spiro linkage or a single or double bond or by C=O, O, OCO, COO, S, SO, SO$_2$, CONR$_{1e}$, NR$_{1e}$—CO— or NR$_{1e}$ linkage (where R$_{1e}$ is as defined for R$_{1a}$), optionally substituted by one or more oxo or R$_3$ groups.

$R_{1e}$ is preferably a hydrogen atom.

When the lipophilic group comprises an alkyl group, this may be, for example, a (1–3C)alkyl group, such as methyl, ethyl or propyl. Preferably an alkyl group is unsubstituted.

When the lipophilic group comprises a carbocyclic group, this may be, for example, a non-aromatic or aromatic, mono or polycyclic hydrocarbon group containing up to 25, more preferably up to 10 carbon atoms. The carbocyclic group may thus be, for example, a cycloalkyl, polycycloalkyl, phenyl or naphthyl group, or a cycloalkyl group fused with a phenyl group.

Examples of particular values for a cycloalkyl group are (3–6C) cycloalkyl groups, such as cyclopentyl and cyclohexyl. A cycloalkyl group is preferably unsubstituted or substituted by one group R$_3$, preferably an amino or alkyl group.

Examples of particular values for a polycycloalkyl group are (6–10C) polycycloalkyl groups, such as bicycloalkyl, for example decalinyl or norbornyl. A polycycloalkyl group is preferably unsubstituted or substituted by one, two or three R$_3$ groups, for example alkyl such as methyl. An example of a polycycloalkyl group substituted by alkyl is isopinocampheyl.

A phenyl group is preferably unsubstituted or substituted by one or two R$_3$ groups.

A naphthyl group is preferably unsubstituted or substituted by one R$_3$ group.

Examples of a cycloalkyl or cycloalkenyl group fused with a phenyl group are indanyl and tetrahydronaphthyl. This group is preferably unsubstituted or substituted by oxo or one or two R$_3$ groups. Examples of groups substituted by oxo are 1-oxoindan-5-yl, 1-oxo-1,2,3,4-tetrahydronaphth-7-yl and 1-oxo-1,2,3,4-tetrahydro-naphth-6-yl.

When the lipophilic group comprises a heterocyclic group, this may be, for example, a non-aromatic or aromatic, mono or polycyclic group containing one or two oxygen, nitrogen or sulfur atoms in the ring system, and in total up to 25, more preferably up to 10 ring system atoms.

Examples of a heterocyclic group when it is a non-aromatic monocyclic group are azacycloalkyl groups, such as pyrrolidinyl and piperidinyl; azacycloalkenyl groups, such as pyrrolinyl; diazacycloalkyl groups, such as piperazinyl; oxacycloalkyl groups, such as tetrahydropyranyl; oxaazacycloalkyl groups, such as morpholino; and thiacycloalkyl groups, such as tetrahydrothiopyranyl. A non-aromatic monocyclic group preferably contains 5, 6 or 7 ring atoms and is preferably unsubstituted or substituted by one group R$_3$.

Examples of a heterocyclic group when it is a non-aromatic polycyclic group are bicyclic groups, such as azacycloalkyl fused with phenyl, for example dihydroindolyl, dihydroisoindolyl, tetrahydroquinolinyl and tetrahydroisoquinolinyl; azacycloalkyl fused with cycloalkyl, such as decahydroisoquinolinyl; and thienyl fused with cycloalkyl, such as tetrahydrobenzo[b]thienyl or 4H-cyclopenta(b)thienyl.

Examples of a heterocyclic group when it is an aromatic monocyclic group are furyl, pyrrolyl, thienyl, imidazolyl, thiazolyl, pyridyl, pyridazinyl, pyrimidinyl, pyrazinyl and triazinyl, preferably unsubstituted or substituted by one or two R$_3$ groups.

Examples of a heterocyclic group when it is an aromatic polycyclic group are bicyclic groups such as benzofuryl, quinolinyl, isoquinolinyl, benzothienyl, indolyl and benzothiazolyl.

Where Lp comprises a combination of at least two groups, it preferably comprises a combination of two or three such groups. The groups are preferably linked by a single bond, C=O, OCO, COO, O or NR$_{1e}$.

Examples of particular values for R$_3$ are:

for an amino acid residue: N-acetylalaninoyl, serinoyl, threoninoyl, aspartoyl or glutamoyl;

for N-(1–6C)alkylaminocarbonyl: N-(1,3-dimethyl)butylamino-carbonyl;

for N,N-di(1–6C)alkylaminocarbonyl: N-methyl-N-ethylaminocarbonyl;

for N-(1–6C)alkylaminoalkanoyl: N-methylacetyl;

for N-(1–6C)alkanoylamino(1–6C)alkanonyl: 2-N-acetylaminoacetyl, 2-N-acetylaminopropanoyl or 2-N-(2-methylpropanoyl)aminoacetyl;

for C-hydroxyamino(1–6C)alkanoyl: 2-amino-3-hydroxypropanoyl or 2-amino-3-hydroxybutanoyl;

for hydroxy(2–6C)alkanoylamino(1–6C)alkanoyl: 2-hydroxyacetylaminoacetyl;
for di(1–6C)alkylaminosulfonyl: dimethylaminosulfonyl;
hydrogen;
hydroxyl;
for (1–6C)alkoxy: methoxy;
for (1–6C)alkanoyloxy: acetoxy;
for (1–6C)alkyl: methyl, ethyl, propyl, 2-propyl or 2,2-dimethylethyl;
for (2–6C)alkenyl: allyl;
for (2–6C)alkynyl: propynyl;
for (3–6C)alkenyloxycarbonyl: allyloxycarbonyl;
for (1–6C)alkanoyl: acetyl, propionyl or isobutyryl;
for amino(1–6C)alkyl: aminomethyl;
amido(CONH$_2$);
for amino(1–6C)alkanoyl: aminoacetyl(COCH$_2$NH$_2$), aminopropionyl (COCH$_2$CH$_2$NH$_2$) or 2-aminopropionyl (COCH(CH$_3$)NH$_2$);
for aminocarbonyl(1–5C)alkanoyl: aminocarbonylacetyl;
for hydroxy(1–6C)alkyl: hydroxymethyl or 1-hydroxyethyl;
carboxy;
for hydroxy(1–6C)alkanoyl: 2-hydroxyacetyl or 2-hydroxypropanoyl;
for (1–6C)alkoxy(1–6C)alkyl: methoxymethyl;
for (1–6C)alkoxycarbonyl(1–5C)alkyl: methoxycarbonylmethyl;
for (1–6C)alkoxycarbonyl: methoxycarbonyl or ethoxycarbonyl;
for (1–6C)alkanoylamino: formylamino or acetylamino;
amino;
for halo: chloro;
cyano;
nitro;
thiol;
for (1–6C)alkylthio: methylthio;
for (1–6C)alkylsulfonyl: methylsulphonyl or ethylsulfonyl;
for (1–6C)alkylsulphenyl: methylsulphenyl; and
hydrazido.

Most preferably, the lipophilic group is selected from

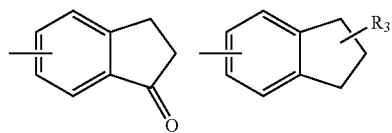
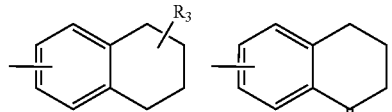
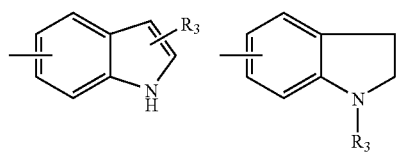
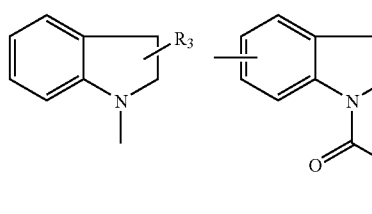

-continued

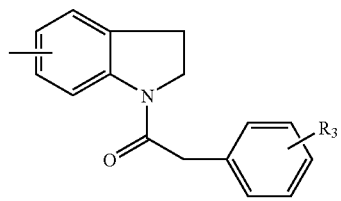
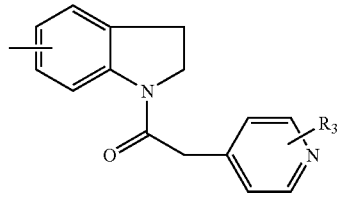
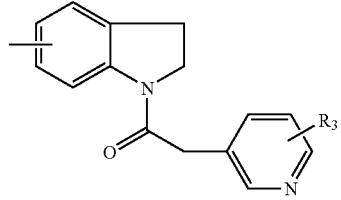
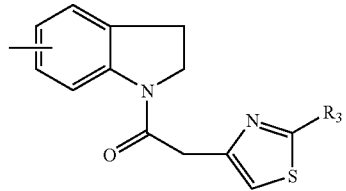
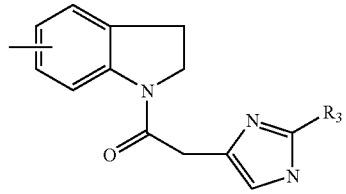

-continued
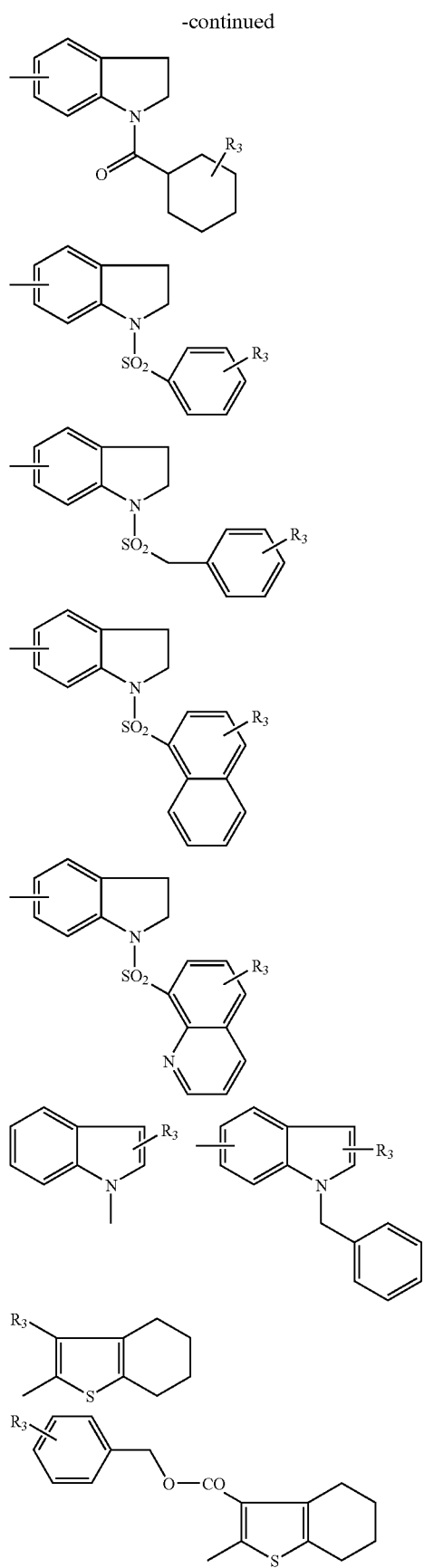
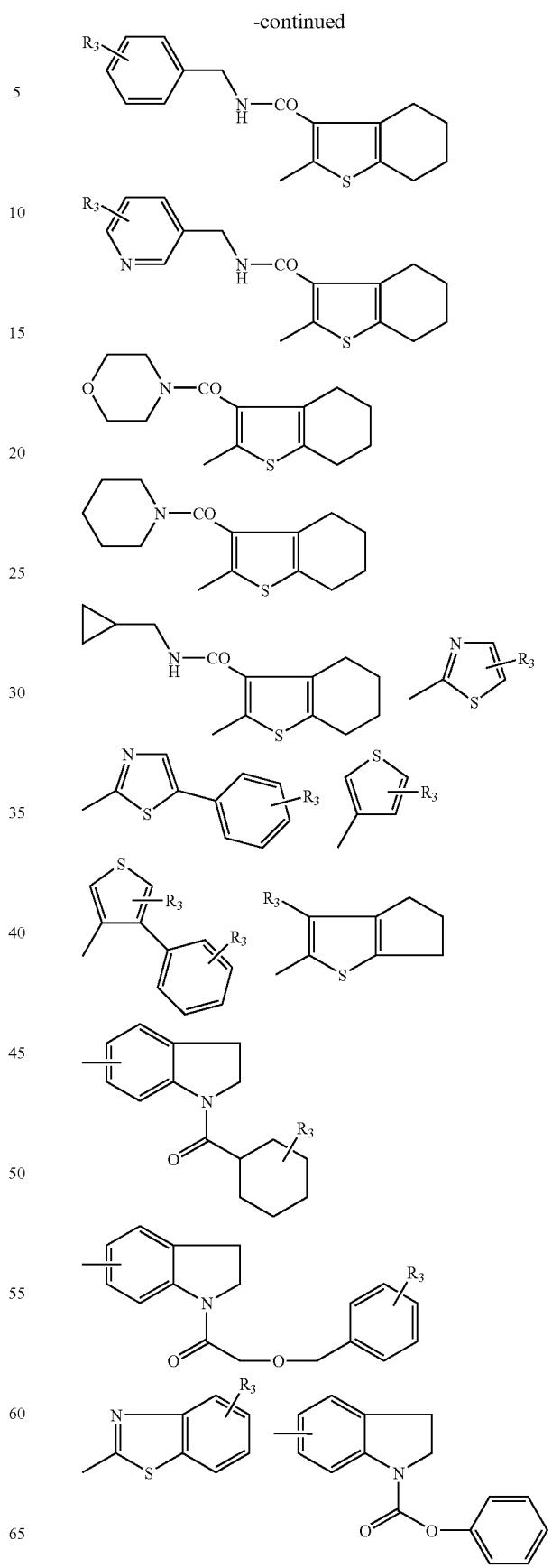

-continued

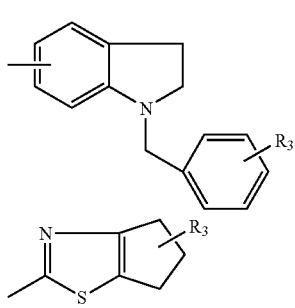
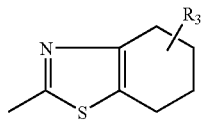

wherein R₃ is as hereinbefore defined; and

X represents CH or N.

In the Lp groups depicted above, preferably L represents CO when the Lp group is linked to L through N, or $CONR_{1d}$ (such as CONH or CONCH₃) when the Lp group is linked to L through C.

One group of compounds of particular interest is that in which L represents CO and Lp represents

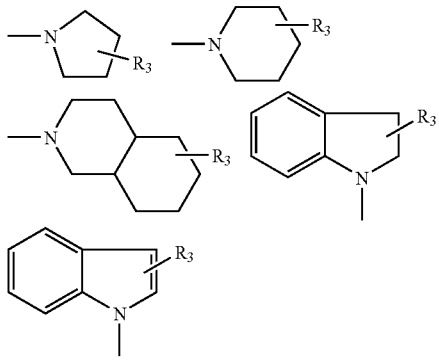

In this group of compounds, R₃ preferably represents hydrogen, hydroxyl or (1–6C)alkylaminocarbonyl.

Examples of particular values for Lp in this sub-group are pyrrolidin-1-yl, piperidin-1-yl, N-methyl, N-ethylaminocarbonylpiperidin-1-yl, decahydroisoquinolin-2-yl and 2,3-dihydroindol-1-yl.

Another group of compounds of particular interest is that in which L represents $CONR_{1d}$ (such as CONH or CONCH₃) and Lp represents

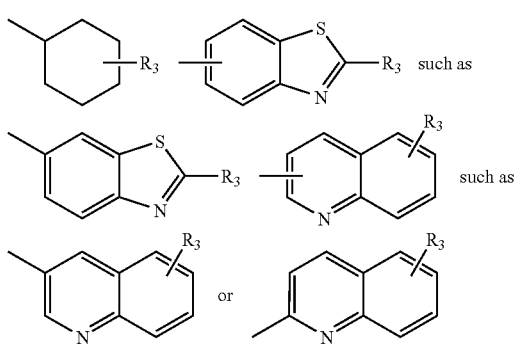

-continued

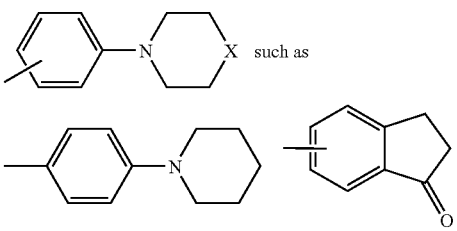
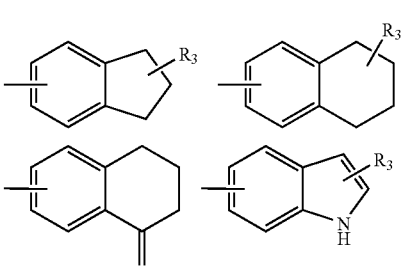
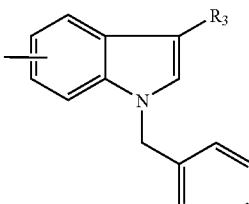
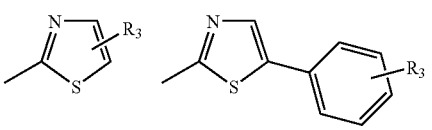
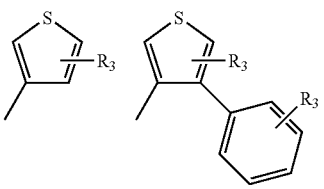

in which X is CH or N.

In this group of compounds, each R₃ is preferably selected independently from hydrogen, amino, hydroxy, (1–6C)alkyl, (1–6C)alkanoyl, (1–6C)alkanoyloxy, (1–5C)alkoxycarbonyl (1–6C)alkyl, amino(1–6C)alkyl or cyano.

Thus, values for R₃ in this group include hydrogen, amino, hydroxy, alkyl or aminoalkyl.

Examples of particular values are:
(i) 2-aminocyclohexyl;
(ii) 2-aminobenzothiazol-6-yl;
(iii) quinolin-3-yl or 8-acetoxyquinolin-2-yl;
(iv) 4-piperidin-1-ylphenyl or 4-piperazin-1-ylphenyl;
(v) 1-oxoindan-5-yl;
(vi) indan-5-yl;
(vii) tetrahydronaphth-6-yl or 1-methyltetrahydronaphth-6-yl;
(viii) 1-oxotetrahydronaphth-6-yl or 1-oxotetrahydronaphth-7-yl;

(ix) 2,3-dimethylindol-5-yl;
(x) N-benzyl-3-acetylindol-5-yl or N-benzyl-3-acetylindol-7-yl;
(xi) 3-ethoxycarbonyl-4,5-dimethylthien-2-yl;
(xii) 4-methyl-5-acetylthiazol-2-yl, 4,5-dimethylthiazol-2-yl, 4-methyl-5-ethoxycarbonylthiazol-2-yl, 3-cyano-4-methyl-5-ethoxycarbonylthiazol-2-yl or 4-methoxycarbonylmethyl-5-methylthiazol-2-yl;
(xiii) 5-phenylthiazol-2-yl;
(xiv) 2-methoxycarbonyl-5-(t-butyl)thien-3-yl;
(xv) 2-acetyl-5-phenylthien-3-yl; and
(xvi) 5,6-dihydro-3-methoxycarbonyl-4H-cyclopenta(b)thiophen-2-yl.

Another group of compounds of particular interest is that in which L represents CONR$_{1d}$ (such as CONH or CONCH$_3$) and Lp represents

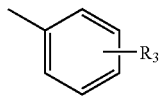

in which R$_3$ is (1–6C)alkylaminocarbonyl, N-(1–6C)alkylamino(1–6C)alkanoyl, N-(1–6C)alkanoylamino(1–6C)alkanonyl, C-hydroxyamino(1–6C)alkanoyl, hydrogen, (1–6C)alkoxy, (1–6C)alkyl, amino(1–6C)alkyl, aminocarbonyl, hydroxy(1–6C)alkyl, (1–6C)alkoxy(1–6C)alkyl, (1–6C)alkoxycarbonyl, (1–6C)acyloxymethoxycarbonyl, (1–6C)alkylamino, amino, halo, cyano, nitro, thiol, (1–6C)alkylthio, (1–6C)alkylsulphonyl, (1–6C)alkylsulphenyl, triazolyl, imidazolyl, tetrazolyl, hydrazido, (1–6C)alkylimidazolyl, thiazolyl, (1–6C)alkylthiazolyl, (1–6C)alkyloxazolyl, oxazolyl, (1–6C)alkylsulphonamido, (1–6C)alkylaminosulphonyl, aminosulphonyl, (1–6C)haloalkoxy or (1–6C)haloalkyl.

Preferably the phenyl group is unsubstituted or substituted by one or two R$_3$ groups.

Examples of particular values are phenyl, 3-cyano-4-methylphenyl, 3-aminocarbonylphenyl, 4-aminocarbonylphenyl, 4-chloro-3-aminocarbonylphenyl, 4-chlorophenyl, 3,5-dichlorophenyl, 3-aminomethylphenyl, 4-methyl-3-acetylaminophenyl, 4-(1-hydroxethyl)phenyl and 4-isopropylphenyl.

Another particular group of compounds of formula I is that in which L represents CONR$_{1d}$ (such as CONH or CONCH$_3$) and Lp represents

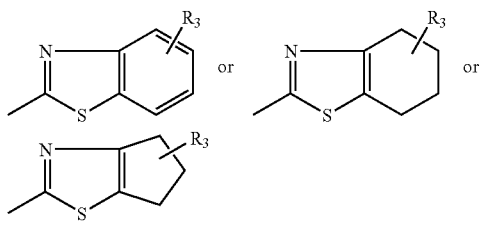

In this group of compounds, the heterocyclic group is preferably substituted by one or two R$_3$ groups. Each R$_3$ group is preferably selected from hydrogen, halogen such as chlorine, (1–6C)alkyl, such as methyl, and (1–6C)alkoxy, such as methoxy.

Accordingly, examples of particular values for Lp are: benzothiazol-2-yl, 4-chlorobenzothiazol-2-yl, 4-methylbenzo-thiazol-2-yl, 6-methylbenzothiazol-2-yl, 4-methoxybenzo-thiazol-2-yl and 5,6-dimethylbenzothiazol-2-yl.

Another particular group of compounds of formula I is that in which L represents CONR$_{1d}$ (such as CONH or CONCH$_3$) and Lp represents

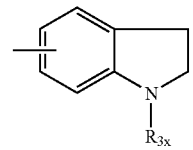

in which R$_{3x}$ represents R$_3$ or a group of formula

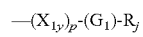

in which p is 0 or 1; X$_{1y}$ represents CO, COO, CONH or SO$_2$; G$_1$ represents (1–3C)alkanediyl, CH$_2$OCH$_2$ or, when p is 1, a bond; and R$_j$ represents a carbocyclic or heterocyclic group, optionally substituted by R$_3$.

Within this group of compounds, a sub-group of compounds may be identified in which R$_{3x}$ represents R$_3$ or a group of formula

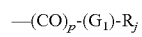

in which p is 0 or 1 and G$_1$ represents (1–3C)alkanediyl or, when p is 1, a bond.

It will be appreciated that when Lp represents a group as described above, it corresponds to a group in which Lp is a combination of a heterocyclic group (2,3-dihydroindolyl), a carbocyclic or heterocyclic group (R$_j$) and optionally an alkyl group (G$_1$), which groups are linked by a single bond or a carbonyl group. Accordingly, examples of particular values for R$_j$ are the examples given above for a carbocyclic or heterocyclic group forming part of Lp. Particular mention may be made of pyrrolidinyl, such as pyrrolidin-1-yl or pyrrolidin-2-yl; piperidinyl, such as piperidin-3-yl or piperidin-4-yl; aminocycloalkyl, such as 2-aminocyclohexyl or 4-aminocyclohexyl; phenyl; 2-hydroxypheny; 3-hydroxphenyl; 4-hydroxyphenyl; 4-aminomethylphenyl; 4-acetylaminomethylphenyl; 4-isopropylphenyl; 3,4-dihydroxyphenyl; naphthyl, such as 1-naphthyl; quinolinyl, such as 8-quinolinyl; aminothiazolyl, such as 2-aminothiazol-4-yl; formamidothiazolyl, such as 2-formamidothiazol-4-yl; imidazolyl, such as imidazol-4-yl; and pyridyl, such as pyrid-2-yl, pyrid-3-yl and pyrid-4-yl.

Examples of values for G$_1$ are a bond, —CH$_2$—, CH$_2$CH$_2$ and CH$_2$OCH$_2$.

The 2,3-dihydroindolyl group in the above formula is preferably a 2,3-dihydroindol-5-yl or -6-yl group, especially a 2,3-dihydroindol-6-yl group.

Examples of structures of compounds comprising a 2,3-dihydroindolyl group as described above are:

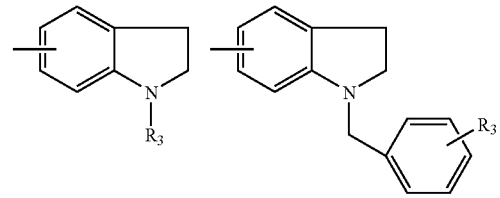

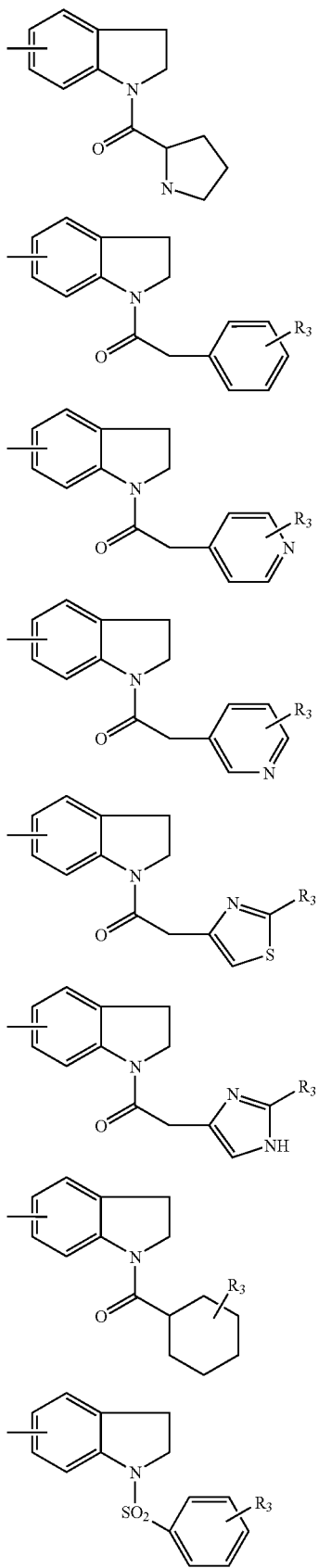
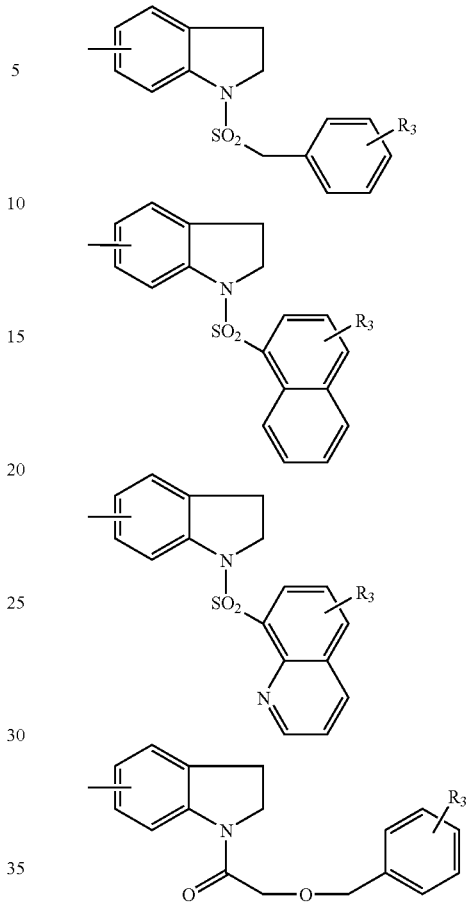

When $R_3$ is a substituent on the 1-position of a 2,3-dihydroindolyl group, it preferably represents an amino acid residue; (1–6C)alkylaminocarbonyl; N-(1–6C)alkylamino(1-6C)alkanoyl; N-alkanoylaminoalkanonyl; C-hydroxyamino(1-6C)alkanoyl; hydroxy(1–6C)alkanoylamino(1–6C)alkanoyl; di(1–6C)alkylaminosulfonyl; hydrogen; (1–6C)alkyl; (1–6C)alkanoyl; (1–6C)alkoxycarbonyl; (1–6C)acyloxymethoxycarbonyl; amino(1-6C)alkyl; amido (CONH$_2$); amino(1–6C)alkanoyl; aminocarbonyl(1–6C)alkanoyl; hydroxy(1–6C)alkyl; hydroxy(1–6C)alkanoyl; (1–6C)alkoxy(1–6C)alkyl; (1–6C)alkoxycarbonyl(1–6C)alkyl; (1–6C)alkoxycarbonyl; (1–6C)alkanoylamino; or (1–6C)alkylsulfonyl. Examples of particular values are: N-methylaminoacetyl, N-acetylaminoacetyl, N-acetylaminopropanoyl, N-(2-methylpropanoyl)aminoacetyl, N-acetylalaninoyl, serinoyl, threoninoyl, aspartoyl, glutamoyl, 2-hydroxyacetylaminoacetyl, dimethylaminosulfonyl, hydrogen, methyl, acetyl, propanoyl, 2-methylpropanoyl, 3-methylbutyryl, 2-hydroxypropanoyl, hydroxyacetyl, methoxycarbonylmethyl, methoxycarbonyl, amido, aminoacetyl, aminocarbonylacetyl, alaninoyl, methylsulfonyl or ethylsulfonyl group.

Accordingly, examples of particular values for Lp are: 1-(N-methylaminoacetyl)-2,3-dihydroindol-6-yl; 1-(N-acetylaminoacetyl)-2,3-dihydroindol-6-yl; 1-(N-acetylaminopropanoyl)-2,3-dihydroindol-6-yl; 1-N-(2-methylpropanoyl)aminoacetyl)-2,3-dihydroindol-6-yl; 1-(N-acetylalaninoyl)-2,3-dihydroindol-6-yl; 1-(serinoyl)-2,3-dihydroindol-6-yl; 1-(threoninoyl)-2,3-dihydroindol-6-yl;

1-(aspartoyl)-2,3-dihydroindol-6-yl; 1-(glutamoyl)-2,3-dihydroindol-6-yl; 1-(2-hydroxyacetylamino)acetyl-2,3-dihydroindol-6-yl, 1-(2-hydroxyacetylamino)acetyl-2,3-dihydroindol-6-yl, 1-amido-2,3-dihydroindol-6-yl, 2,3-dihydroindol-5-yl; 1-methyl-2,3-dihydroindol-6-yl; 1-allyloxycarbonyl-2,3-dihydroindol-5-yl; 1-acetyl-2,3-dihydroindol-6-yl; 1-propanoyl-2,3-dihydroindol-6-yl; 1-(2-methylpropanoyl)-2,3-dihydroindol-6-yl; 1-(3-methylbutyryl)-2,3-dihydroindol-6-yl; 1-(2-hydroxpropanoyl)-2,3-dihydroindol-6-yl; 1-hydroxacetyl-2,3-dihydroindol-6-yl; 1-methoxycarbonylmethyl-2,3-dihydroindol-6-yl; 1-methoxycarbonyl-2,3-dihydroindol-6-yl; 1-aminoacetyl-2,3-dihydroindol-6-yl; 1-aminocarbonylacetyl-2,3-dihydroindol-6-yl; 1-alaninoyl-2,3-dihydroindol-6-yl; 1-methylsulfonyl-2,3-dihydroindol-6-yl or 1-ethylsulfonyl-2,3-dihydroindol-6-yl.

When $R_3$ is a substituent on a cyclohexyl, phenyl, naphthyl, thiazolyl, imidazolyl, pyridyl or quinolinyl group, it is preferably hydrogen, hydroxy, amino, alkanoylamino, alkyl, aminoalkyl or alkanoylaminoalkyl. Examples of particular values are hydrogen, hydroxy, amino, formylamino, isopropyl, aminomethyl and acetylaminomethyl.

Accordingly, further examples of particular values for Lp are: 2,3-dihydroindol-5-yl, 1-(2-aminocyclohexyl)-carbonyl-2,3-dihydroindol-6-yl, 1-(4-aminocyclohexyl)-acetyl-2,3-dihydroindol-6-yl, 1-prolinoyl-2,3-dihydroindol-6-yl, 1-pyrrolidin-2-ylacetyl-2,3-dihydroindol-6-yl, 1-piperidin-3-ylcarbonyl-2,3-dihydroindol-6-yl, 1-piperidin-3-ylacetyl-2,3-dihydroindol-6-yl, 1-phenylacetyl-2,3-dihydroindol-6-yl, 1-(2-hydroxy)phenylacetyl-2,3-dihydroindol-6-yl, 1-(3-hydroxy)phenylacetyl-2,3-dihydroindol-6-yl, 1-(4-hydroxy)phenylacetyl-2,3-dihydroindol-6-yl, 1-(3,4-dihydroxy)phenylacetyl-2,3-dihydroindol-6-yl, 1-(4-aminomethyl)phenylacetyl-2,3-dihydroindol-6-yl, 1-(4-acetylaminomethyl)phenylacetyl-2,3-dihydroindol-6-yl, 1-(4-isopropyl)phenylacetyl-2,3-dihydroindol-6-yl, 1-phenylsulfonyl-2,3-dihydroindol-6-yl, 1-benzylsulfonyl-2,3-dihydroindol-6-yl, 1-naphth-1-ylsulfonyl-2,3-dihydroindol-6-yl, 1-quinolin-8-ylsulfonyl-2,3-dihydroindol-6-yl, 1-(4-pyridyl)acetyl-2,3-dihydroindol-6-yl, 1-(3-pyridyl)acetyl-2,3-dihydroindol-6-yl, 1-imidazol-4-ylacetyl-2,3-dihydroindol-6-yl, 1-(2-aminothiazol-4-yl)acetyl-2,3-dihydroindol-6-yl, and 1-(2-formamidothiazol-4-yl)acetyl-2,3-dihydroindol-6-yl, and 1-benzyl-2,3-dihydroindol-6-yl.

Another particular group of compounds of formula I is that in which L represents $CONR_{1d}$ (such as CONH or $CONCH_3$) and Lp represents

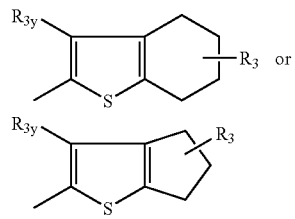

in which $R_{3y}$ represents $R_3$ or a group of formula

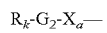

in which $G_2$ represents a bond or (1–3C)alkanediyl, $X_a$ represents a bond, CO, OCO, COO or NHCO, and $R_k$ represents a carbocyclic or heterocyclic group, optionally substituted by $R_3$.

It will be appreciated that when Lp represents a group as described above, it corresponds to a group in which Lp is a combination of a heterocyclic group (tetrahydrobenzothienyl), a carbocyclic or heterocyclic group ($R_k$) and optionally an alkyl group ($G_2$), which groups are linked by a single bond, or a CO, OCO, COO or NHCO group. Accordingly, examples of particular values for $R_k$ are the examples given above for a carbocyclic or heterocyclic group forming part of Lp. Particular mention may be made of phenyl; cycloalkyl, such as cyclopropyl; azacycloalkyl, such as piperidi-1-yl; oxazacycloalkyl, such as morpholino; and pyridyl, such as pyrid-3-yl.

Examples of values for $G_2$ are a bond, —$CH_2$—, and $CH_2CH_2$. Examples of structures of compounds comprising a 4,5,6,7-tetrahydrobenzothienyl group as described above are:

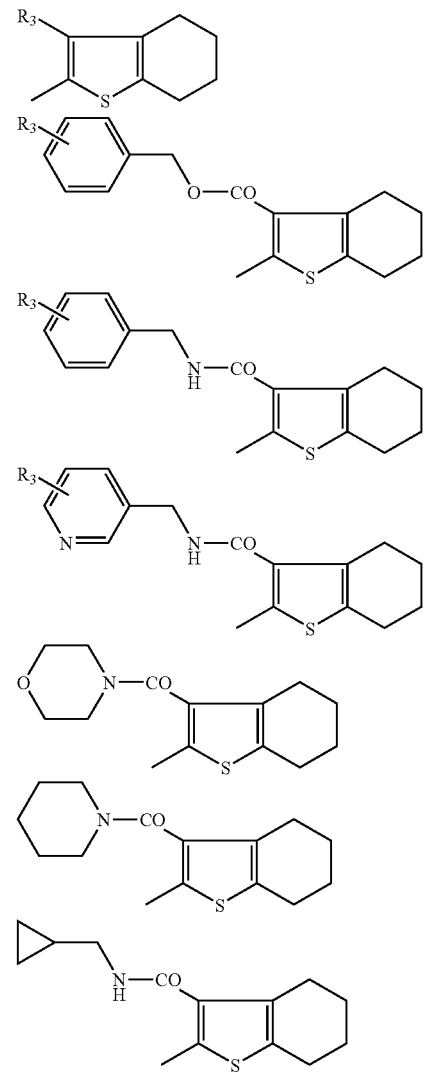

When $R_3$ is present as a substituent at the 3-position of a 4,5,6,7-tetrahydrobenzothiophene group, it preferably represents a carboxy group; a (1–6C)alkoxycarbonyl group, such as methoxycarbonyl or ethoxycarbonyl; or a (1–6C)alkylaminocarbonyl group, such as N-1,3-dimethylbutylaminocarbonyl.

Accordingly, examples of particular values for Lp are: 3-carboxy-4,5,6,7-tetrahydrobenzothien-2-yl, 3-ethoxy-carbonyl-4,5,6,7-tetrahydrobenzothien-2-yl and 3-N-(2,3-dimethylbutylaminocarbonyl-4,5,6,7-tetrahydrobenzothien-2-yl.

When $R_3$ is present as a substituent on a phenyl or pyridyl group, it is preferably a hydrogen atom.

Accordingly, further examples of particular values for Lp are: 3-benzyloxycarbonyl-4,5,6,7-tetrahydrobenzothien-2-yl, 3-benzylaminocarbonyl-4,5,6,7-tetrahydrobenzothien-2-yl, 3-(3-pyridyl)methylaminocarbonyl-4,5,6,7-tetrahydrobenzothien-2-yl, 3-cyclopropylmethylaminocarbonyl-4,5,6,7-tetrahydrobenzothien-2-yl, 3-morpholinocarbonyl-4,5,6,7-tetrahydrobenzothien-2-yl and 3-piperidinocarbonyl-4,5,6,7-tetrahydrobenzothien-2-yl.

The cyclic group attached to the alpha carbon is preferably cycloalkyl (such as cyclohexyl), piperidinyl (such as piperidin-4-yl), phenyl, 3,4-methylenedioxyphenyl, furyl, such as fur-2-yl, thienyl (such as thien-2-yl or thien-3-yl), imidazolyl (such as imidazol-4-yl), thiazolyl (such as thiazol-4-yl or thiazol-5-yl), pyridyl (such as pyrid-2-yl, pyrid-3-yl or pyrid-4-yl), naphthyl (such as naphth-1-yl or naphth-2-yl), benzofuryl (such as benzofur-2-yl), benzo[b]thienyl (such as benzo[b]thien-2-yl) group, optionally substituted by $R_{3a}$ or $R_{3i}X_i$ in which $X_i$ is a bond, O, NH or $CH_2$ and $R_{3i}$ is phenyl optionally substituted by $R_{3a}$.

In one group of compounds, each $R_{3a}$ independently is hydroxyl, (1–6C)alkoxy, (1–6C)alkyl, (1–6C)alkanoyl, (1–6C)alkylaminoalkyl, hydroxy(1–6C)alkyl, carboxy, (1–6C) alkoxyalkyl, (1–6C)alkoxycarbonyl, (1–6C)alkylaminocarbonyl, amino(1–6C)alkyl $CONH_{12}$ $CH_2CONH_2$, aminoacetyl, (1–6C)alkanoylamino, (1–6C)alkoxycarbonylamino, amino, halo, cyano, nitro, thiol, (1–6C)alkylthio, (1–6C)alkylsulphonyl, (1–6C)alkylsulphenyl, imidazolyl, hydrazido, (1–6C)alkylimidazolyl, (1–6C)alkylsulphonamido, (1–6C) alkylaminosulphonyl, aminosulphonyl, (1–6C) haloalkoxy, or (1–6C) haloalkyl.

Examples of particular values for $R_{3a}$ are:
hydrogen;
hydroxyl;
for (1–6C)alkoxy: methoxy, ethoxy or isopropoxy;
for (1–6C)alkyl: methyl, ethyl or isopropyl;
for: (1–6C)alkanoyl: acetyl, propanoyl or isopropanoyl,
for (1–6C)alkylaminoalkyl: methylaminomethyl or dimethylaminomethyl;
for (1–6C)hydroxyalkyl: hydroxymethyl carboxy;
for (1–6C)alkoxyalkyl: methoxymethyl;
for (1–6C)alkoxycarbonyl: methoxycarbonyl or ethoxycarbonyl;
for (1–6C)alkylaminocarbonyl: methylaminocarbonyl or dimethylaminocarbonyl;
for (1–6C)aminoalkyl: aminomethyl;
$CONH_2$;
$CH_2CONH_2$;
aminoacetyl;
for (1–6C)alkanoylamino: formylamino or acetylamino;
for (1–6C)alkoxycarbonylamino: methoxycarbonylamino, ethoxycarbonylamino or t-butoxycarbonylamino;
amino;
for halo: fluoro or chloro;
cyano;
nitro;
thiol;
for (1–6C)alkylthio: methylthio;
for (1–6C)alkylsulphonyl: methylsulphonyl or ethylsulphonyl;
for (1–6C)alkylsulphenyl: methylsulphenyl;
for imidazolyl: imidazol-4-yl;
hydrazido;
for (1–6C)alkylimidazolyl: 2-methylimidazol-4-yl;
for (1–6C)alkylsulphonamido: methylsulphonylamido or ethylsulphonylamido;
for (1–6C)alkylaminosulphonyl: methylaminosulphonyl or ethylaminosulphonyl;
aminosulphonyl;
for (1–6C) haloalkoxy: trifluoromethoxy; and
for (1–6C) haloalkyl: trifluoromethyl.

An example of a particular value for $R_{3i}$ is phenyl.

Examples of particular values for $R_{3i}X_i$ are phenyl, phenoxy, phenylamino and benzyl.

Cy is preferably unsubstituted or substituted by one or two $R_{3a}$ groups.

Preferably $R_{3a}$ is hydrogen, hydroxyl, methyl, ethyl, isopropyl, acetyl, propanoyl, isopropanoyl, isopropoxy, amino, aminomethyl, hydroxymethyl, carboxy, amido, formylamino, acetylamino, aminoacetyl or carboxy.

Examples of particular values for Cy are cyclohexyl, piperidin-4-yl, 1-acetylpiperidin-4-yl, 1-propanoylpiperidin-4-yl, 1-isobutyrylpiperidin-4-yl, 1-aminoacetylpiperidin-4-yl, phenyl, 4-aminophenyl, 3-hydroxyphenyl, 4-methylphenyl, 2,4-dimethylphenyl, 3,6-dimethylphenyl, 4-ethylphenyl, 4-isopropylphenyl, 4-hydroxphenyl, 3-aminomethylphenyl, 4-aminomethylphenyl, 4-($H_2NCO$)phenyl, 4-hydroxymethylphenyl, 3-hydroxymethylphenyl, 2-hydroxymethylphenyl, 4-carboxyphenyl, 4-isopropoxyphenyl, 2-chlorophenyl, 3,4-methylenedioxyphenyl, 4-phenylphenyl, 4-phenoxyphenyl, 5-methylfur-2-yl, imidazol-4-yl, 2-methylthiazol-4-yl, 2-aminothiazol-4-yl, 2-formylaminothiazol-4-yl, 2-aminothiazol-5-yl, 2-formylaminothiazol-5-yl, 2-phenylthiazol-4-yl, 4-aminopyrid-3-yl, 6-methylpyrid-2-yl, 3-amino-pyrid-4-yl, naphth-1-yl, naphth-2-yl, benzofur-2-yl or 3-methylbenzothien-2-yl.

A group of compounds of particular interest is that in which Cy is a group of formula

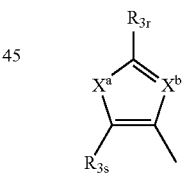

In which one of $X^a$ and $X^b$ is N and the other is NH or S, and each of $R_{3r}$ and $R_{3a}$ is as defined for $R_{3a}$.

Another group of compounds of particular interest is that of formula

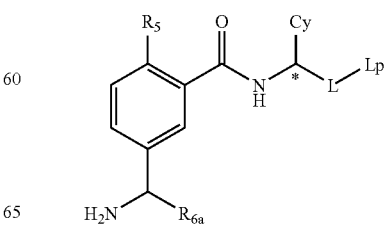

in which:

L-Lp represents CO-$L_x$; and $L_x$ is a mono or bicyclic group bound to the carbonyl via a pendent nitrogen atom or nitrogen atom which forms part of the mono or bicyclic ring;

or a physiologically tolerable salt thereof, e.g. a halide, phosphate or sulphate salt or a salt with ammonium or an organic amine such as ethylamine or meglumine.

It will be appreciated that when $L_x$ is bound to the carbonyl via a pendent nitrogen, the group CO-$L_x$ corresponds with the group L-Lp in which L is CONH and Lp is a mono or bicyclic group. When Lx is bound to the carbonyl via a nitrogen that forms part of the mono or bicyclic ring, the group CO-Lx corresponds with the group L-Lp in which L is CO and Lp is a mono or bicyclic group containing a nitrogen atom in the ring and bound to L via this nitrogen.

It is believed that an aminomethyl group positioned on the 3 position of the phenyl ring will give rise to excellent binding within the S1 binding pocket of tryptase. Without wishing to be limited by theory it is believed that the presence of a hydrogen bond donating group attached to the phenyl group will be essential for successful inhibition of tryptase.

$R_5$ and $R_6$ are both preferably hydrogen.

Most preferably the Lx group comprises

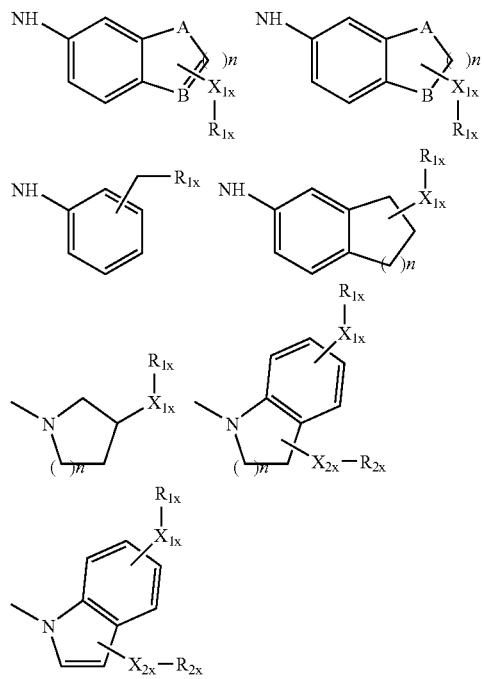

wherein:

A and B are independently chosen from NH, N, O, S, CH, $CH_2$;

$X_{1x}$ and $X_{2x}$ are independently chosen from $(CH_2)_m$, $(CH_2)_m CH=CH(CH_2)_p$, $CO(CH_2)_m$, $NH(CH_2)_m$, $NHCO(CH_2)_m$, $CONH(CH_2)_m$, $SO_2NH(CH_2)_m$, $NHSO_2(CH_2)_m$;

n is 1 or 2;

m is 0 to 2;

p is 0 to 2;

$R_{1x}$ and $R_{2x}$ are independently chosen from hydrogen, alkoxy, alkyl, aminoalkyl, hydroxyalkyl, alkoxyalkyl, alkoxycarbonyl, amino, halo, cyano, nitro, thiol, alkylthio, alkylsulphonyl, alkylsulphenyl, oxo, heterocyclo optionally substituted by $R_{3x}$, cycloalkyl optionally substituted by $R_{3x}$ or aryl optionally substituted by $R_{3x}$; and $R_{3x}$ is hydrogen, alkoxy, alkyl, amino, hydroxy, alkoxy, alkoxycarbonyl, halo, cyano, nitro, thiol, sulphonyl, or sulphenyl.

Examples of heterocyclic $R_{1x}$ and $R_{2x}$ groups are piperidine, piperazine and pyrrolidine.

The cyclic group attached to the alpha atom is preferably an optionally $R_{3a}$ substituted phenyl.

Thus, one group compounds of the invention are those of formula (II)

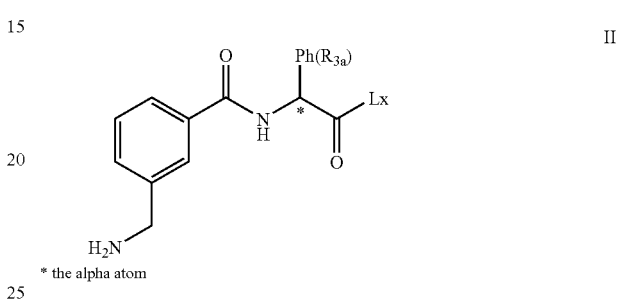

* the alpha atom wherein Lx is as hereinbefore defined. It is envisaged that especially preferred Lx groups will be those in which a cyclic or bicyclic ring is substituted by hydrogen bond donating and/or acceptor groups.

The compounds of the invention may be prepared by conventional chemical synthetic routes, e.g. by amide bond formation to couple the aromatic function to the alpha atom and to couple the lipophilic function to the alpha atom. The cyclic group-alpha atom combination may conveniently derive from an alpha amino acid (preferably of D configuration) with the aromatic deriving from for example an acid derivative of a compound based on $R_2$, e.g. an aminomethylbenzoic acid (which is readily available). Amide formation from such reagents (in which any amino or hydroxyl function (especially in an aminomethyl group) may if desired be protected during some or all of the synthesis steps) yields a compound of formula (V).

$$R_2\text{—CONH—CH(Cy)-COOH} \qquad (V)$$

(where $R_2$ represents

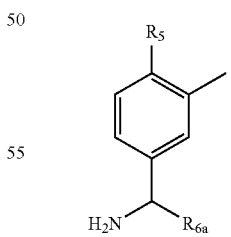

and Cy is as defined above).

Prior to reaction the amino group in an aminoalkyl group should be protected by an appropriate protecting group, PG, e.g. Boc, Z, Fmoc or Bpoc. The use of protecting groups is described in McOmie, "Protective Groups in Organic Chemistry", Plenum, 1973 and Greene, "Protective Groups in Organic Synthesis", Wiley Interscience, 1981.

The lipophilic group may then conveniently be introduced by reaction of a compound of formula (V) (or another analogous carboxylic acid) optionally after transformation into an activated form, e.g. an acid chloride or active ester, with a lipophilic group carrying or containing an amine group to produce a compound with the linkage of —CO— or —CO—NR$_{1d}$(CH$_2$)$_m$— from the alpha atom to the lipophilic group. The protecting group, PG, is then removed.

Alternatively a compound of formula V or another analogous carboxylic acid may be transformed into an alcohol by reaction with isobutylchloroformate and reduction with sodium borohydride.

Such an alcohol, e.g. of formula (VI)

can be reacted to introduce the lipophilic group by reactions such as:

oxidation of the alcohol to form a corresponding aldehyde (e.g. by oxidation with manganese dioxide or DMSO/oxalyl chloride or DMSO/SO$_3$ or Dess-Martin reagent) which may be reacted to introduce the lipophilic group by reactions such as:

reaction with an organometallic, eg a Grignard reagent, optionally followed by oxidation of the resulting hydroxyl group (e.g. with MnO$_2$, DMSO/oxalyl chloride or Dess-Martin reagent.

In this way compounds with the linkage of —CO— between the alpha carbon and the lipophilic group may be produced.

An alternative route to these compounds is to carry out any of the above chemical reactions to incorporate the lipophilic group into a protected intermediate such as a compound of formula (VII).

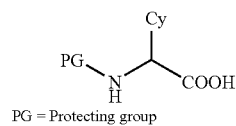

PG = Protecting group

The protecting group may then be removed before coupling of the 3-aminomethylbenzoic acid (optionally protected).

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include C$_1$–C$_6$ alkyl groups such as methyl, ethyl, t-butyl and t-amyl; aryl(C$_1$–C$_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents C$_{1-6}$ alkyl, C$_{3-10}$ cycloalkyl, phenyl C$_{1-6}$ alkyl, phenyl, C$_{1-6}$ alkoxy, phenyl C$_{1-6}$ alkoxy, or a C$_{3-10}$ cycloalkoxy, wherein a phenyl group may be optionally substituted, for example by one or two of halogen, C$_1$–C$_4$ alkyl and C$_1$–C$_4$ alkoxy. Preferred amino protecting groups include t-butoxycarbonyl (Boc) and benzyl.

α-Amino acids of formula (VII) which are not commercially available can be synthesized by methods known in the art, for example as described in "Synthesis of Optically Active α-Amino Acids" by Robert M. Williams (Pergamon Press, 1989) and "Asymmetric Synthesis of ArylGlycines", Chem. Rev. 1992, 889–917.

Compounds of the type (VII) made be prepared (for example) by one or more of the following methods.

(i) from aryl or heteroaryl aldehydes via the Strecker synthesis or modifications thereof, via Bucherer-Bergs hydantoin synthesis, or via the Ugi methodology (Isonitrile Chemistry, Ugi I. Ed.; Academic: New York, 1971; pp 145–199) with removal and replacement of protecting groups;

(ii) from styrenes via Sharpless methodology (J. Am. Chem. Soc. 1998, 120, 1207–1217)

(iii) from aryl boronic acids via Petasis methodology (Tetrahedron, 1997, 53, 16463–16470) with removal and replacement of protecting groups;

(iv) from aryl and heteroaryl acetic acids—via Evan's azidation (Synthesis, 1997, 536–540) or by oximation, followed by reduction and addition of protecting groups;

(v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid; or (vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487–490).

Examples of synthetic schemes are shown below:

Synthesis of Protected 4-aminomethylphenylgylcine

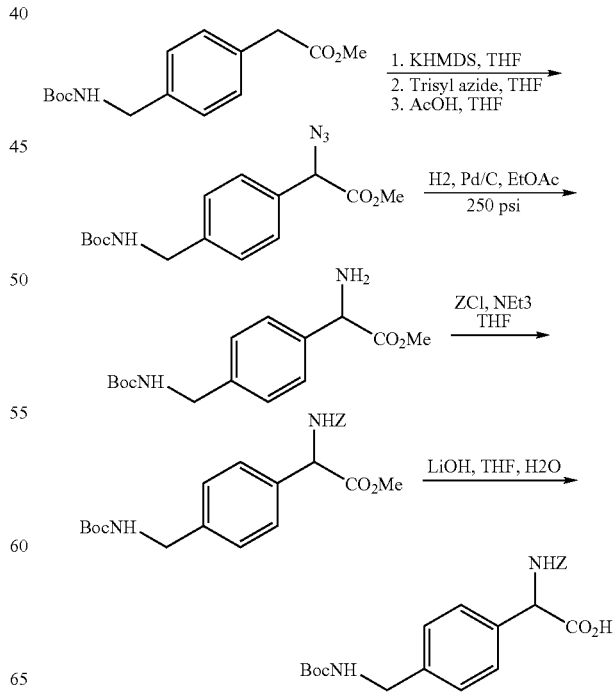

Synthesis of Protected 4-piperidylglycine
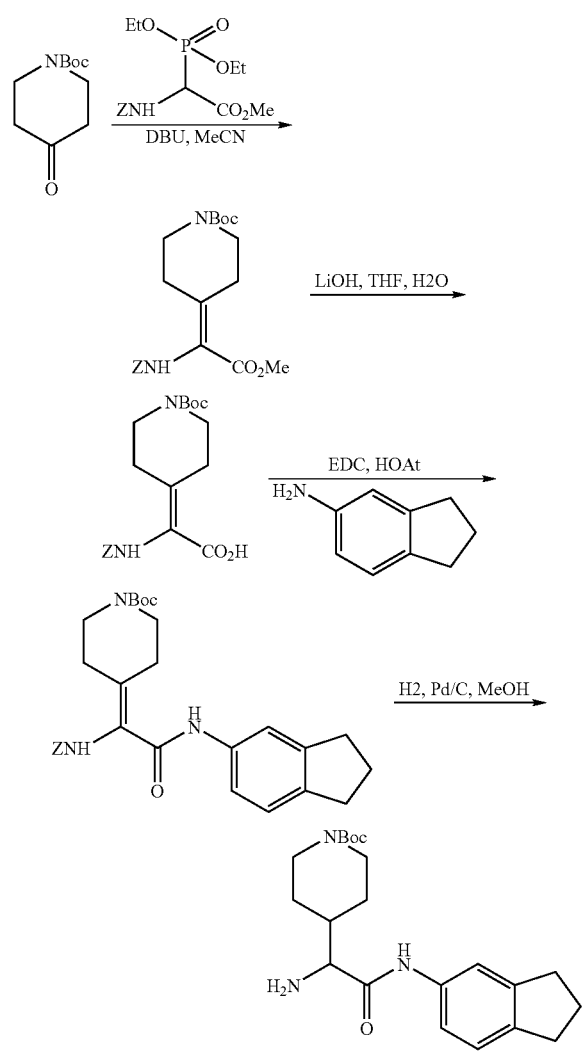
Synthesis of protected 2-aminothiaz-4-ylglycine
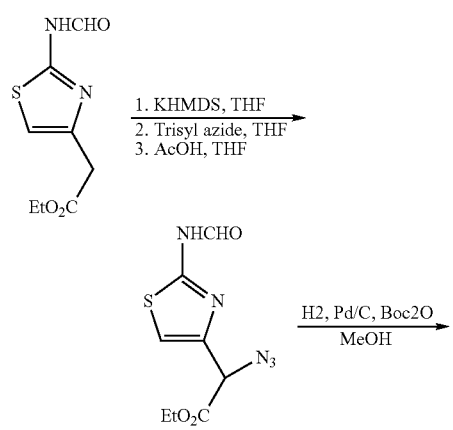
-continued
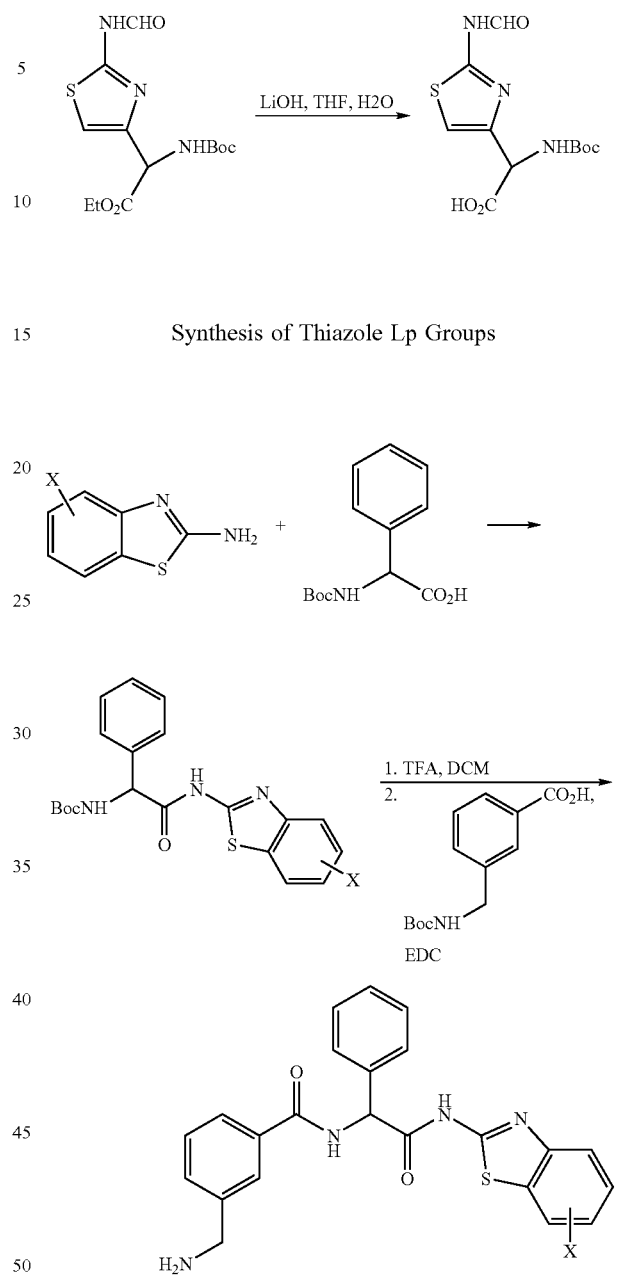
Synthesis of Thiazole Lp Groups
Synthesis of Alternative Thiazole Lp Groups
Benzthiazole Synthesis from Anllines
4-substituted
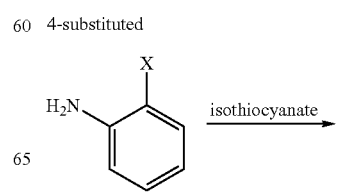

-continued
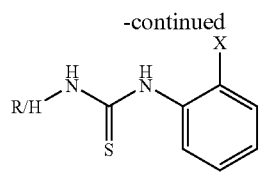
R = removable protecting group
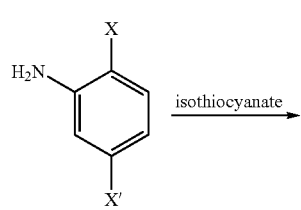
For 7-substitution
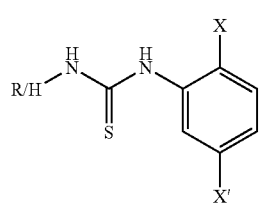
R = removable protecting group
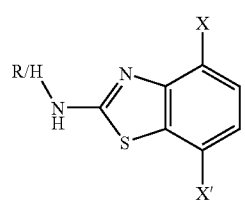
Cyclic Aliphatic Fused Aminothiazoles
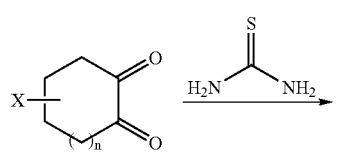
-continued
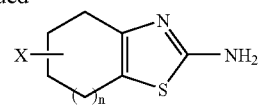
Synthesis of Thiophene Lp Groups
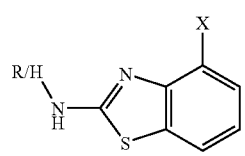
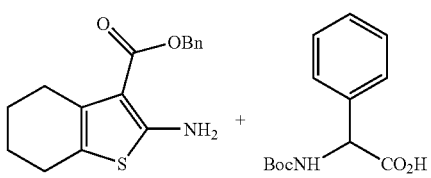
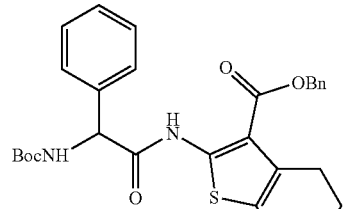
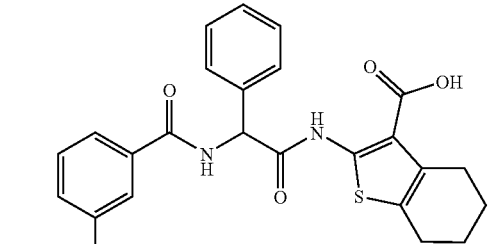
↓
Amides etc
Synthesis of Compounds with Different Cyclic Groups (Cy)
Ugi Synthesis
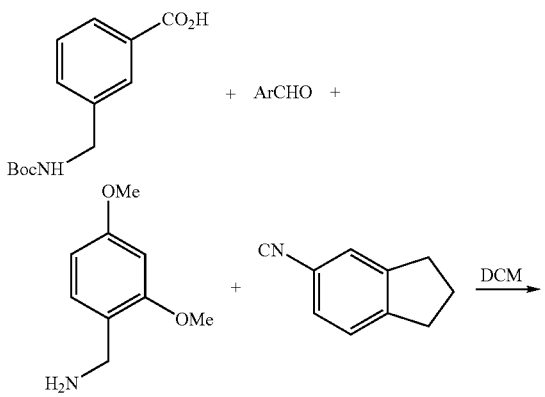

-continued

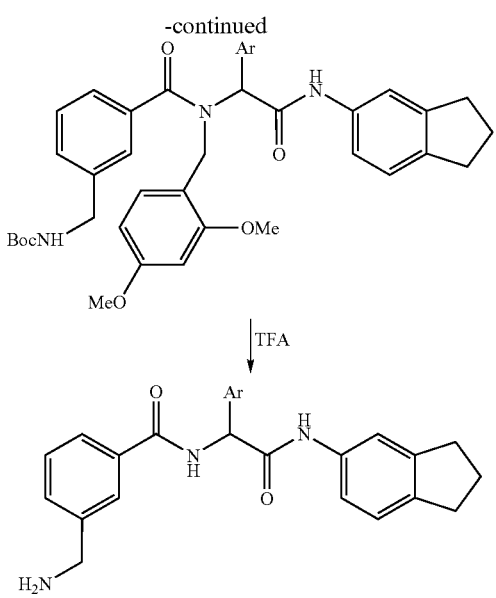

Synthesis of Thiazole Cy Groups

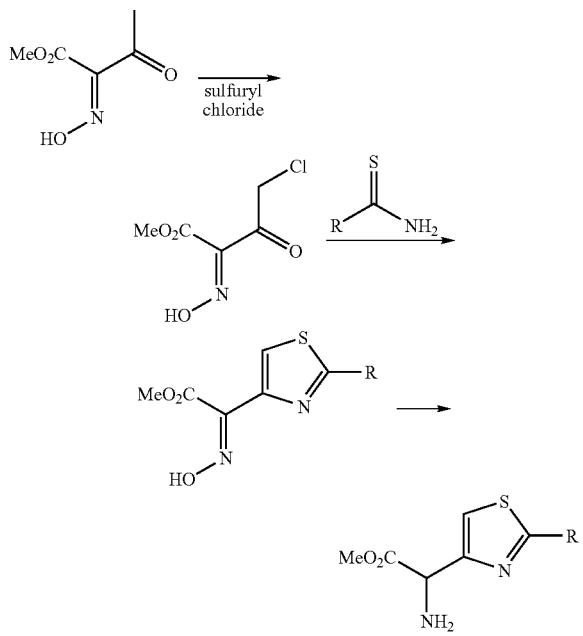

Thus viewed from a further aspect, the invention provides a process for the preparation of a compound according to the invention which process comprises coupling a lipophilic group to a compound of formula (VIII)

$$R_2—(X)_2—Y(Cy)-Z_1 \quad (VIII)$$

or a protected derivative thereof (wherein $R_2$, X, Y and Cy are as defined above and $Z_1$ is a reactive functional group).

Instead of introducing the group L-Lp as the final stage process step, the compounds of formula I may alternatively be prepared by a process in which the group $R_2$ is introduced in the final process step.

Thus viewed from another aspect the invention provides a process for the preparation of a compound according to the invention which process comprises reacting a compound of formula (IX)

$$Z_2-Y(Cy)-L-Lp \quad (IX)$$

(wherein Y, Cy, L and Lp are as defined above and $Z_2$ is HX or a reactive functional group), or a protected derivative thereof, with a compound of formula (X)

$$R_2-Z_3 \quad (X)$$

(wherein $R_2$ is as defined above and $Z_3$ is XH or an appropriate reactive group), or a protected derivative thereof, followed if necessary by the removal of any protecting groups.

Thus, for a compound of formula I in which X—X represents CONH, a compound of formula (IX) in which $Z_2$ is $H_2N$ may be reacted with a compounds of formula (X) in which $Z_3$ is COOH or a reactive derivative thereof, such as an acyl halide or an anhydride, for example as described in the Examples herein.

In another aspect the invention relates to a process for preparing a compound of formula I comprising deprotecting a compound of formula (I'):

$$R^{2'}—X—X—Y(Cy')-L-Lp \quad (I)'$$

Wherein $R^{2'}$ is $R^2$ (as hereinabove defined) or protected $R^2$, Cy' is Cy (as hereinabove defined) or protected Cy and Lp' is Lp (as hereinabove defined) or protected Lp; providing at least one protecting group is present.

If necessary physiologically tolerable salts can be formed using methods known in the art.

Where the lipophilic group Lp comprises more than one group, it may generally be formed by coupling these groups together at an appropriate stage in the preparation of the compound of formula I using conventional methods or as described in the Examples.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

Formulation 1

Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Viewed from this aspect the invention provides a pharmaceutical composition comprising a serine protease (tryptase) inhibitor according to the invention together with at least one pharmaceutically acceptable carrier or excipient.

The pharmaceutical composition may also optionally comprise at least one further anti-inflammatory.

Viewed from a further aspect the invention provides the use of a tryptase inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a tryptase inhibitor.

The dosage of the inhibitor compound of the invention will depend upon the nature and severity of the condition being treated, the administration route and the size and species of the patient. However in general, quantities of from 0.01 to 100 µmol/kg bodyweight will be administered.

All publications referred to herein are hereby incorporated by reference.

The invention will now be described further with reference to the following non-limiting Examples.

EXPERIMENTAL

Abbreviations used follow IUPAC-IUB nomenclature. Additional abbreviations are HPLC, high-performance liquid chromatography; LC/MS, liquid chromatography/mass spectrometry; rt, retention time; NMR, nuclear magnetic resonance, TBTU, 2-(1H-(benzotriazol-1-yl)-1,1,3,3-tetramethyluroniumtetrafluoroborate. Starting materials were purchased from Aldrich (Gillingham, UK), Lancaster (Morecambe, UK), Avocado (Heysham, UK), Maybridge (Tintagel, UK), Nova Biochem (Nottingham, UK) or Bachem.

Purification:

Flash column chromatography was carried out using Merck silica gel Si60 (40–63 µm, 230–400 mesh). Purification of final products was by crystallisation, flash column chromatography or gradient reverse phase HPLC on a Waters Deltaprep 4000 at a flow rate of 50 mL/minute using a Deltapak C18 radial compression column (40 mm×210 mm, 10–15 mm particle size). Eluant A consisted of aqueous trifluoroacetic acid (0.1%) and eluant B 90% acetonitrile in aqueous trifluoroacetic acid (0.1%) with gradient elution (Gradient, 0 minutes 5% B for 1 minutes, then 5% B to 20% B over 4 minutes, then 20% B to 60% B over 32 minutes). Fractions were analysed by analytical HPLC and LC/MS before pooling those with >95% purity for lyophilisation.

Analysis:

Proton nuclear magnetic resonance ($^1$H NMR) spectra were recorded on a Bruker DPX300 (300 MHz). Analytical HPLC's were performed on a Shimadzu LC6 gradient system equipped with an autosampler. Eluant A consisted of aqueous trifluoroacetic acid (0.1%) and eluant B consisted of 90% acetonitrile and 10% water, containing trifluoroacetic acid (0.1%). Gradient 1 elution began at 5% B and increased to 100% B over seven minutes. Gradient 2 elution began at 5% B and increased to 100% B over ten minutes. Gradient 3 elution began at 5% B for one minute, increasing to 20% B after the fourth minute, 40% B after the 14$^{th}$ minute and then 100% B after the 15$^{th}$ minute. The columns used were Luna 2 C18 (3µ, 30 mm×4.6 mm), Luna 2 C18 (5µ, 150 mm×2 mm) and a Symmetry Rp8 (3.5µ, 50×2.1 mm).

LC/MS were performed on a PESCIEX single quadrupole API-150EX instrument, equipped with a Luna 2 C18 column (3µ, 30 mm×4.6 mm) eluting with 20% to 100% acetonitrile in water over five minutes.

Example 1

3-(Aminomethyl)benzoyl-D-phenylglycine 2-aminobenzothiazol-6-amide bis(trifluoroacetate) salt 2,6-Diaminobenzothiazole 2-Amino-6-nitrobenzothiazole (500 mg, 2.56 mmol) was dissolved in methanol (20 mL) and 10% palladium on carbon (50 mg) was added as a slurry in methanol (1 mL). The atmosphere was replaced with hydrogen and the suspension was stirred overnight. The catalyst was removed by suction filtration and the solvent evaporated to afford 2,6-diaminobenzothiazole (420 mg, 99%) as a pale yellow solid.

N-BOC-D-Phenylglycine 2-aminobenzothiazol-6-amide

N-BOC-D-Phenylglycine (250 mg, 1.0 mmol), 1-(3-dimethylaminopropyl)-3-ethylcarbodiimide hydrochloride (190 mg, 1.0 mmol) and 7-aza-1-hydroxybenzotriazole (140 mg, 1.0 mmol) were stirred in dimethylformamide (3 mL) for ten minutes. 2,6-Diaminobenzothiazole (160 mg, 1.0 mmol) was then added and the solution was stirred overnight at room temperature. Ethyl acetate (15 mL) was added and the solution was washed with water (5 mL), saturated citric acid solution (5 mL), saturated NaHCO$_3$ (5 mL) and water (5 mL), and dried over MgSO$_4$. The solvent was removed under reduced pressure to afford N-BOC-D-phenylglycine 2-aminobenzothiazol-6-amide.

¹H NMR (CDCl₃): 8.93 (1H, br s, C(O)NHAr); 7.72 (1H, s, benzothiazole C(7)H); 7.35 (2H, br s, Ph); 7.23–7.05 (3H, m, Ph); 6.93 (1H, d, J=10 Hz, benzothiazole C(4)H or C(5)H); 6.72 (1H, d, J=10 Hz, benzothiazole C(4)H or C(5)H); 6.05 (1H, d, J=7 Hz, CHPh); 5.92 (2H, br s, NH₂); 5.45 (1H, br s, BOCNH); 1.27 (9H, s, ᵗBu).

D-Phenylglycine 2-aminobenzothiazol-6-amide

A solution of N-BOC-D-phenylglycine 2-aminobenzothiazol-5amide in dichloromethane (5 mL) was treated with trifluoroacetic acid (5 mL) and stirred for 30 minutes. The dichloromethane and excess trifluoroacetic acid were removed under reduced pressure and the residue was triturated with diethyl ether to afford D-phenylglycine 2-aminobenzothiazol-6-amide as its trifluoroacetate salt (350 mg, 89%).

3-(Aminomethyl)benzoyl-D-phenylglycine 2-aminobenzothiazol-6-amide trifluoroacetate salt N-BOC-3-aminomethylbenzoic acid (250 mg, 1.0 mmol), 1-(3-dimethylaminopropyl)-3-ethylcarbodiimide hydrochloride (190 mg, 1.0 mmol) and 7-aza-1-hydroxybenzotriazole (140 mg, 1.0 mmol) were stirred in dimethylformamide (10 mL) for five minutes. D-Phenylglycine 2-aminobenzothiazol-6-amide trifluoroacetate salt (350 mg, 0.85 mmol) was then added and the mixture was stirred overnight. The solution was poured into ethyl acetate (20 mL) and washed with 5% HCl (5 mL), saturated NaHCO₃ (5 mL) and water (5 mL), dried over MgSO₄ and the solvent removed under reduced pressure. The crude product was purified by flash column chromatography on silica gel (60% ethyl acetate/40% hexane to 100% ethyl acetate) to afford N-BOC-3-(aminomethyl)benzoyl-D-phenylglycine 2-aminobenzothiazol-6-amide. This was dissolved in dichloromethane (5 mL) and trifluoroacetic acid (5 mL) was added. The solution was stirred at room temperature for 30 minutes before the dichloromethane and excess trifluoroacetic acid were removed under reduced pressure. The residue was triturated with diethyl ether to afford 3-(aminomethyl)benzoyl-D-phenylglycine 2-aminobenzothiazol-6-amide as its trifluoroacetate salt (150 mg, 32%).

¹H NMR (d₄ MeOH): 8.21 ppm (1H, s, benzothiazole C(7)H); 7.97 (1H, s, aminomethylbenzoyl C(2)H); 7.94 (1H, d, J=5 Hz, 3-(aminomethyl)benzoyl C(6)H); 7.80–7.48 (5H, m, Ar); 7.47–7.32 (4H, m, Ar); 5.81 (1H, s, CHPh); 4.22 (2H, s, CH₂NH₂).

HPLC (Luna 2, Gradient 1): rt=2.80 minutes.

LC/MS (Luna 2, Gradient 4): rt=1.40 minutes, 432 (MH)⁺.

Examples 2–34 were prepared in the same fashion as Example 1, starting with the indicated nitro-compound or amine. Other functional groups present were protected appropriately.

Example 2

3-(Aminomethyl)benzoyl-D-phenylglycine phenylamide trifluoroacetate salt

Prepared from aniline.

¹H NMR (d₄ MeOH): 7.85 ppm (2H, br s, Ar); 7.49 (6H, m, Ar); 7.27 (5H, m, Ar) 7.01 (1H, t, J=9 Hz, Ar); 5.70 (1H, s, CHPh); 4.12 (2H, s, CH₂NH₂).

HPLC (Luna 2, Gradient 1): rt=3.59 minutes.

LC/MS (Luna 2, Gradient 4): rt=1.99 minutes, 360 (MH)⁺.

Example 3

2-Amino-5-(aminomethyl)benzoyl-D-phenylglycine (1S, 2S, 3S, 5R)-isopinocamphamide dihydrochloride salt Prepared from (1S, 2S, 3S, 5R)-(+)-isopinocampheylamine.

¹H NMR (d4 MeOH): 7.52 ppm (1H, s, Ar—C(6)H); 7.42 (2H, d, J=10, 2×Ph-o-CH); 7.32–7.2 (3H, m, 2×Ph-m-CH, Ph-p-CH); 7.12 (1H, d, J=11 Hz, Ar—C(4)H); 6.67 (1H, d, J=11 Hz, Ar—C(3)H); 5.53 (1H, s, NCH(Ph)); 4.18 (1H, quintet, J=8 Hz, ipc-C(1)H); 3.90 (2H, s, CH₂NH₂); 2.42–2.23 (2H, m, ipc-C(3)H and ipc-(C(2)H); 1.91 (1H, m, ipc-(C)₆H); 1.80 (1H, br s, ipc-(C)₅H); 1.74 (1H, t, J=5 Hz, ipc-(C)₆H); 1.32 (1H, dd, J=14, 8 Hz, ipc-C(7)H); 1.14 (3H, s, ipc-C(8)H₃); 1.02 (3H, d, J=8 Hz, ipc-C(10)H₃); 0.95 (3H, s, ipc-C(9)H₃); 0.87 (1H, d, J=11 Hz, ipc-C(7)H).

HPLC (Luna 2, Gradient 1): rt=4.21 minutes.

LC/MS (Luna 2, Gradient 4): rt=2.10 minutes, 418 (MH-NH₃)⁺.

Example 4

3-(Aminomethyl)benzoyl-D-phenylglycine quinolin-3ylamide trifluoroacetate salt

Prepared from 3-aminoquinoline.

¹H NMR (d₄ MeOH): 9.21 and 8.88 ppm (1H each, s, quinoline C(2)H and C(4)H); 8.10–7.90 (4H, m, Ar); 7.81 (1H, t, J=7 Hz, Ar); 7.77–7.55 (5H, m, Ar); 7.53–7.25 (3H, m, Ar); 5.91 (1H, s, CHPh); 4.20 (2H, s, CH₂NH₂).

HPLC (Luna 2, Gradient 1): rt=2.98 minutes.

LC/MS (Luna 2, Gradient 4): rt=1.83 minutes, 411 (MH)⁺.

Example 5

3-(Aminomethyl)benzoyl-D-phenylglycine 4-(1-piperidyl)phenylamide trifluoroacetate salt Prepared from 4-(1-piperidyl)aniline.

¹H NMR (d₄ MeOH): 7.97 ppm (2H, m, Ar); 7.8 (2H, d, J=9 Hz, Ar); 7.7–7.35 (9H, m, Ar); 5.8 (1H, s, CHPh); 4.2 (2H, s, CH₂NH₂); 3.55 (4H, m, pip); 2.0 (4H, m, pip); 1.8 (2H, m. pip).

HPLC (Luna 2, Gradient 1): rt=2.81 minutes.

LC/MS (Luna 2, Gradient 4): rt=0.59 minutes, 443 (MH)⁺

Example 6

3-(Aminomethyl)benzoyl-D-phenylglycine 1-oxoindan-5-amide trifluoroacetate salt

Prepared from 5-amino-1-oxoindane.

¹H NMR (d₄ MeOH): 7.98 ppm (1H, s, (aminomethyl)benzoyl C(2)H); 7.96 ppm (1H, d, J=10 Hz, (aminomethyl)benzoyl C(6)H); 7.94 (1H, s, indanone C(4)H); 7.70–7.52 (6H, m, Ar); 7.47–7.33 (3H, m, Ar); 5.84 (1H, s, CHPh); 4.22 (2H, s, CH₂NH₂); 3.12 (2H, t, J=5 Hz, indanone C(3)H₂); 2.82–2.75 (2H, m, indanone C(2)H₂).

Example 7

3-(Aminomethyl)benzoyl-D-phenylglycine 3-cyano-4-methylphenyl-amide trifluoroacetate salt Prepared from 3-cyano-4-methylaniline.

$^1$H NMR (d$_4$ MeOH): 8.01 ppm (1H, s, 3-cyano-4-methylphenyl C(2)H); 7.98 (1, s, 3-(aminomethyl)benzoyl C(2)H); 7.94 (1H, d, J=9 Hz, 3-(aminomethyl)benzoyl C(6)H); 7.72–7.52 (5H, m, Ar); 7.48–7.28 (4H, m, Ar); 5.82 (1H, s, CHPh); 4.19 (2H, s, CH$_2$NH$_2$); 2.47 (3H, s, CH$_3$).

HPLC (Luna 2, Gradient 1): rt=3.72 minutes.

LC/MS (Luna 2, Gradient 4): rt=2.05 minutes, 399 (MH)$^+$.

Example 8

3-(Aminomethyl)benzoyl-D-phenylglycine 4-amido phenylamide trifluoroacetate salt Prepared from 4-nitrobenzamide.

$^1$H NMR (d$_4$ MeOH): 8.20–8.05 ppm (2H, m, 3-(aminomethyl)benzoyl C(2)H and C(6)H); 7.97 (2H, d, J=9 Hz, 4-(amidocarbonyl)phenyl C(2)H and C(6)H); 7.86 (2H, d, J=9 Hz, 4-(amidocarbonyl)phenyl C(3)H and C(5)H); 7.82–7.65 (4H, m, Ar); 7.63–7.47 (3H, m, Ar); 6.01, (1H, s, CHPh); 4.32 (2H, br s, CH$_2$NH$_2$).

HPLC (Symmetry C8, Gradient 2): rt=4.84 minutes.

LC/MS (Luna 2, Gradient 4): rt=1.51 minutes, 403 (MH)$^+$.

Example 9

3-(Aminomethyl)benzoyl-D-phenylglycine 3-amidophenylamide trifluoroacetate salt Prepared from 3-nitrobenzamide.

$^1$H NMR (d$_4$ MeOH): 8.30 ppm (1, s, 3-(amidocarbonyl)phenyl C(2)H); 8.17 (1H, s, 3-(aminomethyl)benzoyl C(2)H); 8.12 (1H, d, J=8 Hz, 3-(aminomethyl)benzoyl C(6)H); 7.93 (1H, d, J=7 Hz, 3-(amidocarbonyl)phenyl C(6)H); 7.85–7.68 (5H, m, Ar); 7.65–7.52 (4H, m, Ar); 6.03 (1H, s, CHPh); 4.37 (2H, br s, CH$_2$NH$_2$).

HPLC (Luna 2, Gradient 1): rt=2.95 minutes.

LC/MS (Luna 2, Gradient 4): rt=1.78 minutes, 403 (MH)$^+$.

Example 10

3-(Aminomethyl)benzoyl-D-phenylglycine 1,2,3,4-tetrahydro-1-oxonaphthyl-6-amide trifluoroacetate salt Prepared from 6-amino-1,2,3,4-tetrahydro-1-oxonaphthalene.

$^1$H NMR (d$_4$ MeOH): 7.72 ppm (3H, m, Ar); 7.40 (6H, m, Ar); 7.20 (3H, m, Ar); 5.65 (1H, s, CHPh); 4.02 (2H, s, CH$_2$NH$_2$); 2.78 (2H, t, J=6 Hz, tetrahydronaphthyl C(4)H$_2$); 2.42 (2H, t, J=7 Hz, tetrahydronaphthyl C(2)H$_2$); 1.95 (2H, m, tetrahydronaphthyl C(3)H$_2$).

HPLC (Luna 2, gradient 1): rt=3.57 minutes.

LC/MS (Luna 2, gradient 4): rt=1.88 minutes; 428 (MH)$^+$.

Example 11

3-(Aminomethyl)benzoyl-D-phenylglycine 1,2,3,4-tetrahydro-1-oxonaphthyl-7-amide trifluoroacetate salt Prepared from 7-nitro-1,2,3,4-tetrahydro-1-oxonaphthalene.

$^1$H NMR (d$_4$ MeOH): 8.04 ppm (1H, s, tetrahydronaphthyl C(8)H); 7.82 (2H, dd, J=1, 10 Hz, Ar); 7.60 (2H, dd, Ar); 7.45 (4H, m, Ar); 7.28 (3H, m, Ar); 7.16 (1H, m, Ar); 5.68 (1H, br s, CHPh); 4.03 (2H, s, CH$_2$NH$_2$), 2.83 (2H, t, J=7 Hz, tetrahydronaphthyl C(4)H$_2$); 2.40 (2H, t, J=7 Hz, tetrahydronaphthyl C(2)H$_2$); 2.00 (2H, m, tetrahydronaphthyl C(3)H$_2$).

HPLC (Luna 2, gradient 1): rt=3.65 minutes.

LC/MS (Luna 2, Gradient 4): rt=1.94 minutes, 428 (MH)$^+$.

Example 12

3-(Aminomethyl)benzoyl-D-phenylglycine 1,2,3,4-tetrahydro-naphthyl-6-amide trifluoroacetate salt Prepared from 6-amino-1,2,3,4-tetrahydronaphthalene.

$^1$H NMR (d$_4$ MeOH): 7.72 ppm (1H, s, 3-(aminomethyl) benzoyl C(2)H); 7.70 (1H, d, J=7 Hz, 3-(aminomethyl) benzoyl C(6)H); 7.40 (4H, m, Ar); 7.22 (3H, m, Ar); 7.09 (1H, m, Ar); 6.82 (1H, m, Ar); 5.62 (1H, s, CHPh); 4.00 (2H, s, CH$_2$NH$_2$); 2.50 (4H, s,); 1.58 (4H, s, tetrahydronaphthyl C(4)H$_2$ and C(5)H$_2$).

HPLC (Luna 2, Gradient 4): rt=4.21 minutes.

LC/MS (Luna 2, Gradient 4): rt=2.21 minutes, 414 (MH)$^+$.

Example 13

3-(Aminomethyl)benzoyl-D-phenylglycine 4-(piperazin-1-yl)phenyl-amide bis(trifluoroacetate) salt Prepared from 4-(piperazin-1-yl)aniline.

$^1$H NMR (d$_4$ MeOH): 8.00 ppm (2H, m, Ar); 7.70–7.35 (9H, m, Ar); 7.02 (2H, d, J=10 Hz, Ar); 5.80 (1H, s, CHPh); 4.21 (2H, s, CH$_2$NH$_2$); 3.30 (8H, m, pip).

HPLC (Luna 2, Gradient 1): rt=2.71 minutes.

LC/MS (Luna 2, Gradient 4): rt=0.59 minutes, 444 (MH)$^+$.

Example 14

3-(Aminomethyl)benzoyl-D-phenylglycine 2,3-dihydroindol 5-amide bis(trifluoroacetate) salt Prepared from 2,3-dihydro-5-nitroindole.

$^1$H NMR (d$_4$ MeOH): 7.97 ppm (2H, m, Ar); 7.82 (1H, s, Ar); 7.65 (5H, m, Ar); 7.45 (4H, m, Ar); 5.80 (1H, s, CHPh); 4.20 (2H, s, CH$_2$NH$_2$); 3.85 (2H, t, J=7.5 Hz, dihydroindole C(2)H$_2$); 3.30 (2H, t, J=7.5 Hz, dihydroindole C(3)H$_2$).

HPLC (Luna 2, Gradient 1): rt=2.59 minutes.

LC/MS (Luna 2, Gradient 4): rt=0.59 minutes, 401 (MH)$^+$.

Example 15

3-(Aminomethyl)benzoyl-D-phenylglycine 4-chloro-3-amidophenylamide trifluoroacetate salt Prepared from 2-chloro-5-nitrobenzamide.

$^1$H NMR (d$_4$ MeOH): 7.98 ppm (1, s, 3-(aminomethyl) benzoyl C(2)H); 7.94 (1H, d, J=9 Hz, 3-(aminomethyl) benzoyl C(6)H); 7.83 (1H, s, 2-chloro-3-(amidocarbonyl)-phenyl C(6)H); 7.70–7.50 (5H, m, Ar); 7.45–7.35 (4H, m, Ar); 5.58 (1H, s, CHPh); 4.21 (2H, s, CH$_2$NH$_2$).

HPLC (Luna 2, Gradient 1): rt=3.09 minutes.

LC/MS (Luna 2, Gradient 4): rt=1.62 minutes, 437/439 (MH)$^+$.

Example 16

3-(Aminomethyl)benzoyl-D-phenylglycine 3,5-dichlorophenylamide trifluoroacetate salt Prepared from 3,5-dichloroaniline.

$^1$H NMR (d$_4$ MeOH): 7.98 ppm (1, s, 3-(aminomethyl) benzoyl C(2)H); 7.94 (1H, d, J=9 Hz, 3-(aminomethyl) benzoyl C(6)H); 7.73–7.51 (4H, m, Ar); 7.64 (2H, s, 3,5-dichlorophenyl C(2)H and C(6)H); 7.49–7.32 (3H, m, Ar); 7.18 (1H, s, 3,5-dichlorophenyl C(4)H); 5.80 (1H, s, CHPh); 4.20 (2H, s, CH$_2$NH$_2$).

HPLC (Luna 2, Gradient 1): rt=4.31 minutes.

LC/MS (Luna 2, Gradient 4): rt=2.29 minutes, 428/430/432 (MH)$^+$.

Example 17

3-(Aminomethyl)benzoyl-D-phenylglycine 3-(aminomethyl)phenyl-amide bis(trifluoroacetate) salt Prepared from 3-nitrobenzylamine.

$^1$H NMR (d$_4$ MeOH): 7.97 ppm (2H, m Ar); 7.82 (1H, s, Ar); 7.61 (5H, m, Ar); 7.40 (4H, m, Ar); 7.22 (1H, d, J=11 Hz, Ar); 5.81 (1H, s, CHPh); 4.22 (2H, s, CH$_2$NH$_2$); 4.10 (2H, s, CH$_2$NH$_2$).

HPLC (Luna 2, Gradient 1): rt=2.67 minutes.

LC/MS (Luna 2, Gradient 4): rt=0.59 minutes, 389 (MH)$^+$.

Example 18

3-(Aminomethyl)benzoyl-D-phenylglycine 2,3-dimethylindol-5-amide bis(trifluoroacetate) salt Prepared from 2,3-dimethyl-5-nitroindole.

$^1$H NMR (d$_3$ acetonitrile): 9.12 ppm (1H, br s, NH); 9.08 (1H, bs, NH); 8.40 (1H, d, J=7 Hz, Ar), 8.20 (1H, s, Ar); 8.0 (1H, d, J=7 Hz, Ar); 7.88–7.50 (7H, m, Ar); 7.30 (2H, m, Ar); 6.0 (1H, d, J=6.5 Hz, CHPh); 4.30 (2H, s, CH$_2$NH$_2$); 2.71 (2H, br s, CH$_2$NH$_2$); 2.50 (3H, s, indole C(3)CH$_3$); 2.31 (3H, s, indole C(2)CH$_3$).

HPLC (Luna 2, Gradient 1): rt=3.76 minutes.

LC/MS (Luna 2, Gradient 4): rt=1.99 minutes, 427 (MH)$^+$.

Example 19

3-(Aminomethyl)benzoyl-D-phenylglycine 4-chlorophenylamide trifluoroacetate salt Prepared from 4-chloroaniline.

$^1$H NMR (d$_4$ MeOH): 7.97 ppm (2H, m, Ar); 7.70–7.50 (13H, m, Ar); 5.80 (1H, s, CHPh); 4.21 (2H, s, CH$_2$NH$_2$).

HPLC (Luna 2, Gradient 1): rt=3.95 minutes.

LC/MS (Luna 2, Gradient 4): rt=2.05 minutes, 394 (MH)$^+$.

Example 20

1-[3-(Aminomethyl)benzoyl-D-phenylglycinyl]piperidine trifluoroacetate salt

Prepared from piperidine.

$^1$H NMR (d$_4$ MeOH): 7.97 ppm (2H, m Ar); 7.65–7.30 (7H, m, Ar); 6.10 (1H, s, CHPh); 4.21 (2H, s, CH$_2$NH$_2$); 3.79 (1H, m, pip); 3.50 (3H, m, pip); 1.70–1.21 (5H, m, pip).

HPLC (Luna 2, Gradient 1): rt=3.36 minutes.

LC/MS (Luna 2, Gradient 4): rt=1.78 minutes, 394 (MH)$^+$.

Example 21

1-[3-(Aminomethyl)benzoyl-D-phenylglycinyl]-3-[(N-ethyl-N-methyl)amido]piperidine trifluoroacetate salt Prepared from 3-[(N-ethyl-N-methyl)amidocarbonyl]-piperidine.

$^1$H NMR (CD$_3$CN): The compound contains two chiral centres and is therefore a mixture of diastereomers, as well as exhibiting rotamers due to the N-ethyl-N-methyl amide. 8.45–7.78 ppm (5H, m, Ar and NH); 7.72–7.28 (5H, m, Ph); 6.10–5.90 (1H, m, CHPh); 4.61–4.35 (1H, m, piperidine H); 4.14 (2H, br s, CH$_2$NH$_2$); 3.97–3.66 (1H, m, piperidine H); 3.50–2.35 (12H, m) 1.90–0.75 (4H, m).

HPLC (Luna 2, Gradient 1): rt=3.13 minutes.

LC/MS (Luna 2, Gradient 4): rt=1.72 minutes, 437 (MH)$^+$.

Example 22

1-[3-(Aminomethyl)benzoyl-D-phenylglycinyl]pyrrolidine trifluoroacetate salt Prepared from pyrrolidine.

$^1$H NMR (d$_4$ MeOH): 7.95 ppm (2H, m, Ar); 7.72–7.34 (7H, m, Ar); 5.91 (1H, m, CHPh); 4.20 (2H, s, CH$_2$NH$_2$); 3.80 (2H, m, pyr); 3.61 (2H, m, pyr); 3.50 (2H, m, pyr); 3.19 (2H, m, pyr).

HPLC (Luna 2, Gradient 1): rt=3.06 minutes.

LC/MS (Luna 2, Gradient 4): rt=0.57 minutes, 338 (MH)$^+$.

Example 23

2-[3-(Aminomethyl)benzoyl-D-phenylglycinyl] decahydroisoquinoline trifluoroacetate salt Prepared from decahydroisoquinoline.

$^1$H NMR (d$_4$ MeOH): 7.70 ppm (2H, br s, Ar); 7.41–7.09 (7H, m, Ar); 5.95–5.78 (1H, m, CHPh); 3.95 (2H, s, CH$_2$NH$_2$); 1.7–0.65 (16H, m, decahydroisoquinoline C(H)'s).

HPLC (Luna 2, Gradient 1): rt=4.11 minutes.

LC/MS (Luna 2, Gradient 4): rt=2.15 minutes, 406 (MH)+.

Example 24

3-(Aminomethyl)benzoyl-D-phenylglycine 2,3-dihydroindol-6-amide trifluoroacetate salt Prepared from 2,3-dihydro-6-nitroindole.

$^1$H NMR (d$_4$ MeOH): 7.91 ppm (2H, m, Ar); 7.75 (1H, s, Ar); 7.57 (4H, m, Ar); 7.34 (5H, m, Ar); 5.75 (1H, s, C$\underline{H}$Ph); 4.15 (2H, s, C$\underline{H}_2$NH$_2$); 3.75 (2H, t, J=7.5 Hz, dihydroindole C(2)H$_2$); 3.20 (2H, t, J=7.5 Hz, dihydroindole C(3)H$_2$).

HPLC (Luna 2, Gradient 1): rt=2.54 minutes.

LC/MS (Luna 2, Gradient 4): rt=1.24 minutes, 401 (MH)+.

Example 25

3-(Aminomethyl)benzoyl-D-phenylglycine 2,3-dihydroindolamide trifluoroacetate salt Prepared from 2,3-dihydroindole.

$^1$H NMR (d$_4$ MeOH): 8.92 ppm (1H, d, J=7 Hz, NH); 8.22 (1H, d, J=9.5 Hz, dihydroindole C(7)H); 7.97 (2H, m, Ar); 7.48 (3H, m, Ar); 7.19 (2H, m, Ar); 7.08 (1H, m, Ar); 6.02 (1H, m, C$\underline{H}$Ph); 4.41 (1H, m, dihydroindole C(2)H); 4.19 (2H, s, C$\underline{H}_2$NH$_2$); 3.78 (1H, m, dihydroindole C(2)H); 3.23 (1H, m, dihydroindole C(3)H); 3.07 (1H, m, dihydroindole C(3)H).

HPLC (Luna 2, Gradient 1): rt=3.79 minutes.

LC/MS (Luna 2, gradient 4): rt=2.21 minutes, 386 (MH)+.

Example 26

3-(Aminomethyl)benzoyl-D-phenylglycine 1-methyl-2,3-dihydro-indol-6-amide bis(trifluoracetate salt)

Prepared from 6-amino-2,3-dihydro-1-methylindole.

$^1$H NMR (d$_4$ MeOH): 8.0 ppm (2H, m, Ar); 7.65 (4H, m, Ar); 7.40 (3H, m, Ar); 7.15 (2H, m, Ar); 6.95 (1H, m, Ar); 5.83 (1H, s, C$\underline{H}$Ph); 4.20 (2H, s, C$\underline{H}_2$NH$_2$); 3.42 (2H, m, dihydroindole C(2)H); 2.98 (2H, m, dihydroindole C(3)H); 2.82 (3H, s, NCH$_3$).

HPLC (Luna 2, Gradient 1): rt=2.80 minutes.

LC/MS (Luna 2, Gradient 4): rt=1.88 minutes, 415 (MH)+.

Example 27

3-(Aminomethyl)benzoyl-D-phenylglycine 3-acetylamino-4-methylphenylamide trifluoroacetate salt Prepared from 2-methyl-5-nitroacetanilide.

$^1$H NMR (D$_2$O): 7.78–7.19 (12H, m, Ar), 5.64 (1H, s, α-C$\underline{H}$), 4.17 (2H, s, C$\underline{H}_2$NH$_2$), 2.12 (6H, s, 2×C$\underline{H}_3$)

HPLC (Luna 2, Gradient 1): rt=3.10 minutes.

LC/MS (Luna 2, Gradient 4): rt=1.56 minutes, 431 (MH+).

Example 28

3-(Aminomethyl)benzoyl-D-phenylglycine (R/S)-8-methyl-5,6,7,8-tetrahydronaphth-2-ylamide trifluoroacetate salt Prepared from (R/S)-8-methyl-5,6,7,8-tetrahydronaphth-2-ylamine, synthesised as described below.

(R/S)-8-methyl-5,6,7,8-tetrahydronaphth-2-ylamine

A suspension of methyltriphenylphosphonium iodide (680 mg, 1.68 mmol) in tetrahydrofuran (7 mL) was cooled to −45° C. n-Butyllithium (1.0 mL, 1.6 M in hexane, 1.60 mmol) was then added dropwise, and the solution was stirred for 1 hour. 1,2,3,4-Tetrahydro-7-nitro-1-oxonaphthalene (200 mg, 1.05 mmol) in tetrahydrofuran (3 mL) was then added over 5 minutes.

The reaction mixture was allowed to warm to room temperature before being quenched with water (20 mL). The solution was then extracted with dichloromethane (2×25 mL), the solvent was dried (MgSO$_4$) and concentrated under reduced pressure to give a black oil. The crude product was then purified by flash chromatography (ethyl acetate/hexane; 1:40) to afford 5,6,7,8-tetrahydro-8-methylene-2-nitronaphthalene as a white solid (150 mg, 76%).

A solution of the olefin (100 mg, 0.53 mmol) in methanol (2 mL) was stirred over 10% palladium on carbon (20 mg). The mixture was purged with hydrogen and stirred for 18 hrs under a balloon of hydrogen. The reaction mixture was then filtered through celite, washing with additional methanol, and concentrated under reduced pressure to afford (R/S)-8-methyl-5,6,7,8-tetrahydronaphth-2-ylamine as a colourless oil (75 mg, 82%).

$^1$H NMR (CDCl$_3$): 7.53 ppm (1H, d, J=8 Hz, C(4)H); 7.21 (1H, d, J=2 Hz, C(1)H); 7.18 (1H, dd, J=8, 2 Hz, C(3)H); 4.16 (2H, br s, NH$_2$); 3.52 (1H, sextet, J=7 Hz, C$\underline{H}$CH$_3$); 3.41–3.25 (2H, m, C(5)H$_2$); 2.61–2.45 (2H, m, tetrahydronaphthalene C(6)H and/or C(7)H); 2.43–2.32 (1H, m, tetrahydronaphthalene C(6) or C(7)H); 2.23–2.12 (1H, m, tetrahydronaphthalene C(6)H or C(7)H); 1.96 (3H, d, J=7 Hz, CH$_3$).

3-(Aminomethyl)benzoyl-D-phenylglycine (R/S)-8-methyl-5,6,7,8-tetrahydro-naphth-2-ylamide trifluoroacetate salt $^1$H NMR (MeOH): 7.95 ppm (2H, br s, Ar); 7.76–7.60 (4H, m, Ar); 7.48–7.31 (4H, m, Ar); 7.29–7.21 (1H, m, Ar); 6.97 (1H, d, J=8 Hz, Ar); 5.80 (1H, s, C$\underline{H}$Ph); 4.18 (2H, s, C$\underline{H}_2$NH$_2$); 2.90–2.69 (3H, m, tetrahydronaphthalene C(5)H and C(8)H$_2$); 1.99–1.80 (2H, m, tetrahydronaphthalene C(6)H and/or C(7)H); 1.75–1.63 (1H, m, tetrahydronaphthalene C(6) or C(7)H); 1.58–1.40 (1H, m, tetrahydronaphthalene C(6)H or C(7)H); 1.27 (3H, d, J=7 Hz, CH$_3$).

HPLC (Symmetry, Gradient 2): rt=6.73 minutes.

LC/MS (Luna 2, Gradient 4): rt=2.53 minutes, 428 (MH)+.

Example 29

3-(Aminomethyl)benzoyl-D-phenylglycine indan-5-ylamide trifluoroacetate salt

Prepared from 5-aminoindane.

$^1$H NMR (d$_4$ MeOH): 8.16 ppm (1H, s, 3-(aminomethyl)benzoyl C(2)H); 8.15 (1H, m, 3-(aminomethyl)benzoyl C(6)

H); 7.96–7.54 (8H, m, Ar); 7.45 (1H, d, J=8 Hz, indane C(6)H or C(7)H); 7.33 (1H, d, J=8 Hz, indane C(6)H or C(7)H); 6.0 (1H, s, C$\underline{\text{H}}$Ph); 4.39 (2H, s, C$\underline{\text{H}}_2$NH$_2$); 3.06 (4H, q, J=7 Hz, indane C(1)H$_2$ and C(3)H$_2$); 2.26 (2H, quintet, J=7 Hz, indane C(2)H$_2$).

HPLC (Luna 2, Gradient 1): rt=4.02 minutes.

LC/MS (Luna 2, Gradient 4): rt=2.42 minutes, 400 (MH)$^+$.

Example 30

3-(Aminomethyl)benzoyl-D-phenylglycine 4-isopropylphenylamide trifluoroacetate salt Prepared from 4-isopropylaniline.

$^1$H NMR (d$_4$ MeOH): 8.17 ppm (1H, s, 3-(aminomethyl) benzoyl C(2)H); 8.15 (1H, m, 3-(aminomethyl)benzoyl C(6) H); 7.83–7.59 (9H, m, Ar); 7.38 (2H, d, J=8.5 Hz, Ar); 6.0 (1H, s, C$\underline{\text{H}}$Ph); 4.38 (2H, s, C$\underline{\text{H}}_2$NH$_2$); 3.09 (1H, septet, J=7 Hz, C$\underline{\text{H}}$(CH$_3$)$_2$); 1.42 (6H, d, J=7 Hz, CH(C$\underline{\text{H}}_3$)$_2$).

HPLC (Luna 2, Gradient 1): rt=4.21 minutes.

LC/MS (Luna 2, Gradient 4): rt=2.48 minutes, 402 (MH)$^+$.

Example 31

3-(Aminomethyl)benzoyl-D-phenylglycine (1S, 2S, 3S, 5R)-isopinocamphamide trifluoroacetate salt Prepared from (1S, 2S, 3S, 5R)-(+)-isopinocamphey-lamine.

$^1$H NMR (d$_4$ MeOH): 7.96 ppm (1H, s, 3-(aminomethyl) benzoyl C(2)H); 7.95 (1H, m, 3-(aminomethyl)benzoyl C(6) H); 7.67–7.25 (7H, m, Ar); 5.70 (1H, s, C$\underline{\text{H}}$Ph); 4.28 (1H, m, isopinocampheyl C(1)H); 4.20 (2H, s, C$\underline{\text{H}}_2$NH$_2$); 2.55–1.77 (5H, m, isopinocampheyl H's); 1.26 (3H, s, CH$_3$); 1.14 (3H, d, J=7 Hz, isopinocampheyl C(10)H$_3$); 1.08 (3H, s, CH$_3$); 1.04–0.94 (2H, m, isopinocampheyl H's).

HPLC (Luna 2, Gradient 1): rt=4.34 minutes.

LC/MS (Luna 2, Gradient 4): rt=2.34 minutes, 420 (MH)$^+$.

Example 32

3-(Aminomethyl)benzoyl-D-phenylglycine 4-(1-hydroxyethyl)phenylamide trifluoroacetate salt Prepared from 1-(4-aminophenyl)ethanol.

$^1$H NMR (d$_4$ MeOH): 7.85 ppm (1H, s, 3-(aminomethyl) benzoyl C(2)H); 7.84 (1H, m, 3-(aminomethyl)benzoyl C(6) H); 7.56–7.05 (11H, m, Ar); 5.72 (1H, s, C$\underline{\text{H}}$Ph); 4.69 (1H, q, J=6.5 Hz, C$\underline{\text{H}}$(OH)CH$_3$); 4.08 (2H, s, C$\underline{\text{H}}_2$NH$_2$); 1.31 (3H, d, J=6.5 Hz, CH$_3$).

HPLC (Luna 2, Gradient 1): rt=3.0 minutes.

LC/MS (Luna 2, Gradient 4): rt=1.83 minutes, 404 (MH)$^+$.

Example 33

3-(Aminomethyl)benzoyl-D-phenylglycine cis-2-aminocyclohexyl-amide bis(trifluoroacetate) salt Prepared from cis-1,2-diaminocyclohexane.

$^1$H NMR (d$_4$ MeOH): 8.08 ppm (1H, s, 3-(aminomethyl) benzoyl C(2)H); 8.06 (1H, m, 3-(aminomethyl)benzoyl C(6) H); 7.79–7.48 (7H, m, Ar); 5.87 (1H, s, C$\underline{\text{H}}$Ph); 4.46 (1H, m, cyclohexyl C(1)H); 4.30 (2H, s, C$\underline{\text{H}}_2$NH$_2$); 3.54 (1H, m, cyclohexyl C(2)H); 2.11–1.52 (8H, m, cyclohexyl H's).

HPLC (Luna 2, Gradient 1); rt=2.40 minutes.

LC/MS (Luna 2, Gradient 4): rt=1.08 minutes, 381 (MH)$^+$.

Example 34

1-[3-(Aminomethyl)benzoyl-D-phenylglycinyl]4-hydroxypiperidine hydrochloride salt Prepared from 4-hydroxypiperidine.

$^1$H NMR (d$_4$ MeOH): 7.84 ppm (1H, s, 3-(aminomethyl) benzoyl C(2)H); 7.80 (1H, m, 3-(aminomethyl)benzoyl C(6) H); 7.59–7.17 (7H, m, Ar); 6.03 (1H, s, C$\underline{\text{H}}$Ph); 4.11 (2H, s, C$\underline{\text{H}}_2$NH$_2$); 3.90 (1H, m, piperidyl C(4)H); 3.62 (2H, m, piperidyl C(2)H and C(6)H); 3.14–2.94 (2H, m, piperidyl C(2)H and C(6)H); 1.93–1.16 (4H, m, piperidyl C(3)H$_2$ and C(5)H$_2$).

HPLC (Luna 2, Gradient 1): rt=2.56 minutes.

LC/MS (Luna 2, Gradient 4): rt=1.36 minutes, 368 (MH)$^+$.

Example 35

3-(Aminomethyl)benzoyl-D-phenylglycine 1-acetyl-2,3-dihydro-indol-6-amide trifluoroacetate salt 1-Benzyloxycarbonyl-2,3-dihydro-6-nitroindole A solution of 6-nitroindoline (10.0 g, 0.061 mol), triethylamine (22.7 mL, 0.16 mol) and dimethylaminopyridine (50 mg, cat.) in dichloromethane (130 mL) was stirred at 0° C. and benzyl chloroformate (18 mL, 0.12 mol) was added slowly. The mixture was allowed to warm to room temperature overnight. The mixture was washed with water (50 mL), 5% aqueous HCl (100 mL), saturated aqueous NaHCO$_3$ (50 mL) and water (50 mL). The dichloromethane was dried (MgSO$_4$) and evaporated under reduced pressure to give an orange solid. This was triturated in diethyl ether (150 ml) to give a yellow solid (12.34 g, 68%).

$^1$H NMR (CDCl$_3$): 7.80 ppm (1H, dd, J=8, 2 Hz, C(7)H); 7.35 (5H, m, Ph); 7.20 (2H, m, C(4)H and C(5)H); 5.25 (2H, br s, C$\underline{\text{H}}_2$Ph); 4.11 (2H, t, J=8 Hz, dihydroindole C(2)H$_2$); 3.15 (2H, t, J=8 Hz, dihydroindole C(3)H$_2$).

6-amino-1-benzyloxycarbonyl-2,3-dihydroindole

A mixture of 1-benzyloxycarbonyl-2,3-dihydro-6-nitroindole (1.0 g, 3.36 mmol) and tin(II) chloride dihydrate (3.78 g, 16.75 mmol) in ethanol (70 mL) was heated at 70° C., under an atmosphere of nitrogen, for 3 hours. The solution was cooled and the solvent evaporated under reduced pressure to give an off-white solid. The solid was partitioned between water (50 mL) and ethyl acetate (100 mL) and the aqueous layer basified (pH 11) with 1M sodium hydroxide solution. The mixture was filtered to remove tin salts and the ethyl acetate was separated, dried (MgSO$_4$) and evaporated under reduced pressure to give the amine as a yellow oil (0.89 g, 99%).

$^1$H NMR (CDCl$_3$): 7.51–7.33 ppm (6H, m, Ph+C(7)H); 6.93 (1H, d, J=8 Hz, C(4)H); 6.32 (1H, dd, J=8, 2 Hz, C(5)H); 5.28 (2H, br s, C$\underline{\text{H}}_2$Ph); 4.01 (2H, t, J=7.5 Hz, dihydroindole C(2)H$_2$); 3.66 (2H, bs, NH$_2$); 3.05 (2H, t, J=7.5 Hz, dihydroindole C(3)H$_2$).

N-BOC-D-phenylglycine 1-benzyloxycarbonyl-2,3-dihydroindol-6-amide

A solution of N-BOC-D-phenylglycine (0.83 g, 3.28 mmol), 1-[3-(dimethyl-amino)propyl]-3-ethylcarbodiimide hydrochloride (0.75 g, 3.9 mmol), 1-hydroxy-7-azabenzotriazole (0.54 g, 3.9 mmol) and 4-(N,N-dimethylamino)pyridine (10 mg, cat.) in dimethylformamide (20 mL) was stirred at room temperature and a solution of the above amine (0.88 g, 3.28 mmol) in dimethylformamide (20 mL) was added and the mixture allowed to stir overnight. The dimethylformamide was evaporated under reduced pressure and the resulting oil partitioned between water (50 mL) and ethyl acetate (50 mL). The ethyl acetate was washed with 5% aqueous HCl (10 mL) and saturated aqueous NaHCO$_3$ (10 mL), dried (MgSO$_4$) and evaporated under reduced pressure to give the amide as a golden foam (1.6 g, 97%).

$^1$H NMR (CDCl$_3$): 7.43–7.10 ppm (13H, m, Ar): 6.85 (1H, d, J=6 Hz, NH); 5.61 (1H, br s, NH); 5.03 (2H, br s, CH$_2$Ph); 3.85 (2H, t, J=7 Hz, dihydroindole C(2)H$_2$); 2.85 (2H, t, J=8 Hz, dihydroindole C(3)H$_2$); 1.19 (9H, s, $^t$Bu).

D-phenylglycine 1-benzyloxycarbonyl-2,3-dihydroindol-6-amide trifluoroacetate salt Trifluoroacetic acid (5 mL) was added to a solution of the above foam in dichloromethane (20 mL) and the solution was allowed to stir for 2 hours at room temperature. The solvent was evaporated under reduced pressure to give the amine trifluoracetate salt as a red foam (1.5 g, 91%) which was used without further purification.

3-(N-BOC-Aminomethyl)benzoyl-D-phenylglycine (1-benzyloxycarbonyl-2,3-dihydro)-indol-6-amide A solution of 3-(N-BOC-aminomethyl)benzoic acid (0.798 g, 3.2 mmol), 1-[3-(dimethylamino)propyl]-3-ethylcarbodiimide hydrochloride (0.73 g, 3.8 mmol), 1-hydroxy-7-azabenzotriazole (0.52 g, 3.8 mmol) and triethylamine (1.0 mL, 7.2 mmol) in dimethylformamide (10 mL) was stirred at room temperature and a solution of the above amine (1.5 g, 3.0 mmol) in dimethylformamide (5 mL) was added. The mixture was stirred overnight before the dimethylformamide was evaporated under reduced pressure, and the resulting oil partitioned between water (50 mL) and ethyl acetate (50 mL). The ethyl acetate layer was washed with 5% aqueous HCl (10 mL) and saturated aqueous NaHCO$_3$ (10 mL), dried (MgSO$_4$) and evaporated under reduced pressure to give a yellow solid.

$^1$H NMR (CDCl$_3$): 7.75–7.22 ppm (17H, m, Ar): 7.05 (1H, d, J=5.5 Hz, NH); 5.74 (1H, d, J=6 Hz, CHPh); 5.21 (2H, s, OCH$_2$Ph); 4.89 (1H, br s, NH); 4.32 (2H, d, J=6 Hz, CH$_2$NHBOC); 4.02 (2H, t, J=8 Hz, dihydroindole C(2)H$_2$); 3.05 (2H, t, J=8 Hz, dihydroindole C(3)H$_2$); 1.4 (9H, s, $^t$Bu).

3-(N-BOC-Aminomethyl)benzoyl-D-phenylglycine 2,3-dihydroindol-6-amide

A solution of the above solid in methanol (50 mL) was stirred over 10% Pd/C (500 mg) under an atmosphere of H$_2$ and heated under reflux for 2 hours. The mixture was cooled, filtered and the solvent evaporated under reduced pressure to provide the unprotected dihydroindole as a yellow foam (1.4 g, 88%) which was used without further purification.

3-(Aminomethyl)benzoyl-D-phenylglycine 1-acetyl-2,3-dihydroindol-6-amide trifluoroacetate salt A solution of the dihydroindole (500 mg, 1.0 mmol) and triethylamine (0.28 mL, 2 mmol) in dichloromethane (20 mL) was stirred at 0° C. and acetyl chloride (86 mg, 1.1 mmol) was added dropwise, then left to stir overnight. The mixture was washed with 5% aqueous HCl (10 mL) and the organic phase was dried (MgSO$_4$) and evaporated. The residue was purified by flash column chromatography (ethyl acetate/hexane, 1:1) to give a yellow oil. The oil was dissolved in dichloromethane (20 mL) and treated with trifluoroacetic aid (5 mL). After stirring for 2 hours the solvent was evaporated under redued pressure to an oil, which after triturating with diethyl ether gave the amine as its trifluoroacetate salt as a white solid (337 mg, 61%).

$^1$H NMR (d$_4$ MeOH): 8.30 ppm (1H, s, Ar); 7.97 (2H, m, Ar); 7.60 (4H, m, Ar); 7.39 (4H, 3, m, Ar); 7.22 (1H, d, J=10 Hz, Ar); 5.82 (1H, s, CHPh); 4.2 (2H, s, CH$_2$NH$_2$); 4.15 (2H, t, J=7 Hz, dihydroindole C(2)H$_2$); 3.17 (2H, t, J=7 Hz, dihydroindole C(3)H$_2$); 2.25 (3H, s, CH$_3$).

HPLC (Luna 2, Gradient 1): rt=3.39 minutes.

LC/MS (Luna 2, Gradient 4): rt=1.72 minutes, 443 (MH)$^+$.

Examples 36–60 were prepared from the intermediate 3-(N-BOC-aminomethyl)-benzoyl-D-phenylglycine 2,3-dihydroindol-5-amide, described for Example 29, and the appropriate carboxylic acid or derivative, using standard chemical methods and protecting other functionality where required.

Example 36

3-(Aminomethyl)benzoyl-D-phenylglycine 1-propanoyl-2,3-dihydro-indol-6-amide trifluoroacetate salt Prepared using propanoyl chloride.

$^1$H NMR (d$_4$ MeOH): 8.58 ppm (1H, d, J=1.2 Hz, dihydroindole C(7)H); 8.18 (2H, m, Ar); 7.82 (4H, m, Ar); 7.59 (4H, m, Ar); 7.37 (1H, m, Ar); 6.03 (1H, s, CHPh); 4.39 (2H, s, CH$_2$NH$_2$); 4.31 (2H, t, J=9 Hz, dihydroindole C(2)H); 3.37 (2H, t, J=9 Hz, dihydroindole C(3)H); 2.73 (2H, q, J=7.5 Hz, CH$_2$CH$_3$); 1.47 (3H, t, J=7.5 Hz, CH$_2$CH$_3$).

HPLC (Luna 2, Gradient 1): rt=3.55 minutes.

LC/MS (Luna 2, Gradient 4): rt=1.94 minutes, 457 (MH)$^+$.

Example 37

3-(Aminomethyl)benzoyl-D-phenylglycine 1-(2-methyl-propanoyl)-2,3-dihydroindol-6-amide trifluoroacetate salt Prepared using 2-methylpropanoyl chloride.

$^1$H NMR (d$_4$ MeOH): 8.32 ppm (1H, s, dihydroindole C(7)H); 7.98 (2H, m, Ar); 7.60 (4H, m, Ar); 7.43 (4H, m, Ar); 7.18 (1H, m, Ar); 5.83 (1H, s, CHPh); 4.21 (4H, m, CH$_2$NH$_2$ and dihydroindole C(2)H); 3.18 (2H, t, J=9 Hz, dihydroindole C(3)H), 2.95 (1H, m, CH(CH$_3$)$_2$); 1.22 (6H, d, J=8 Hz, CH(CH$_3$)$_2$).

HPLC (Luna 2, Gradient 1): rt=3.74 minutes.

LC/MS (Luna 2, Gradient 4): rt=2.05 minutes, 471 (MH)$^+$.

Example 38

3-(Aminomethyl)benzoyl-D-phenylglycine 1-D-alaninoyl-2,3-dihydroindol-6-amide bis(trifluoroacetate) salt Prepared using D-alanine.

$^1$H NMR (d$_4$ MeOH): 8.40 ppm (1H, s, Ar); 8.01 (2H, m, Ar); 7.65 (4H, m, Ar); 7.45 (4H, m, Ar); 7.25 (1H, d, J=10 Hz, Ar); 5.85 (1H, s, CHPh); 4.4 (1H, q, J=0.7 Hz, alaninyl CHNH$_2$); 4.25 (2H, s, ArCH$_2$NH$_2$); 4.25 (2H, t, J=8 Hz, dihydroindole C(2)H$_2$); 3.28 (2H, t, J=8 Hz, dihydroindole C(3)H$_2$); 1.65 (3H, d, J=7 Hz, CH$_3$).

HPLC (Luna 2, Gradient 1): rt=2.85 minutes.

LC/MS (Luna 2, Gradient 4): rt=1.35 minutes, 472 (MH)$^+$.

Example 39

3-(Aminomethyl)benzoyl-D-phenylglycine 1-L-alaninoyl-2,3-dihydroindol-6-amide bis(trifluoroacetate) salt Prepared using L-alanine.

$^1$H NMR (d$_4$ MeOH): 8.43 ppm (1H, s, Ar); 7.97 (2H, m, Ar); 7.63 (4H, m, Ar); 7.45 (4H, m, Ar); 7.25 (1H, d, J=10 Hz, Ar); 5.85 (1H, s, CHPh); 4.35 (1H, q, J=7 Hz, alaninyl CHNH$_2$); 4.25 (2H, t, J=7.5 Hz, indoline C(2)H$_2$); 4.2 (2H, s, CH$_2$NH$_2$); 3.25 (2H, t, J=8 Hz, indoline C(3)H$_2$); 1.6 (3H, d, J=7 Hz, CH$_3$).

HPLC (Luna 2, Gradient 1): rt=2.84 minutes.

LC/MS (Luna 2, Gradient 4): rt=0.59 minutes, 472 (MH)$^+$.

Example 40

3-(Aminomethyl)benzoyl-D-phenylglycine 1-(N-acetyl-D-alaninoyl)-2,3-dihydroindol-6-amide trifluoroacetate salt Prepared using N-acetyl-D-alanine.

$^1$H NMR (d$_4$ MeOH): 8.33 ppm (1H, s, Ar); 7.97 (2H, m, Ar); 7.61 (4H, m, Ar); 7.40 (4H, m, Ar); 7.18 (1H, d, J=9 Hz, Ar); 5.83 (1H, s, CHPh); 4.70 (1H, br m, CHNHAc); 4.38 (1H, m, indoline C(2)H); 4.21 (2H, s, CH$_2$NH$_2$); 4.20 (1H, t, J=8 Hz indoline C(2)H); 3.2 (2H, t, J=8 Hz, indoline C(3)H$_2$); 2.01 (3H, s, COCH$_3$); 1.4 (3H, d, J=7 Hz, CH$_3$).

HPLC (Luna 2, Gradient 1): rt=3.24 minutes.

LC/MS (Luna 2, Gradient 4): rt=0.59 minutes, 514 (MH)$^+$.

Example 41

3-(Aminomethyl)benzoyl-D-phenylglycine 1-(N-acetyl-L-alaninoyl)-2,3-dihydroindol-6-amide trifluoroacetate salt Prepared using N-acetyl-L-alanine.

$^1$H NMR (d$_4$ MeOH): 8.33 ppm (1H, s, Ar); 7.97 (2H, m, Ar); 7.62 (4H, m, Ar); 7.38 (4H, m, Ar); 7.18 (1H, d, Ar); 5.83 (1H, s, CHPh); 4.70 (1H, m, CHNHAc); 4.35 (1H, m, dihydroindole C(2)H); 4.2 (2H, s, CH$_2$NH$_2$); 4.2 (1H, m, dihydroindole C(2)H); 3.2 (2H, t, J=8 Hz, dihydroindole C(3)H$_2$); 2.0 (3H, s, COCH$_3$); 1.4 (3H, d, J=7 Hz, CH$_3$).

HPLC (Luna 2, Gradient 1): rt=3.19 minutes.

LC/MS (Luna 2, Gradient 4): rt=1.67 minutes, 514 (MH)$^+$.

Example 42

3-(Aminomethyl)benzoyl-D-phenylglycine 1-aminoacetyl-2,3-dihydroindol-6-amide bis(trifluoroacetate) salt Prepared using glycine.

$^1$H NMR (d$_4$ MeOH): 8.41 (1H, s, dihydroindole C(7)H); 7.97 (2H, br s, Ar); 7.58 (4H, m, Ar); 7.22 (1H, d, J=8 Hz, Ar); 5.84 (1H, s, CHPh); 4.20 (2H, s, CH$_2$NH$_2$); 4.15 (2H, t, J=9 Hz, dihydroindole C(2)H); 4.04 (2H, s, COCH$_2$NH$_2$); 3.23 (2H, t, J=9 Hz, dihydroindole C(3)H).

HPLC (Luna 2, Gradient 1): rt=2.77 minutes.

LC/MS (Luna 2, Gradient 4): rt=1.24 minutes, 458 (MH)$^+$.

Example 43

3-(Aminomethyl)benzoyl-D-phenylglycine 1-(3-methylbutanoyl)-2,3-dihydroindol-6-amide trifluoroacetate salt Prepared using 3-methylbutanoyl chloride.

$^1$H NMR (d$_4$ MeOH): 8.40 ppm (1H, s, Ar); 8.02 (2H, m, Ar); 7.67 (4H, m, Ar); 7.22 (1H, d, J=11 Hz, Ar); 5.90 (1H, s, CHPh); 4.27 (2H, s, CH$_2$NH$_2$); 4.22 (2H, t, J=8 Hz, indoline C(2)H$_2$); 3.22 (2H, t, J=8 Hz, indoline C(3)H$_2$); 2.45 (2H, d, J=7 Hz, COCH$_2$); 2.28 (1H, septet, J=7 Hz, CHMe$_2$); 1.1 (6H, d, J=7 Hz, CH(CH$_3$)$_2$).

HPLC (Luna 2, Gradient 1): rt=4.18 minutes.

LC/MS (Luna 2, Gradient 4): rt=2.15 minutes, 485 (MH)$^+$.

Example 44

3-(Aminomethyl)benzoyl-D-phenylglycine 1-(benzyloxy)-acetyl-2,3-dihydroindol-6-amide trifluoroacetate salt Prepared using 2-benzyloxyacetyl chloride.

$^1$H NMR (d$_4$ MeOH): 8.40 ppm (1H, s, Ar); 8.02 (2H, m, Ar); 7.65 (5H, m, Ar); 7.45 (10H, m, Ar); 7.22 (1H, d, J=10 Hz, Ar); 5.91 (1H, s, CHPh); 4.73 (2H, s, COCH); 4.35 (1H, q, CHNH$_2$); 4.37 (2H, s, CH$_2$Ph); 4.25 (2H, s, CH$_2$NH$_2$); 4.12 (2H, t, J=7.5 Hz, indoline C(2)H$_2$); 3.2 (2H, t, J=7.5 Hz, indoline C(3)H$_2$).

HPLC (Luna 2, Gradient 1): rt=4.25 minutes.

LC/MS (Luna 2, Gradient 4): rt=2.15 minutes, 549 (MH)$^+$.

Example 45

3-(Aminomethyl)benzoyl-D-phenylglycine 1-L-threoninoyl-2,3-dihydroindol-6-amide bis(trifluoroacetate) salt Prepared using L-threonine.

$^1$H NMR (d$_4$ MeOH): 8.31 ppm (1H, s, Ar); 7.80 (2H, m, Ar); 7.45 (4H, m, Ar); 7.25 (4H, m, Ar); 7.05 (1H, d, Ar); 5.65 (1H, s, CHPh); 4.10 (2H, t, J=8 Hz, indoline C(2)H$_2$); 4.02 (2H, s, CH$_2$NH$_2$); 3.11 (2H, t, J=8 Hz, indoline C(3)H$_2$); 1.21 (3H, d, CH$_3$); other signals obscured by solvent.

HPLC (Luna 2, Gradient 1): rt=2.84 minutes.

LC/MS (Luna 2, Gradient 4): rt=0.65 minutes, 502 (MH)$^+$.

Example 46

3-(Aminomethyl)benzoyl-D-phenylglycine 1-L-prolinoyl-2,3-dihydroindol-6-amide bis(trifluoroacetate) salt Prepared using L-proline.

$^1$H NMR (d$_4$ MeOH): 8.47 ppm (1H, s, Ar); 8.05 (2H, m, Ar); 7.75–7.65 (4H, m, Ar); 7.56–7.47 (4H, m, Ar); 7.30 (1H, d, J=9 Hz, Ar); 5.91 (1H, s, CHPh); 4.73 (1H, t, J=6.5 Hz, proline C(2)H); 4.25 (4H, m, CH$_2$NH$_2$ and indoline C(2)H$_2$); 3.65–3.32 (3H, m, indoline C(3)H$_2$ and proline C(5)H); 2.70 (1H, m, proline C(5)H); 2.33–2.15 (4H, m, proline C(3)H$_2$ and C(4)H$_2$).

HPLC (Luna 2, Gradient 1): rt=2.98 minutes.

LC/MS (Luna 2, Gradient 4): rt=0.59 minutes, 498 (MH)$^+$.

Example 47

3-(Aminomethyl)benzoyl-D-phenylglycine 1-((S)-2-hydroxy-propanoyl)-2,3-dihydroindol-6-amide trifluoroacetate salt Prepared using (S)-2-hydroxypropanoic acid.

$^1$H NMR (d$_4$ MeOH): 8.33 ppm (1H, s, Ar); 7.97 (2H, m, Ar); 7.66–7.56 (4H, m, Ar); 7.45–7.37 (4H, m, Ar); 7.18 (1H, d, J=9 Hz, Ar); 5.83 (1H, s, CHPh); 4.58 (1H, m, CHOH); 4.31 (1H, m, indoline C(2)H); 4.21 (2H, s, CH$_2$NH$_2$); 4.15 (1H; m, indoline C(2)H); 3.18 (2H, t, J=8 Hz, indoline C(3)H$_2$); 1.4 (3H, d, J=7 Hz, CH$_3$).

HPLC (Luna 2, Gradient 1): rt=3.31 minutes.

LC/MS (Luna 2, Gradient 4): rt=1.72 minutes, 473 (MH)$^+$.

Example 48

3-(Aminomethyl)benzoyl-D-phenylglycine 1-D-prolinoyl-2,3-dihydroindol-6-amide bis(trifluoroacetate) salt Prepared using D-proline.

$^1$H NMR (d$_4$ MeOH): 8.41 ppm (1H, s, Ar); 7.97 (2H, m, Ar); 7.64–7.57 (4H, m, Ar); 7.48–7.39 (4H, m, Ar); 7.23 (1H, d, J=11 Hz, Ar); 5.82 (1H, s, CHPh); 4.63 (1H, m, proline C(2)H); 4.24 (4H, m, CH$_2$NH$_2$ and indoline C(2)H$_2$); 3.52–3.24 (3H, m, indoline C(3)H$_2$ and proline C(5)H); 2.63 (1H, m, proline C(5)H); 2.23–2.08 (4H, m, proline C(3)H$_2$ and C(4)H$_2$).

HPLC (Luna 2, Gradient 1): rt=2.98 minutes.

HPLC (Symmetry, Gradient 2): rt=4.87 minutes.

LC/MS (Luna 2, Gradient 4): rt=0.59 minutes, 498 (MH)$^+$.

Example 49

3-(Aminomethyl)benzoyl-D-phenylglycine 1-L-serinoyl-2,3-dihydroindol-6-amide bis(trifluoroacetate) salt Prepared using L-serine.

$^1$H NMR (d$_4$ MeOH): 8.40 ppm (1H, s, Ar); 7.95 (2H, m, Ar); 7.64–7.57 (4H, m, Ar); 7.47–7.39 (4H, m, Ar); 7.23 (1H, d, J=10 Hz, Ar); 5.81 (1H, s, CHPh); 4.4 (1H, dd, J=12 Hz, 4 Hz, serine CH$_a$H$_b$OH); 4.25 (2H, t, J=7 Hz, indoline C(2)H$_2$); 4.20 (2H, s, CH$_2$NH$_2$); 4.05 (1H, dd, J=12, 6 Hz, serine CH$_a$H$_b$OH); 3.91 (1H, m, serine CHNH$_2$); 3.25 (2H, t, J=7 Hz, indoline C(3)H$_2$).

HPLC (Luna 2, Gradient 1): rt=2.84 minutes.

LC/MS (Luna 2, Gradient 4): rt=1.35 minutes, 488 (MH)$^+$.

Example 50

3-(Aminomethyl)benzoyl-D-phenylglycine 1-D-serinoyl-2,3-dihydroindol-6-amide bis(trifluoroacetate) salt Prepared using D-serine.

$^1$H NMR (d$_4$ MeOH): 8.42 ppm (1H, s, Ar); 7.97 (2H, m, Ar); 7.64–7.57 (4H, m, Ar); 7.47–7.39 (4H, m, Ar); 7.23 (1H, d, J=9 Hz, Ar); 5.82 (1H, s, CHPh); 4.41 (1H, dd, J=12, 4 Hz, serine CH$_a$H$_b$OH); 4.25 (2H, t, J=7.5 Hz, indoline C(2)H$_2$); 4.2 (2H, s, CH$_2$NH$_2$); 4.05 (1H, dd, J=12, 6 Hz, serine CH$_a$H$_b$OH); 3.9 (1H, m serine CHNH$_2$); 3.25 (2H, t, J=7.5 Hz, indoline C(3)H$_2$).

HPLC (Luna 2, Gradient 1): rt=2.78 minutes.

HPLC (Symmetry, Gradient 2): rt=4.61 minutes.

LC/MS (Luna 2, Gradient 4): rt=0.65 minutes, 488 (MH)$^+$.

Example 51

3-(Aminomethyl)benzoyl-D-phenylglycine 1-(3-pyridyl-acetyl)-2,3-dihydroindol-6-amide bis(trifluoroacetate) salt Prepared using 3-pyridylacetic acid.

$^1$H NMR (d$_3$ acetonitrile): 8.91 ppm (1H, br s, Ar), 8.73–8.55 (2H, m, Ar), 8.35 (1H, br s, Ar), 8.15 (1H, d, J=10 Hz, Ar), 8.05–7.95 (2H, m, Ar), 7.80 (1H, d, J=10 Hz, Ar), 7.74–7.15 (10H, m, Ar & 2× amide NH), 5.69 (1H, d, J=7 Hz, CHPh), 4.25–4.12 (4H, m, ArCH$_2$N & dihydroindole C(2)H$_2$), 3.98 (2H, s, C(O)CH$_2$Py), 3.17 (2H, t, J=8 Hz, dihydroindole C(3)H$_2$).

HPLC (Luna 2, Gradient 1): rt=2.96 minutes.

LC/MS (Luna 2, Gradient 4): rt=1.35 minutes, 520 (MH$^+$).

Example 52

3-(Aminomethyl)benzoyl-D-phenylglycine 1-(N-acetyl)-aminoacetyl-2,3-dihydroindol-6-amide trifluoroacetate salt Prepared using N-acetylglycine.

$^1$H NMR (d$_4$ MeOH): 8.31 ppm (1H, s, Ar); 7.95 (2H, m, Ar); 7.64–7.57 (4H, m, Ar); 7.43–7.38 (4H, m, Ar); 7.18 (1H, d, J=10 Hz, Ar); 5.81 (1H, s, CHPh); 4.23–4.11 (6H, m, ArCH$_2$NH$_2$, aminoacetyl CH$_2$ and dihydroindole C(2)H$_2$); 3.21 (2H, t, J=7 Hz, dihydroindole C(3)H$_2$); 2.07 (3H, s, COCH$_3$).

HPLC (Luna 2, Gradient 1): rt=3.33 minutes.

HPLC (Symmetry, Gradient 2): rt=5.20 minutes.

LC/MS (Luna 2, Gradient 4): rt=0.59 minutes, 500 (MH)$^+$.

Example 53

3-(Aminomethyl)benzoyl-D-phenylglycine 1-(hydroxyacetyl)-2,3-dihydroindol-6-amide trifluoroacetate salt Prepared using 2-benzyloxyacetic acid.

$^1$H NMR (d$_4$ MeOH): 8.25 ppm (1H, s, Ar); 7.85 (2H, m, Ar); 7.54–7.47 (4H, m, Ar); 7.35–7.26 (4H, m, Ar); 7.10 (1H, d, J=11 Hz, Ar); 4.21 (2H, s, CH$_2$OH); 4.10 (2H, s, CH$_2$NH$_2$); 3.95 (2H, t, J=7.5 Hz, dihydroindole C(2)H$_2$); 3.21 (2H, t, J=7.5 Hz, dihydroindole C(3)H$_2$).

HPLC (Luna 2, Gradient 1): rt=3.23 minutes.
HPLC (Symmetry, Gradient 2): rt=5.26 minutes.
LC/MS (Luna 2, Gradient 4): rt=1.67 minutes, 500 (MH)$^+$.

Example 54

3-(Aminomethyl)benzoyl-D-phenylglycine 1-phenylacetyl-2,3-dihydroindol-6-amide trifluoroacetate salt Prepared using phenylacetic acid.

$^1$H NMR (d$_3$ acetonitrile): 8.78 (1H, br s, Ar), 8.23 (1H, br s, Ar), 7.90 (2H, s, Ar), 7.73 (1H, d, J=10 Hz, Ar), 7.60–7.01 (14H, m, Ar & 2× amide NH), 5.60 (1H, d, J=7 Hz, CHPh), 4.10–3.97 (4H, m, ArCH$_2$N & dihydroindole C(2)H$_2$), 3.71 (2H, s, PhCH$_2$), 2.99 (2H, t, J=8 Hz, dihydroindole C(3)H$_2$).

HPLC (Luna 2, Gradient 1): rt=4.17 minutes.
LC/MS (Luna 2, Gradient 4): rt=2.26 minutes, 519 (MH$^+$).

Example 55

3-(Aminomethyl)benzoyl-D-phenylglycine 1-(methylamino)-acetyl-2,3-dihydroindol-6-amide bis(trifluoroacetate) salt Prepared using sarcosine.

$^1$H NMR (d$_4$ MeOH): 8.39 ppm (1H, s, indoline C(7)H); 7.95 (2H, br s, 3-(aminomethyl)phenyl C(2)H and C(6)H); 7.72–7.53 (4H, m, Ar); 7.47–7.31 (4H, m, Ar); 7.24 (1H, d, J=10 Hz, indoline C(4)H or C(5)H); 5.82 (1H, br s, CHPh); 4.20 (2H, s, CH$_2$NH$_2$ or C(O)CH$_2$NHMe); 4.15 (2H, s, CH$_2$NH$_2$ or C(O)CH$_2$NHMe); 4.10 (2H, t, J=9 Hz, indoline C(2)H$_2$); 3.25 (2H, t, J=9 Hz, indoline C(3)H$_2$); 2.81 (3H, s, CH$_3$).

HPLC (Symmetry C8, Gradient 2): rt=4.75 min.
LCMS (Luna 2, Gradient 4): rt=1.45 min, 472 (MH)$^+$.

Example 56

3-(Aminomethyl)benzoyl-D-phenylglycine 3-aminopropionyl-2,3-dihydroindol-6-amide bis(trifluoracetate) salt Prepared using β-alanine.

$^1$H NMR (D$_2$O): 7.98 ppm (1H, s, indoline C(7)H); 7.72 (2H, br s, 3-(aminomethyl)phenyl C(2)H and C(6)H); 7.60–7.30 (7H, m, Ar); 7.08 (1H, d, J=10 Hz, indoline C(4)H or C(5)H); 6.95 (1H, d, J=10 Hz, indoline C(4)H or C(5)H); 5.57 (1H, s, CHPh); 4.09 (2H, s, ArCH$_2$NH$_2$); 3.82 (2H, t, J=7 Hz, indoline C(3)H$_2$); 3.20 (2H, t, J=4.5 Hz, C(O)CH$_2$CH$_2$NH$_2$); 2.95 (2H, t, J=7 Hz, indoline C(3)H$_2$); 2.71 (2H, t, J=4.5 Hz, C(O)CH$_2$CH$_2$NH$_2$).

HPLC (Symmetry C8, Gradient 2): rt=4.80 minutes.
LCMS (Luna 2, Gradient 4): rt=1.53 minutes, 472 (MH)$^+$.

Example 57

3-(Aminomethyl)benzoyl-D-phenylglycine 1-(4-pyridyl-acetyl)-2,3-dihydroindol-6-amide bis-trifluoroacetate salt Prepared using 4-pyridylacetic acid.

$^1$H NMR (CD$_3$CN): 8.91 (1H, br s, Ar), 8.73–8.55 (2H, m, Ar), 8.35 (1H, br s, Ar), 8.15 (1H, d, J=10 Hz, Ar), 8.05–7.95 (2H, m, Ar), 7.80 (1H, d, J=10 Hz, Ar), 7.74–7.15 (10H, m, Ar & 2× amide NH), 5.69 (1H, d, J=7 Hz, CHPh), 4.25–4.12 (4H, m, PhCH$_2$N & dihydroindole C(2)H$_2$), 3.98 (2H, s, C(O)CH$_2$Py), 3.17 (2H, t, J=8 Hz, dihydroindole C(3)H$_2$).

HPLC (Symmetry, Gradient 2): rt=5.43 minutes.
LC/MS (Luna 2, Gradient 4): rt=1.56 minutes, 520 (MH)$^+$.

Example 58

3-(Aminomethyl)benzoyl-D-phenylglycine 1-(imidazol-4-ylacetyl)-2,3-dihydroindol-6-amide bis(trifluoroacetate) salt Prepared using imidazol-4-ylacetic acid.

$^1$H NMR (D$_2$O): 7.75 ppm (1H, br s, NH); 7.49 (2H, br s, Ar); 7.28 (1H, d, J=8 Hz, Ar); 7.24–7.12 (9H, m, Ar); 6.92 (1H, d, J=8 Hz, Ar); 6.74 (1H, d, J=8 Hz, Ar); 6.28 (1H, s, NH); 5.38 (1H, s, CHPh); 3.87 (2H, s, ArCH$_2$NH$_2$); 3.72 (2H, d, J 8=Hz, dihydroindole C(2)H$_2$); 3.52 (2H, br s, CH$_2$Im); 2.70 (2H, t, J=8 Hz, dihydroindole C(3)H$_2$).

HPLC (Symmetry, Gradient 2): rt=4.89 minutes.
LC/MS (Luna 2, Gradient 4): rt=1.45 minutes, 509 (MH)$^+$.

Example 59

3-(Aminomethyl)benzoyl-D-phenylglycine 1-(2-aminothiazol-4-yl)-acetyl-2,3-dihydroindol-6-amide dihydrochloride Prepared using (2-formamidothiazol-4-yl)acetic acid.

$^1$H NMR (D$_2$O): 7.77 ppm (1H, br s, NH); 7.51 (2H, br s, Ar); 7.29 (1H, d, J=8 Hz, Ar); 7.24–7.03 (9H, m, Ar); 6.91 (1H, d, J=8 Hz, Ar); 6.72 (1H, d, J=8 Hz, Ar); 6.22 (1H, s, NH); 5.32 (1H, s, CHPh); 3.85 (2H, s, ArCH$_2$NH$_2$); 3.73 (2H, d, J=8 Hz, dihydroindole C(2)H$_2$); 3.56 (2H, br s, CH$_2$Thz); 2.76 (2H, t, J=8 Hz, dihydroindole C(3)H$_2$).

HPLC (Symmetry, Gradient 2): rt=5.03 minutes.
LC/MS (Luna 2, Gradient 4): rt=1.51 minutes, 541 (MH)$^+$.

Example 60

3-(Aminomethyl)benzoyl-D-phenylglycine 1-(2-formylaminothiazol-4-yl)acetyl-2,3-dihydroindol-6-amide trifluoroacetate salt Prepared using (2-formylaminothiazol-4-yl)acetic acid.

$^1$H NMR (D$_2$O): 8.30 ppm (1H, s, NCHO); 7.90 (1H, br s, ArNH); 7.64 (2H, br s, Ar); 7.42 (1H, d, J=8 Hz, Ar); 7.38–7.26 (9H, m, Ar & NH); 7.01 (1H, d, J=8 Hz, Ar); 6.96 (1H, d, J=8 Hz, Ar); 6.82 (1H, s, NH); 5.50 (1H, s, CHPh);

4.06 (2H, s, ArCH$_2$NH$_2$); 3.90 (2H, d, J=8 Hz, dihydroindole C(2)H$_2$); 3.64 (2H, br s, CH$_2$Thz); 2.90 (2H, t, J=8 Hz, dihydroindole C(3)H$_2$).

HPLC (Symmetry, Gradient 2): rt=5.75 minutes.

LC/MS (Luna 2, Gradient 4): rt=2.10 minutes, 569 (MH)$^+$.

Example 61

3-(Aminomethyl)benzoyl-D/L-(4-aminomethyl)phenylglycine indan-5-amide bis(trifluoroacetate) salt Methyl 4-bromophenylacetate Thionyl chloride (18 mL, 0.25 mol) was added dropwise to a solution of 4-bromo-phenylacetic acid (50 g; 0.23 mol) in methanol (250 mL). The resulting mixture was stirred at room temperature for 1 hour before the methanol was removed in vacuo. Ethyl acetate (300 mL) was added and the resulting solution was washed with water (3×150 mL) and 1M aqueous NaHCO$_3$ (1×150 mL), dried (MgSO$_4$) and evaporated to give the ester (52.8 g; 100%) as an orange oil which was used without further purification.

$^1$H NMR (CDCl$_3$): 7.38 ppm (2H, d, J=8.4 Hz, C(2)H and C(6)H); 7.09 (2H, d, J=8.4 Hz, C(3)H and C(5)H); 3.63 (3H, s, OMe); 3.51 (2H, s, CH$_2$).

Methyl 4-cyanophenylacetate

Zinc cyanide (10.4 g, 0.088 mol) and tetrakis-(triphenylphosphine)palladium(0) (5 g, 4.4 mmol) were added to a solution of methyl 4-bromophenylacetate (20 g, 0.088 mol) in dimethylformamide (150 mL). The resulting mixture was stirred at 80° C. for 5 hours, then allowed to cool to room temperature. Toluene (500 mL) and 1M aqueous ammonia (500 mL) were added, the layers were separated and the organic layer washed with brine (100 mL) and dried (MgSO$_4$). Evaporation of the solvents afforded an off-white solid, which was purified by silica gel chromatorgraphy to afford the cyano-compound as a white solid (11.3 g; 73%).

$^1$H NMR (CDCl$_3$): 7.65 ppm (2H, d, J=8.4 Hz, C(3)H and C(5)H); 7.42 (2H, d, J=8.1 Hz, C(2)H and C(6)H); 3.74 (3H, s, OMe); 3.72 (2H, s, CH$_2$).

4-Cyanophenylacetic acid

A solution of methyl 4-cyanophenylacetate (23.9 g; 0.136 mol) in ethanol (250 mL) was stirred at room temperature and a solution of sodium hydroxide (6.0 g; 0.15 mol) in water (25 mL) was added. After 2 hours the ethanol was removed in vacuo. Ethyl acetate (300 mL) and 5% aqueous HCl (300 mL) were added and the layers were separated. The aqueous layer was extracted with ethyl acetate (300 mL) and the combined organic layers were dried (MgSO$_4$) and evaporated in vacuo to give the acid (21.6 g; 99%) which was used without further purification.

$^1$H NMR (CDCl$_3$): 7.57 ppm (2H, d, J=8.3 Hz, C(3)H and C(5)H); 7.34 (2H, d, J=8.2 Hz, C(2)H and C(6)H); 3.64 (2H, s, CH$_2$).

4-(N-BOC-aminomethyl)phenylacetic acid

A solution of 4-cyanophenylacetic acid (12.11 g, 0.075 mol) in water (163 mL) and concentrated aqueous ammonia (40 mL) was stirred at room temperature and Raney nickel (6.3 g) was added. The resulting suspension was stuirred under a hydrogen atmosphere for 24 hours before the reaction mixture was filtered through celite and evaporated in vacuo to give crude 4-(aminomethyl)-phenylacetic acid (12.57 g; 100%) as a pale blue solid.

A solution of the crude amino acid (12.57 g, 0.075 mol) in water (50 mL) and 1,4-dioxane (50 mL) was stirred at room temperature and sodium hydroxide (3 g, 0.075 mol) and di-$^t$butyl dicarbonate (16.4 g, 0.075 mol) were added simultaneously. After 24 hours the 1,4-dioxane was removed in vacuo and the aqueous layer was acidified with saturated aqueous citric acid (200 mL). The solution was extracted with ethyl acetate (3×150 mL) and the combined organic layers were dried (MgSO$_4$) and evaporated in vacuo to give the N-BOC-amine (17.6 g, 88%) as a white solid which was used without further purification.

$^1$H NMR (CDCl$_3$): 7.00 ppm (4H, m, Ar); 4.65 (1H, br s, N—H); 4.09 (2H, d, J=6 Hz, CH$_2$NH); 3.43 (2H, s, CH$_2$); 1.25 (9H, s, $^t$Bu).

Methyl 4-(N-BOC-aminomethyl)phenylacetate

1-[3-(Dimethylamino)propyl]-3-ethylcarbodiimide hydrochloride (34.8 g, 0.18 mol) and 4-(N,N-dimethylamino)pyridine (220 mg, 1.8 mmol) were added to a solution of 4-(N-BOC-aminomethyl)phenylacetic acid (47.8 g, 0.18 mol) in methanol (200 ml). After stirring for 18 hours the methanol was removed in vacuo and the reaction mixture partitioned between ethyl acetate (200 mL) and saturated aqueous citric acid (200 mL). The organic phase was separated and washed with saturated aqueous NaHCO$_3$ (200 mL) and brine (200 mL), dried (MgSO$_4$) and evaporated to give the methyl ester (49.8 g; 99%).

$^1$H NMR (CDCl$_3$): 7.42 ppm (4H, s, Ar); 5.02 (1H, br s, N—H); 4.48 (2H, d, J=5.7 Hz, CH$_2$NH); 3.87 (3H, s, OMe); 3.79 (2H, s, CH$_2$); 1.64 (9H, s, $^t$Bu).

Methyl[4-(N-BOC-aminomethyl)phenyl]-α-azidoacetate

A solution of methyl 4-(N-BOC-aminomethyl)phenylacetate (9.34 g; 0.033 mol) in THF (100 mL) was stirred under argon at −78° C. and potassium bis(trimethylsilyl)amide (16.7 g, 0.084 mol) in THF (50 mL) was added. After stirring for 30 minutes, 2,4,6-triisopropylbenzene-sulfonyl azide (31.1 g, 0.101 mol) was added as a solid. After 5 minutes, acetic acid (10 mL, 0.175 mol) was added and the reaction warmed to room temperature. The reaction mixture was then partitioned between ethyl acetate (500 mL) and water (500 mL), separated and the organic layer dried (MgSO$_4$). Evaporation of the solvent and purification of the residue by silica gel chromatography afforded the azide (7.1 g, 67%).

$^1$H NMR (CDCl$_3$): 7.28 ppm (4H, s, Ar); 4.92 (1H, s, CHN$_3$); 4.25 (2H, s, CH$_2$NH); 3.69 (3H, s, OMe); 1.38 (9H, s, $^t$Bu).

Methyl α-amino-[4-(N-BOC-aminomethyl)phenylacetate

A solution of methyl(4-(N-BOC-aminomethyl)phenyl]-α-azidoacetate (7.1 g, 0.022 mol) in ethyl acetate (50 mL) was stirred over palladium on carbon (5%). The reaction vessel was taken up to 250 psi with hydrogen for 17 hours. The reaction mixture was filtered through celite and evaporated in vacuo to give the amine (6.47 g, 100%) as a pale solid.

$^1$H NMR (CDCl$_3$): 7.20 ppm (2H, m, Ar); 7.12 (2H, m, Ar); 4.81 (1H, br s, NH); 4.45 (1H, s, CH); 4.18 (2H, d, J=6 Hz, CH$_2$NH); 3.54 (3H, s, OMe); 2.09 (2H, br s, NH$_2$); 1.30 (9H, s, $^t$Bu).

Methyl α-(N-benzyloxycarbonyl-amino)-[4-(N-BOC-aminomethyl)phenyl]acetate

A solution of the amine (530 mg, 1.8 mmol) in tetrahydrofuran (15 mL) was treated with triethylamine (0.25 mL, 1.8 mmol) and benzyl chloroformate (0.26 mL, 1.8 mmol) and allowed to stir at room temperature for 1 hour. The reaction was diluted with ethyl acetate (40 mL), washed with brine (2×25 mL), dried (MgSO$_4$) and concentrated under reduced pressure to afford a yellow oil. The benzyloxycarbonyl ester was purified by flash chromatography on silica gel (ethyl acetate/hexane 1:1) to give a yellow solid (312 mg, 66%).

$^1$H NMR (CDCl$_3$): 7.32–7.15 ppm (9H, m, 9 Ar); 5.80 (1H, br s, NH); 5.30 (1H, d, J=9.6 Hz, CH); 5.01 (2H, s, CH$_2$Ph); 4.22 (2H, d, J=7.2 Hz, CH$_2$NHBoc); 3.63 (3H, s, OCH3); 1.39 (9H, s, $^t$Bu).

D/L-α-(N-benzyloxycarbonyl)-[4-(N-BOC-aminomethyl) phenyl]glycine

A solution of the ester (356 mg, 0.83 mmol) in tetrahydrofuran (15 mL) was treated with 1 M LiOH (1.7 mL, 1.7 mmol) and heated at reflux for 3 hours. The solvent was removed under reduced pressure and the residue diluted with water (20 mL). The pH was reduced to 4 using 5% aqueous HCl and the aqueous phase was extracted with ethyl acetate (3×20 mL). The combined organic extracts were dried (MgSO$_4$) and concentrated under reduced pressure to afford the acid as a yellow solid (273 mg, 79%) which was carried forward without further purification.

D/L-α-(N-benzyloxycarbonyl)-[4-(N-BOC-aminomethyl)phenyl]glycine indan-5-amide A solution of the acid (173 mg, 0.42 mmol) in dimethylformamide (15 ml) was treated with 1-(3-dimethylaminopropyl)-3-ethylcarbodiimide hydrochloride (80 mg, 0.42 mmol), 1-hydroxy-7-azabenzotriazole (57 mg, 0.42 mmol), 5-aminoindane (56 mg, 0.42 mmol) and 4-(N,N-dimethylamino)pyridine (5 mg) and stirred overnight at room temperature before being partitioned between ethyl acetate (50 mL) and water (50 mL). The layers were separated and the organic phase was washed with 5% aqueous HCl (25 mL), saturated aqueous NaHCO$_3$ (25 mL) and water (25 mL), dried (MgSO$_4$) and concentrated under reduced pressure to afford the indanamide as a colourless solid (160 mg, 72%) which was used without further purification.

$^1$H NMR (CDCl$_3$): 7.39–7.09 ppm (12H, m, 10 Ar and 2 NH); 6.99 (2H, s, Ar); 5.38 (1H, br s, CHAr); 5.01 (2H, s, CH$_2$Ph); 4.81 (1H, m, NH); 4.19 (2H, s, CH$_2$NHBOC); 2.85–2.68 (4H, m, indane C(1)H$_2$ and C(3)H$_2$); 2.04–1.88 (2H, m, indane C(2)H$_2$); 1.39 (9H, s, $^t$Bu).

3-(N-BOC-Aminomethyl)benzoyl-D/L-4-(N-BOC-aminomethyl)-phenylglycine indan-5-amide 10% Palladium on carbon (50 mg), was added to a solution of the indanamide (160 mg, 0.3 mmol) in ethanol (20 mL) and the suspension was stirred under a hydrogen atmosphere overnight The mixture was filtered and the filter was washed with ethanol (20 ml). The combined filtrates were concentrated under reduced pressure to afford the amine as a colourless solid (107 mg, 90%) which was carried forward without further purification.

A solution of the amine (107 mg, 0.27 mmol) in dimethylformamide (15 mL) was treated with 1-(3-dimethylaminopropyl)-3-ethylcarbodiimide hydrochloride (52 mg, 0.27 mmol), 1-hydroxy-7-azabenzotriazole (37 mg, 0.27 mmol), N-BOC-3-(aminomethyl)benzoic acid (68 mg, 0.27 mmol) and 4-(N,N-dimethylamino)pyridine (5 mg) and stirred overnight at room temperature. The solution was partitioned between ethyl acetate (25 mL) and water (25 mL) and the organic phase was separated and washed with 5% aqueous HCl (25 mL), saturated aqueous NaHCO$_3$ (25 mL) and water (25 mL) before being dried (MgSO$_4$) and concentrated under reduced pressure to afford a yellow solid. The residue was purified by flash chromatography on silica gel (ethyl acetate/hexane 1:1) to give the diprotected bis-amide as a colourless solid (103 mg, 61%).

$^1$H NMR (CDCl$_3$): 9.25 ppm (1H, s, NH); 7.94 (1H, d, J=7.2 Hz, Ar); 7.62 (2H, s, Ar); 7.43–7.24 (5H, m, 4 Ar, NH); 7.05 (3H, d, J=7.2 Hz, Ar); 6.94 (1H, d, J=7.2 Hz, Ar); 6.14 (1H, d, J=7.2 Hz, CH); 5.07 (1H, m, NH); 4.99 (1H, m, NH); 4.16 (2H, s, CH$_2$NHBOC); 4.10 (2H, s, CH$_2$NHBOC); 2.77–2.61 (4H, m, indane C(1)H$_2$ and C(3)H$_2$); 1.98–1.87 (2H, m, indane C(2)H$_2$); 1.35 (9H, s, $^t$Bu).

3-(Aminomethyl)benzoyl-D/L-4-(aminomethyl)phenylglycine indan-5-amide bis(trifluoroacetate) salt A solution of the diprotected bis-amide (103 mg, 0.16 mmol) in dichloromethane (5 mL) was stirred at room temperature and trifluoroacetic acid (3 mL) was added. Stirring was continued for a further hour before the solvents were removed under reduced pressure to afford the bis (trifluoroacetate) salt as a colourless solid (92 mg, 88%).

$^1$H NMR (d$_4$ MeOH): 7.90 ppm (1H, s, Ar); 7.84 (1H, s, Ar); 7.65–7.54 (4H, m, Ar); 7.49–7.32 (3H, m, Ar); 7.12 (1H, d, J=7.2 Hz, Ar); 7.02 (1H, d, J=7.2 Hz, Ar); 5.78 (1H, s, CHAr); 4.08 (2H, s, CH$_2$NH$_2$); 4.01 (2H, s, CH$_2$NH$_2$); 2.79–2.70 (4H, m, indane C(1)H$_2$ and C(3)H$_2$); 2.03–1.90 (2H, m, indane C(2)H$_2$).

HPLC (Luna 2, Gradient 1): rt=3.13 minutes.

LCMS (Luna 2, Gradient 4): rt=1.45 minutes, 429 (MH)$^+$.

Examples 62–64 were prepared in a similar fashion to Example 61, using the specified amine in place of 5-aminoindane.

Example 62

3-(Aminomethyl)benzoyl-D/L-4-(aminomethyl)phenylglycine 1-aminoacetyl-2,3-dihydroindol-6-amide tris(trifluoroacetate salt)

Prepared from 6-amino-1-(N-BOC-aminoacetyl)-2,3-dihydroindole.

$^1$H NMR (d$_4$ MeOH): 8.23 ppm (1H, s, Ar); 7.84–7.74 (2H, m, Ar); 7.56–7.30 (6H, m, Ar); 7.17 (1H, d, J=7.2 Hz, Ar); 7.02 (1H, d, J=7.2 Hz, Ar); 5.68 (1H, s, CHAr); 4.02 (2H, s, CH$_2$NH$_2$); 3.99–3.79 (6H, m, CH$_2$NH$_2$, dihydroindole C(2)H$_2$, CH$_2$NH$_2$ glycine); 3.06–2.97 (2H, m, dihydroindole C(3)H$_2$).

HPLC (Luna 2, Gradient 1): rt=2.13 minutes.

LCMS (Luna 2, Gradient 4): rt=0.51 minutes, 487 (MH)$^+$.

Example 63

3-(Aminomethyl)benzoyl-D/L-4-(aminomethyl)phenylglycine 1-acetyl-2,3-dihydroindole bis(trifluoroacetate) salt Prepared from 1-acetyl-6-amino-2,3-dihydroindole.
$^1$H NMR ($d_4$ MeOH): 8.21 ppm (1H, s, Ar); 7.97–7.86 (2H, m, Ar); 7.72–7.43 (6H, m, Ar); 7.32 (1H, d, J=7.2 Hz, Ar); 7.12 (1H, d, J=7.2 Hz, Ar); 5.81 (1H, s, CHAr); 4.17 (1H, s, CH$_2$NH$_2$); 4.15–4.04 (4H, m, CH$_2$NH$_2$, dihydroindole C(2)H$_2$); 3.19–3.07 (2H, m, dihydroindole C(3)H$_2$); 2.20 (3H, s, NCOCH$_3$).
HPLC (Luna 2, Gradient 1): rt=2.72 minutes.
LCMS (Luna 2, Gradient 4): rt=1.18 minutes, 472 (MH)$^+$.

Example 64

3-(Aminomethyl)benzoyl-D/L-4-(aminomethyl)phenylglycine 4-(isopropyl)phenylamide bis(trifluoroacetate salt)

Prepared from 4-isopropylaniline.
$^1$H NMR ($d_4$ MeOH): 8.01–7.92 ppm (2H, m, Ar); 7.75–7.43 (8H, m, Ar); 7.18 (2H, d, J=9.6 Hz, Ar); 5.87 (1H, s, CHAr); 4.21 (2H, s, CH$_2$NH$_2$); 4.14 (2H, s, CH$_2$NH$_2$); 2.96–2.81 (1H, m, CH(CH$_3$)$_2$); 1.24 (6H, d, J=7 Hz, CH(CH$_3$)$_2$).
HPLC (Luna 2, Gradient 1): rt=3.39 minutes.
LCMS (Luna 2, Gradient 4): rt=1.59 minutes, 431 (MH)$^+$.

Examples 65–68 were prepared in a similar manner to Example 61 except that the indicated protected amino acid was used in the place of D/L-4-(N-BOC-aminomethyl)-α-(N-benzyloxycarbonyl)phenylglycine.

Example 65

3-(Aminomethyl)benzoyl-D-cyclohexylglycine indan-5-amide trifluoroacetate salt

Prepared from N-BOC-D-cyclohexylglycine.
$^1$H NMR ($d_4$ MeOH): 7.88–7.02 ppm (7H, m, Ar); 4.43 (1H, d, J=9 Hz, CH(cHex)); 4.04 (2H, s, CH$_2$NH$_2$); 2.78–2.68 (4H, m, indane C(1)H$_2$ and C(3)H$_2$); 2.04–1.82 (4H, m, indane C(2)H$_2$, cHex CH$_2$); 1.77–1.56 (4H, m, 2× cHex CH$_2$); 1.36–0.95 (5H, m, 2× cHex CH$_2$ and CH).
HPLC (Luna 2, Gradient 1): rt=4.27 minutes.
LCMS (Luna 2, Gradient 4): rt=2.21 minutes, 406 (MH)$^+$.

Example 66

3-(Aminomethyl)benzoyl-D/L-1-naphthylglycine indan-5-amide trifluoroacetate salt Prepared from N-BOC-D/L-1-naphthylglycine.
$^1$H NMR ($d_4$ MeOH): 8.25 ppm (1H, d, J=7.2 Hz, Ar); 8.04–7.84 (4H, m Ar); 7.75–7.44 (7H, m, Ar); 7.33 (1H, d, J=7.25 Hz, Ar); 7.16 (1H, d, J=7.25 Hz, Ar); 6.72 (1H, s, CHAr); 4.15 (2H, s, CH$_2$NH$_2$); 2.94–2.78 (4H, m, indane C(1)H$_2$C(3)H$_2$); 2.17–1.98 (2H, m, indane C(2)H$_2$).
HPLC (Luna 2, Gradient 1): rt=4.37 minutes.
LCMS (Luna 2, Gradient 4): rt=2.37 minutes, 450 (MH)$^+$.

Example 67

3-(Aminomethyl)benzoyl-D/L-(4-phenyl)phenylglycine indan-5-amide trifluoroacetate salt Prepared from N-Fmoc-D/L-(4-phenyl)phenylglycine.
$^1$H NMR ($d_4$ MeOH): 7.94–7.83 ppm (2H, m, Ar); 7.64–7.15 (13H, m, Ar); 7.02 (1H, d, J=7.2 Hz, Ar); 5.80 (1H, s, CH); 4.08 (2H, s, CH$_2$NH$_2$); 2.81–2.77 (4H, m, indane C(1)H$_2$ and C(3)H$_2$); 2.01–1.88 (2H, m, indane C(2)H$_2$).
HPLC (Luna 2, Gradient 1): rt=4.87 minutes.
LCMS (Luna 2, Gradient 4): rt=2.56 minutes, 476 (MH)$^+$.

Example 68

3-(Aminomethyl)benzoyl-D-(4-aminophenyl)glycine indan-5-amide bis(trifluoroacetate) salt Prepared from N-BOC-D-(4-Benzyloxycarbonylaminophenyl)-glycine (prepared as described below).

D-(4-Hydroxyphenyl)glycine methyl ester hydrochloride

D-4-Hydroxyphenylglycine (12.5 g, 74.8 mmol) and dry methanol (24 mL) were stirred in a dry 250 mL three necked round bottom flask, equipped with a low temperature thermometer. The mixture was stirred under nitrogen and cooled to an internal temperature of below −20° C. Using a syringe, thionyl chloride (6 mL, 9,78 g, 82.2 mmol) was added dropwise to the cooled mixture over a period of 10 minutes at such a rate that the internal temperature did not exceed −20° C. Once the addition was complete the mixture was allowed to warm to room temperature and stirred overnight. Dry ether (150 mL) was added and the white precipitate that formed was collected by suction filtration, washed with a little more ether and dried (15.5 g, 95%).

N-BOC-D-(4-Hydroxyphenyl)glycine methyl ester

Di-t-butyl dicarbonate (15.9 g, 72.8 mmol) was added to a stirred mixture of D-4-hydroxyphenylglycine methyl ester hydrochloride (14 g, 64.3 mmol) and NaHCO$_3$ (11.7 g, 0.14 mol) in tetrahydrofuran (150 mL) and water (50 mL), in one portion. The mixture was stirred rapidly for 4 h. Hexane (75 mL) was added and the organic layer separated and washed with saturated aqueous NaHCO$_3$ (20 mL) and brine (20 mL) and dried (MgSO$_4$). Evaporation of the solvent afforded the N-BOC-protected amine (19.7 g, 96%).

N-BOC-D-(4-Trifluoromethylsulphonyloxyphenyl) glycine methyl ester 2,6-Lutidine (9.44 ml, 8.68 g, 81.0 mmol) and 4-dimethylaminopyridine (1.65 g, 13.5 mmol) were added to a stirred solution of N-BOC-D-(4-hydroxyphenyl)glycine methyl ester (19 g, 67.5 mmol) in dichloromethane (400 mL) and the mixture cooled in an ice bath. Trifluoromethananesulphonic anhydride (13.7 mL, 23.0 g, 81.4 mmol) was added over a period of five minutes and then the mixture was allowed to warm to room temperature over four hours. The solution was washed with water (2×150 mL), 1N HCl (2×150 mL) and saturated aqueous NaHCO$_3$ (150 mL) and dried (MgSO$_4$). Evaporation of the solvent afforded an oil which was purified by flash chromatography on silica gel (hexane/dichloromethane 1:1 and then neat dichloromethane) affording the triflate as a white solid (19 g, 77%).

N-BOC-D-(4-benzyloxycarbonylphenyl)glycine methyl ester

N-BOC-D-(4-trifluoromethylsulphonyloxyphenyl)glycine methyl ester (27.6 g, 77.0 mmol), benzyl alcohol (32.6 mL, 34.1 g, 315 mmol), palladium (II) acetate (255 mg, 1.13 mmol), bis-1,3-diphenylphosphinylpropane (448 mg, 1.09 mmol) and triethylamine (10.2 mL, 7.40 g, 73.2 mmol) in dimethylformamide (72 mL) were placed in a Parr reactor and the reactor assembled. The vessel was pressurised to ~10 psi with nitrogen and the gas released (repeated five times to remove all oxygen from the system). Carbon monoxide gas was then carefully introduced to ~20 psi and released three times.

Carbon monoxide was then added to ~100 psi and the stirrer started. The vessel was slowly heated to 65° C. internal temperature and then stirred, monitoring by tlc. When complete (after ~18 hours) the reaction was cooled to 30° C., the gas released and the vessel flushed five times with nitrogen as before. The reaction mixture was partitioned between ethyl acetate (250 mL) and water (100 mL) and the organic layer washed with 1M hydrochloric acid (30 mL) and saturated aqueous $NaHCO_3$ (30 mL) and dried ($MgSO_4$) and evaporated. Purification of the resulting oil by column chromatography (ethyl acetate/hexane; 1:4) gave the benzyl ester (18.7 g, 70%).

N-BOC-D-(4-hydroxycarbonylphenyl)glycine methyl ester

10% Palladium on carbon (100 mg) was added to a solution of the benzyl ester (500 mg, 1.25 mmol) in ethanol (15 mL) and the suspension was stirred under a hydrogen atmosphere overnight. The mixture was filtered and the residue was washed with ethanol (20 mL) and the combined organic solvents were evaporated under reduced pressure to afford the acid as a colourless solid (363 mg, 94%).

$^1$H NMR ($CDCl_3$): 8.08 ppm (2H, br s, Ar); 7.49 (2H, d, J=7.2 Hz, Ar); 5.87 (1H, d, J=9 Hz, NHCH); 3.73 (3H, s, $OCH_3$); 1.41 (9H, s, $^tBu$).

N-BOC-D-(4-Benzyloxycarbonylaminophenyl)glycine methyl ester

The acid (218 mg, 0.7 mmol) in tetrahydrofuran (20 mL) was treated with triethylamine (108 µl, 0.78 mmol) and diphenylphosphonic azide (161 µl, 0.78 mmol) and stirred at room temperature for 1.5 hours. Benzyl alcohol (116 µl, 1.12 mmol) was then added and the mixture was heated at reflux for 18 hours. The solvent was evaporated under reduced pressure and the residue was purified by flash chromatography (ethyl acetate/hexane, 1:1) to give the N-benzyloxycarbonylaniline as a brown solid (87 mg, 30%).

$^1$H NMR ($CDCl_3$): 7.35–7.23 ppm (7H, m, Ar); 7.16 (2H, d, J=9 Hz, Ar); 7.06 (1H, s, NH); 5.53 (1H, d, J=9 Hz, CHAr); 5.18 (1H, d, J=9 Hz, NH); 5.10 (2H, s, $CH_2Ph$); 3.59 (3H, s, $OCH_3$); 1.31 (9H, s, $^tBu$).

N-BOC-D-(4-Benzyloxycarbonylaminophenyl)glycine

A solution of the ester (87 mg, 0.21 mmol) in tetrahydrofuran (5 mL) was treated with 1 M LiOH (0.84 ml, 0.84 mmol) and heated at reflux for four hours. The solvent was removed under reduced pressure and the residue was diluted with water (10 mL). The aqueous solution was acidified to pH 4 using 5% aqueous HCl and extracted with ethyl acetate (3×10 mL). The combined extracts were dried ($MgSO_4$) and evaporated under reduced pressure to afford the crude acid (80 mg, 95%) as a colourless solid which was carried forward without further purification.

3-(Aminomethyl)benzoyl-D-(4-aminophenyl)glycine indan-5-amide bis(trifluoroacetate) salt $^1$H NMR ($d_4$ MeOH): 7.92–7.80 ppm (2H, m, Ar); 7.69 (2H, d, J=7.3 Hz, Ar); 7.60–7.40 (2H, m, Ar); 7.34 (3H, d, J=12 Hz, Ar); 7.15 (1H, d, J=7.2 Hz, Ar); 7.02 (1H, d, J=7.2 Hz, Ar); 5.79 (1H, s, CHAr); 4.07 (2H, s, $CH_2NH_2$); 2.80–2.69 (4H, m, indane $C(1)H_2$ and $C(3)H_2$); 2.01–1.88 (2H, m, indane $C(2)H_2$).

HPLC (Luna 2, Gradient 1): rt=3.17 minutes.
LCMS (Luna 2, Gradient 4): rt=1.59 minutes, 415 $(MH)^+$.

Example 69

3-(Aminomethyl)benzoyl-D/L-piperidin-4-ylglycine indan-5-amide bis(trifluoroacetate) salt (N-BOC-Piperidin-4-ylidene)-(N-benzyloxycarbonyl)glycine methyl ester N-BOC-4-Piperidone (2.0 g, 10 mmol), N-(benzyloxycarbonyl)-α-phosphonoglycine trimethyl ester (3.64 g, 2.20 mmol) and 1,8-diazabicyclo[5.4.0]undec-7-ene (1.57 mL, 2.10 mmol) were stirred in acetonitrile overnight. The solvent was removed and the residue taken up in ethyl acetate (50 mL) and washed with water (2×10 mL), dried ($MgSO_4$) and evaporated under reduced pressure. The residual oil was purified by chromatography on silica gel (ethyl acetate/hexane, 40%/60%) to afford the unsaturated ester (3.63 g, 90%).

$^1$H NMR ($CDCl_3$): 7.36 ppm (5H, br s, Ph); 6.05 (1H, br s, NH); 5.12 (2H, s, $CH_2Ph$); 3.73 (3H, br s, OMe); 3.50 (4H, br s, piperidine $C(2)H_2$ and $C(6)H_2$); 2.86 (2H, br s, piperidine $C(3)$ $H_2$ or $C(5)H_2$); 2.45–2.36 (2H, m, piperidine $C(3)H_2$ or $C(5)$ $H_2$); 1.47 (9H, s, $^tBu$).

(N-BOC-Piperidin-4-ylidene)-(N-benzyloxycarbonyl)glycine

A solution of the methyl ester (391 mg, 1 mmol) in tetrahydrofuran (10 mL) was treated with 1 M LiOH (2 mL, 2 mmol) and heated at reflux for 4 hours. The solvent was removed under reduced pressure and the residue diluted with water (20 mL). The aqueous solution was acidified to pH 4 with 5% aqueous HCl and extracted with ethyl acetate (3×20 mL). The combined organic extracts were dried ($MgSO_4$) and concentrated under reduced pressure to afford the acid as a brown solid (305 mg, 78%) which was carried forward without further purification.

(N-BOC-Piperidin-4-ylidene)-(N-benzyloxycarbonyl)glycine indan-5-amide

A solution of the acid (253 mg, 0.65 mmol) in dimethylformamide (20 mL) was treated with 1-(3-dimethylaminopropyl)-3-ethylcarbodiimide hydrochloride (124 mg, 0.65 mmol), 1-hydroxy-7-azabenzotriazole (88 mg, 0.65 mmol), 5-aminoindane (86 mg, 0.65 mmol) and 4-(N,N-dimethylamino)pyridine (10 mg) and stirred overnight at room temperature. The solution was partitioned between ethyl acetate (30 mL) and water (30 mL), separated, and the organic phase was washed with 5% aqueous HCl (30 mL), saturated aqueous NaHCO$_3$ (30 mL) and water (30 mL), dried (MgSO$_4$) and concentrated under reduced pressure to afford a colourless solid. The crude product was purified by flash chromatography (ethyl acetate/hexane 1:1) to afford the indanamide as a colourless solid (215 mg, 65%).

$^1$H NMR (CDCl$_3$): 8.31 (1H, br s, NH); 7.43 (9H, m, 8 Ar, NH); 5.01 (2H, s, CH$_2$Ph); 3.34 (4H, br s, piperidine C(2)H$_2$ and C(6)H$_2$); 2.83–2.71 (4H, m, indane C(1)H$_2$ and C(3)H$_2$); 2.54 (2H, br s, piperidine C(3)H$_2$ or C(5)H$_2$); 2.23–2.14 (2H, m, piperidine C(3)H$_2$ or C(5)H$_2$); 2.05–1.92 (2H, m, indane C(2)H$_2$); 1.38 (9H, s, $^t$Bu).

D/L-(N-BOC-Piperidin-4-yl)glycine indan-5-amide

10% Palladium on carbon (50 mg) was added to a solution of the alkene (215 mg, 0.43 mmol) in ethanol (20 mL) and the suspension was stirred under a hydrogen atmosphere overnight. The mixture was filtered and the filtrand was washed with ethanol (20 ml) before the combined solvents were concentrated under reduced pressure to afford the deprotected saturated amine as a colourless oil (97 mg, 60%). The crude amine was carried forward without further purification.

The remaining steps of the synthesis are identical to those of Example 61.

3-(Aminomethyl)benzoyl-D/L-piperidin-4-ylglycine indan-5-amide bis(trifluoroacetate) salt $^1$H NMR (d$_4$ MeOH): 8.04–7.92 ppm (2H, m, Ar); 7.73–7.55 (2H, m, Ar); 7.49 (1H, s, Ar); 7.32 (1H, d, J=7.2 Hz, Ar); 7.18 (1H, d, J=7.2 Hz, Ar); 4.68 (1H, d, J=9 Hz, CH(Pip)); 4.21 (2H, s, CH$_2$NH$_2$); 3.54–3.40 (2H, m, piperidine C(2)H and C(6)H); 3.13–2.96 (2H, m, piperidine C(2)H and C(6)H); 2.94–2.81 (4H, m, indane C(1)H$_2$ and C(3)H$_2$); 2.41–2.23 (1H, m, piperidine C(4)H); 2.20–1.95 (4H, m, indane C(2)H$_2$, piperidine C(3)H and C(4)H); 1.84–1.60 (2H, m, piperidine C(3)H and C(4)H).

HPLC (Luna 2, Gradient 1): rt=3.08 minutes.
LCMS (Luna 2, Gradient 4): rt=1.27 minutes, 407 (MH)$^+$.

Example 70

2-Amino-5-(aminomethyl)benzoyl-D-phenylglycine indan-5-ylamide bis(trifluoroacetate) salt 2-Amino-5-cyanobenzoic acid A solution of 2-amino-5-bromobenzoic acid (6.9 g, 31.9 mmol) in N-methyl-2-pyrrolidinone (100 mL) was treated with copper cyanide (4.14 g, 46 mmol) and the mixture was heated at 190° C. for 4.5 hours before being cooled to room temperature and allowed to stand overnight. The mixture was diluted with water (500 mL), acidified with 6N aqueous HCl (100 mL) and extracted with ethyl acetate (6×40 mL). The organic extracts were dried (MgSO$_4$) and concentrated under reduced pressure to yield the crude nitrile (4.35 g, 84%).

2-Amino-5-cyanobenzoyl-D-phenylglycine methyl ester

A solution of 2-amino-5-cyanobenzoic acid (1.0 g, 6.17 mmol) in dimethylformamide (50 mL) was treated with 1-(3-dimethylaminopropyl)-3-ethylcarbodiimide hydrochloride (1.18 g, 6.17 mmol) and 1-hydroxy-7-azabenzotriazole (0.84 g, 6.17 mmol). After stirring for 10 minutes, D-phenylglycine methyl ester (1.24 g, 6.17 mmol) was added and the resulting solution was stirred overnight at room temperature. The mixture was partitioned between ethyl acetate (50 mL) and water (50 mL) and the organic solution was washed with saturated aqueous citric acid (50 mL), saturated aqueous NaHCO$_3$ (50 mL) and water (50 mL), dried (MgSO$_4$) and concentrated under reduced pressure. The crude product was purified by flash column chromatography (ethyl acetate/hexane, 1:1) to yield 2-amino-5-cyanobenzoyl-D-phenylglycine methyl ester (1.3 g, 68%).

LC/MS (Luna 2, Gradient 4): rt=3.28 minutes, 310 (MH)$^+$.

2-(Di-t-butoxycarbonyl)amino-5-cyanobenzoyl-D-phenylglycine methyl ester

A solution of 2-amino-5-cyanobenzoyl-D-phenylglycine methyl ester (800 mg, 2.6 mmol) in dimethylformamide (20 mL) was treated with 4-dimethylaminopyridine (30 mg; 0.3 mmol), 1-(3-dimethylaminopropyl)-3-ethylcarbodiimide hydrochloride (500 mg; 2.6 mmol) and di-t-butyldicarbonate (570 mg; 2.6 mmol). The mixture was stirred overnight at room temperature and then partitioned between ethyl acetate (25 mL) and water (25 mL). The organic extracts were dried (MgSO$_4$), concentrated under reduced pressure and the residue was purified by flash column chromatography (ethyl acetate/hexane 3:7) to yield the bis-protected amine (150 mg, 11%).

2-(Di-t-butoxycarbonyl)amino-5-cyanobenzoyl-D-phenylglycine

The ester (150 mg, 0.29 mmol) was dissolved in tetrahydrofuran (20 mL) and treated with 1 M lithium hydroxide (0.6 mL, 0.6 mmol). The mixture was heated at reflux for 3 hours, cooled to room temperature and concentrated under reduced pressure. The residue was diluted with water (10 mL), acidified with 5% aqueous HCl (10 mL) and the product extracted into ethyl acetate (25 mL). The organic extracts were then dried (MgSO$_4$) and concentrated under reduced pressure and the crude acid (110 mg, 75%) was carried forward without further purification.

2-(Di-t-butoxycarbonyl)amino-5-cyanobenzoyl-D-phenylglycine indan-5-ylamide

A solution of the acid (110 mg, 0.20 mmol) in dimethylformamide (1.0 mL) was treated with 1-(3-dimethylaminopropyl)-3-ethylcarbodiimide hydrochloride (30 mg, 0.2 mmol) and 1-hydroxy-7-azabenzo-triazole (30 mg, 0.2 mmol). After stirring for 10 minutes, 5-aminoindane (30 mg, 0.2 mmol) was added and the resulting solution stirred overnight at room temperature. The mixture was partitioned between ethyl acetate (25 mL) and water (25 mL) and the organic solution was washed with saturated aqueous citric acid (25 mL), saturated aqueous NaHCO$_3$ (25 mL) and water (25 ml), dried (MgSO$_4$) and concentrated under reduced pressure. The crude product was purified by flash column chromatography (ethyl acetate/hexane, 3:7) to yield 2-(di-t-butoxycarbonyl)amino-5-cyanobenzoyl-D-phenylglycine indan-5-ylamide as an off-white solid (50 mg, 40%).

2-Amino-5-(aminomethyl)benzoyl-D-phenylglycine indan-5-ylamide bis(trifluoroacetate) salt A solution of the nitrile (50 mg, 0.08 mmol) in methanol (10 mL) and 36% aqueous HCl (0.5 ml) was stirred over 10% palladium on carbon (20 mg) under a hydrogen atmosphere for 16 hours. The mixture was filtered and the residue was washed with methanol (10 mL) before concentrating the extracts under reduced pressure.

The residue was dissolved in a mixture of trifluoroacetic acid (5 ml) and dichloromethane (5 ml) and stirred for one hour. The mixture was concentrated under reduced pressure and the residue purified by preparative HPLC to afford 2-amino-5-(aminomethyl)benzoyl-D-phenylglycine indan-5-ylamide ditrifluoroacetate salt (2 mg, 6%).

$^1$H NMR (d$_4$ MeOH): 7.98–7.37 ppm (10H, m, Ar); 7.02 (1H, d, J=7.5 Hz, Ar); 6.03 (1H, s, C$\underline{H}$Ph); 3.92 (2H, s, C$\underline{H}_2$NH$_2$); 3.09 (4H, q, J=7.5 Hz, indane C(1)H$_2$ and C(3)H$_2$); 2.29 (2H, quintet, J=7.5 Hz, indane C(2)H$_2$).

HPLC (Luna 2, Gradient 1): rt=4.04 minutes.

LC/MS (Luna 2, Gradient 4): rt=2.10 minutes, 398 (MH-NH$_3$)$^+$.

Example 71

1-(2-Amino-5-(aminomethyl)benzoyl-D-phenylglycinyl) 4-hydroxypiperidine dihydrochloride salt D-Phenylglycine 4-hydroxypiperidinamide trifluoroacetate salt A solution of 4-hydroxypiperidine (330 mg, 1.4 mmol) in dimethylformamide (10 mL) was treated with 2-(1H-benzotriazole-1-yl)-1,1,3,3-tetramethyluronium tetrafluoroborate (450 mg; 1.4 mmol) and N-ethyldiisopropylamine (0.74 mL, 4.2 mmol). After stirring for 10 minutes, N-butoxycarbonyl-D-phenylglycine (330 mg, 1.4 mmol) was added and the resulting solution stirred overnight at room temperature. The mixture was partitioned between ethyl acetate (25 mL) and water (25 mL) and the organic solution was washed with saturated aqueous citric acid (25 mL), saturated aqueous NaHCO3 (25 mL) and water (25 mL), dried (MgSO4) and concentrated under reduced pressure. The residue was dissolved in dichloromethane (5 mL) and trifluoroacetic acid (5 mL) and stirred for one hour before the solvents were removed under reduced pressure, giving D-phenylglycine-4-hydroxypiperidinamide as its trifluoroacetate salt (150 mg, 43%).

LC/MS (Luna 2, Gradient 4): rt=2.64 min, 235 (MH)$^+$.

2-amino-5-cyanobenzoyl-D-phenylglycine 4-hydroxypiperidinamide

A solution of 2-amino-5-cyanobenzoic acid (170 mg, 1.0 mmol) in dimethylformamide (10 mL) was treated with 1-(3-dimethylaminopropyl)-3-ethylcarbodiimide hydrochloride (210 mg, 1.1 mmol) and 1-hydroxy-7-azabenzotriazole (150 mg, 1.1 mmol). After stirring for 10 minutes, D-phenylglycine 4-hydroxypiperidinamide trifluoroacetate salt (250 mg; 1.1 mmol) was added and the resulting solution stirred overnight at room temperature. The mixture was partitioned between ethyl acetate (25 mL) and water (25 mL) and the organic solution was washed with saturated aqueous citric acid (25 mL), saturated aqueous NaHCO$_3$ (25 mL) and water (25 mL), dried (MgSO$_4$) and concentrated under reduced pressure. The crude product was purified by column chromatography (ethyl acetate) to yield 2-amino-5-cyanobenzoyl-D-phenylglycine 4-hydroxypiperidinamide (90 mg, 23%).

1-(2-amino-5-(aminomethyl)benzoyl-D-phenylglycinyl 4-hydroxypiperidine dihydrochloride salt A solution of the nitrile in methanol (10 mL) and 36% hydrochloric acid (0.5 mL) was stirred over 10% palladium on carbon (20 mg) under an atmosphere of hydrogen for 16 hours. The mixture was filtered and the residue washed with methanol (10 mL) before concentrating the filtrate under reduced pressure. Purification by preparative HPLC afforded 2-amino-5-(aminomethyl)benzoyl-D-phenylglycine 4-hydroxy-piperidinamide dihydrochloride salt (30 mg, 33%).

$^1$H NMR (d$_4$ MeOH): 7.84 ppm (1H, s, Ar); 7.61–7.17 (7H, m, Ar); 6.85 (1H, d, J=8 Hz, Ar); 6.12 (1H, s, C$\underline{H}$Ph); 4.26 (1H, m, piperidine C(4)H); 3.99 (2H, s, C$\underline{H}_2$NH$_2$); 3.79 (2H, m, piperidine C(2)H and C(6)H); 3.42–3.08 (2H, m, piperidine C(2)H and C(6)H); 1.86–0.72 (4H, m, piperidine C(3)H$_2$ and C(5)H$_2$).

HPLC (Luna 2, Gradient 1): rt=2.49 minutes.

LC/MS (Luna 2, Gradient 4): rt=1.35 minutes, 366 (MH-NH$_3$)$^+$.

Example 72

3-(Aminomethyl)benzoyl-D-phenylglycine 1-(2-hydroxyphenyl)acetyl-2,3-dihydroindol-6-amide trifluoroacetate salt Prepared in a similar manner to Example 35, using (2-hydroxyphenyl)acetic acid.

$^1$H NMR (CD$_3$CN): 8.91 ppm (1H, s, OH), 8.30 (1H, s, NH), 7.94 (2H, br s, Ar), 7.73 (1H, d, J=10 Hz, Ar), 7.54–7.06 (12H, m, Ar & NH), 7.01 (1H, d, J=8 Hz, Ar), 6.74 (2H, m, Ar), 5.61 (1H, d, J=8 Hz, ArC$\underline{H}$), 4.21 (2H, t, J=8 Hz, dihydroindole C(2)H$_2$), 4.10 (2H, s, ArC$\underline{H}_2$N), 3.73 (2H, s, ArC$\underline{H}_2$CO), 3.10 (2H, d, J=8 Hz, dihydroindole C(3)H$_2$).

HPLC (Symmetry, Gradient 2): rt=6.24 minutes.

LC/MS (Luna 2, Gradient 4): rt=2.10 minutes, 535 (MH)$^+$.

Example 73

3-(Aminomethyl)benzoyl-D-phenylglycine 1-(3-hydroxyphenyl)acetyl-2,3-dihydroindol-6-amide trifluoroacetate salt Prepared in a similar manner to Example 35, using (3-hydroxyphenyl)acetic acid.

$^1$H NMR (d$_4$ MeOH): 8.21 ppm (1H, s, Ar), 7.71 (2H, br s, Ar), 7.50–7.16 (8H, m, Ar), 7.05–6.95 (2H, m, Ar), 6.64–6.50 (3H, m, Ar), 5.62 (1H, s, ArC$\underline{H}$), 4.09 (2H, s, ArC$\underline{H}_2$N), 4.04 (2H, t, J=8 Hz, dihydroindole C(2)H$_2$), 3.68 (2H, s, ArC$\underline{H}_2$CO), 2.91 (2H, d, J=8 Hz, dihydroindole C(3)H$_2$).

HPLC (Symmetry, Gradient 2): rt=5.95 minutes.

LC/MS (Luna 2, Gradient 4): rt=2.05 minutes, 535 (MH$^+$).

Example 74

3-(Aminomethyl)benzoyl-D-phenylglycine 1-(4-hydroxyphenyl)acetyl-2,3-dihydroindol-6-amide trifluoroacetate salt Prepared in a similar manner to Example 35, using (4hydroxyphenyl)acetic acid.

$^1$H NMR (d$_4$ MeOH): 8.32 ppm (1H, s, Ar), 8.04 (2H, br s, Ar), 7.66–7.34 (8H, m, Ar), 7.22–7.11 (3H, m, Ar), 6.80 (2H, d, J=10 Hz, Ar), 5.85 (1H, s, ArCH), 4.21 (2H, s, ArCH$_2$N), 4.15 (2H, t, J=8 Hz, dihydroindole C(2)H$_2$), 3.81 (2H, s, ArCH$_2$CO), 3.20 (2H, d, J=8 Hz, dihydroindole C(3)H$_2$).

HPLC (Symmetry, Gradient 2): rt=5.97 minutes.

LC/MS (Luna 2, Gradient 4): rt=2.02 minutes, 535 (MH$^+$).

Example 75

3-(Aminomethyl)benzoyl-D-phenylglycine 1-benzyl-3-acetylindol-5-amide trifluoroacetate salt Prepared in a similar fashion to Example 1, starting from 3-acetyl-5-amino-1-benzylindole, which was prepared as described below.

3-Acetyl-5-nitroindole and 3-acetyl-7-nitroindole

Prepared by the method described by Ottoni, Cruz and Kramer in *Tetrahedron Letters,* 40, 1999, 1117–1120, as a mixture of isomers.

3-Acetyl-1-benzyl-5-nitroindole and 3-acetyl-1-benzyl-7-nitroindole

Potassium carbonate (940 mg, 6.8 mmol) was added to a stirred solution of the above indoles (695 mg, 3.4 mmol) in dimethylformamide (30 mL). Benzyl bromide (0.61 mL, 5.1 mmol) was then added dropwise and the mixture left to stir over the weekend. The dimethylformamide was removed under reduced pressure and the residue partitioned between ethyl acetate (30 mL) and water (20 mL). The ethyl acetate layer was dried (MgSO$_4$) and evaporated to give the benzylamines as a golden oil.

3-Acetyl-5-amino-1-benzylindole and 3-acetyl-7-amino-1-benzylindole

A mixture of the indoles (1.0 g, 3.4 mmol), tin(II) chloride dihydrate (3.48 g, 15.4 mmol) and ethanol (20 mL) was heated at reflux, under an atmosphere of nitrogen, for 3 hours. The mixture was cooled and the solvent evaporated to give a brown oil. To this was added water (50 mL), which was then made basic with 1 N aqueous sodium hydroxide. The aqueous solution was then extracted with ethyl acetate (2×30 mL). The whole biphasic mixture was filtered through celite to remove tin salts, separated and the organic solvent dried (MgSO$_4$). The solvent was removed under reduced pressure to give a brown oil which was purified by flash chromatography on silica gel (hexane/ethyl acetate; 3:1) to afford, in order of elution, 3-acetyl-7-amino-1-benzylindole $^1$H NMR (CDCl$_3$): 7.67 ppm (1H, s, indole C(2)H); 7.39–7.13 (3H, m, Ph); 7.15 (2H, m, Ph); 7.05 (1H, t, J=6 Hz, indole C(5)H); 6.57 (1H, d, J=6.5 Hz, indole C(4)H); 6.41 (1H, d, J=6 Hz, indole C(6)H); 5.95 (2H, br s, NH$_2$); 5.27 (2H, s, PhCH$_2$); 2.50 (3H, s, CH$_3$)

and 3-acetyl-5-amino-1-benzylindole $^1$H NMR (CDCl$_3$): 8.08 ppm (1H, d, J=6 Hz, indole C(7)H); 7.50 (1H, s, indole C(2)H); 7.31–7.22 (3H, m, Ph); 7.05 (2H, m, Ph); 6.63 (1H, dd, J=6, 2 Hz, indole C(6)H); 6.45 (1H, s, indole 4-H); 5.25 (2H, s, PhCH$_2$); 3.62 (2H, br s, NH$_2$); 2.5 (3H, s, CH$_3$).

3-(Aminomethyl)benzoyl-D-phenylglycine 1-benzyl-3-acetylindol-5-amide trifluoroacetate salt $^1$H NMR (d$_4$ MeOH): 8.28 ppm (1H, s, Ar); 8.20 (1H, d, J=5 Hz, Ar); 7.97 (3H, m, Ar); 7.71–7.56 (4H, m, Ar); 7.47–7.19 (9H, m, Ar); 5.85 (1H, s, CHPh); 5.45 (2H, s, CH$_2$Ph); 4.21 (2H, CH$_2$NH$_2$); 2.53 (3H, s, CH$_3$).

HPLC (Luna 2, Gradient 1): rt=4.15 minutes.

HPLC (Symmetry, Gradient 2): rt=6.77 minutes.

LC/MS (Luna 2, Gradient 4): rt=2.48 minutes, 531 (MH)$^+$.

Example 76

3-(Aminomethyl)benzoyl-D-phenylglycine 1-benzyl-3-acetylindol-7-amide trifluoroacetate salt Prepared in a similar fashion to Example 1, starting from 3-acetyl-7-amino-1-benzylindole, which was prepared as described above.

$^1$H NMR (d$_4$ MeOH): 8.46 ppm (1H, s, Ar); 8.34 (1H, d, J=6 Hz, Ar); 8.11–7.95 (3H, m, Ar); 7.75–7.48 (4H, m, Ar); 7.46–7.12 (9H, m, Ar); 5.85 (1H, s, CHPh); 5.48 (2H, s, CH$_2$Ph); 4.21 (2H, s, CH$_2$NH$_2$); 2.62 (3H, s, CH$_3$).

HPLC (Luna 2, Gradient 1): rt=4.58 minutes.

HPLC (Symmetry, Gradient 2): rt=6.80 minutes.

LC/MS (Luna 2, Gradient 4): rt=2.80 minutes, 531 (MH)$^+$.

Example 77

3-(Aminomethyl)benzoyl-D-(4-hydroxyphenyl)glycine indan-5-amide trifluoroacetate salt Prepared in a similar fashion to Example 61, using (4-hydroxyphenyl)glycine and protecting as appropriate.

$^1$H NMR (d$_4$ MeOH): 8.00 ppm (2H, s, Ar); 7.72–7.55 (2H, m, Ar); 7.47 (3H, t, J=8.6 Hz, Ar); 7.31 (1H, d, J=7.5 Hz, Ar); 7.18 (1H, d, J=8 Hz, Ar); 6.86 (2H, d, J=8.6 Hz, Ar); 5.75 (1H, s, CHPh); 4.23 (2H, s, CH$_2$NH$_2$); 2.94 (4H, m, indane C(1)H$_2$ and C(3)H$_2$); 2.12 (2H, m, indane C(2)H$_2$).

HPLC (Luna 2, Gradient 1): rt=3.78 minutes.

HPLC (Symmetry, Gradient 2): rt=5.80 minutes.

LC/MS (Luna 2, Gradient 4): rt=1.83 minutes, 416 (MH)$^+$.

Example 78

3-(Aminomethyl)benzoyl-D/L-2-(N-formylamino) thiazol-4-yl]glycine 5-indanamide trifluoroacetate salt Prepared using the same method as described for Example 61 from D/L-α-(N-$^t$butyloxycarbonyl)-[2-(N-formylamino) thiazol-4-yl]glycine (synthesised as described below).

Ethyl α-azido-[2-(N-formylamino)thiazol-4-yl]acetate

A solution of ethyl[2-(N-formylamino)thiazol-4-yl]acetate (1 g, 0.0047 mol) in THF (10 mL) was stirred under argon at −78° C. and potassium bis(trimethylsilyl)amide (2.8 g, 0.014 mol) in THF (10 mL) was added. After stirring for 30 minutes, 2,4,6-triisopropylbenzenesulfonyl azide (3.6 g, 0.012 mol) was added as a solid in one portion. After 5 minutes, acetic acid (1.4 mL, 0.018 mol) was added and the mixture warmed to room temperature. The reaction mixture was then partitioned between ethyl acetate (100 mL) and water (100 mL), separated and the organic layer dried ($MgSO_4$). Evaporation of the solvent and purification of the residue by silica gel chromotography afforded the azide (0.95 g, 80%).

$^1$H NMR ($CDCl_3$): 8.78 ppm (1H, s, NHCHO); 6.98 (1H, s, C(5)H); 5.95 (1H, s, CHN$_3$); 4.18 (2H, m, CH$_2$CH$_3$); 1.20 (3H, m, CH$_2$CH$_3$).

Ethyl α-(N-$^t$butyloxycarbonylamino)-[2-(N-formylamino)thiazol-4-yl]acetate

Di-$^t$butyl dicarbonate (0.9 g, 0.004 mol) and 5% palladium on carbon (catalytic amount) were added to a solution of the azide (0.95 g, 0.0037 mol) in methanol (25 mL). The mixture was stirred at room temperature under an atmosphere of hydrogen for 8 hours. After this time the mixture was filtered through celite, washing through with methanol (25 mL). Evaporation of the solvent and purification of the residue by silica gel chromatography afforded the $^t$butyloxycarbonyl amine as a pale oily solid (1.1 g, 90%).

$^1$H NMR ($CDCl_3$): 8.53 ppm (1H, s, NHCHO); 6.89 (1H, s, C(5)H); 6.18 (1H, d, J=8 Hz, NHBoc); 5.38 (1H, d, J=8 Hz, CHN); 4.06 (2H, m, CH$_2$CH$_3$); 1.28 (9H, s, $^t$Bu); 1.12 (3H, m, CH$_2$CH$_3$).

D/L-α-N-$^t$butyloxycarbonyl-[2-(N-formylamino)thiazol-4-yl]glycine

A solution of the ester (1.1 g, 0.0031 g) in THF (25 mL) was treated with 1 M aqueous LiOH (5 ml, 0.005 mol) and heated at reflux for 1 hour. The solvent was removed under reduced pressure and the residue diluted with water (100 mL). The pH was reduced to 2 using 5% aqueous HCl and the aqueous phase was extracted with ethyl acetate (3×50 mL). The combined organic extracts were dried ($MgSO_4$) and concentrated under reduced pressure to afford the acid as a white solid (0.8 g, 84%).

$^1$H NMR (d$_4$ MeOH): 8.38 ppm (1H, s, NHCHO); 7.01 (1H, s, C(5)H); 5.21 (1H, s, CHN); 1.39 (9H, s, $^t$Bu).

3-(Aminomethyl)benzoyl-D/L-[2-(formylamino)thiazol-4-yl]glycine 5-indanamide trifluoroacetate salt $^1$H NMR (d$_4$ MeOH): 10.10 ppm (1H, s, NHCHO); 8.80 (1H, d, J=8 Hz, NH); 8.48 (1H, s, NHCHO); 7.97 (2H, br s, Ar); 7.58 (2H, m, Ar); 7.42 (1H, s, aminothiazole C(5)H); 7.37 (1H, d, J=7 Hz, indane C(6)H); 7.18 (1H, s, indane C(4)H); 7.10 (1H, d, J=7 Hz, indane C(7)H); 5.92 (1H, m, CHAr); 4.18 (2H, s, CH$_2$NH$_2$); 2.83 (4H, m, indane C(1)H$_2$ and C(3)H$_2$); 2.02 (2H, m, indane C(2)H$_2$)

HPLC (Luna 2, gradient 1): rt=3.71 minutes.

LC/MS (Luna 2, gradient 4): rt=2.05 minutes; 450 (MH)$^+$.

Example 79

3-(Aminomethyl)benzoyl-D/L-2-aminothiazol-4-ylglycine-5-indanamide bis(hydrochloride) salt Prepared from D/L-α-N-$^t$butyloxycarbonyl-[2-(N-formylamino)thiazol-4-yl]glycine and synthesised using the method of Example 80 except that the final deprotection was effected using 3 M aqueous HCl in THF, in order to remove both the $^t$butyloxycarbonyl and formyl protecting groups.

$^1$H NMR (d$_4$ MeOH): 7.87 ppm (2H, m, Ar); 7.51 (1H, m, Ar); 7.48 (1H, t, J=7 Hz, (aminomethyl)benzoyl C(3)H); 7.40 (1H, s, aminothiazole C(5)H); 7.20 (1H, d, J=8 Hz, indane C(6)H); 7.05 (1H, d, J=8 Hz, indane C(7)H); 6.73 (1H, s, indane C(4)H); 5.78 (1H, s, CHAr); 4.12 (2H, s, CH$_2$NH$_2$); 2.79 (4H, m, indane C(1)H$_2$ and C(3)H$_2$); 2.00 (2H, m, indane C(2)H$_2$)

HPLC (Luna 2, gradient 1): rt=3.21 minutes.

LC/MS (Luna 2, gradient 4): rt=1.78 minutes; 422 (MH)$^+$.

Examples 80–95 were prepared in the same manner as example 1, using the indicated amine.

Example 80

3-(Aminomethyl)benzoyl-D-phenylglycine 8-acetoxyquinolin-2-amide trifluoroacetate salt From 8-acetoxyquinolin-2-amine.

$^1$H NMR (D$_2$O): 8.12–7.16 (14H, m, Ar); 5.50 (1H, s, α-CH); 4.00 (2H, br s, CH$_2$NH$_2$); 2.13 (3H, s, CH$_3$).

HPLC (Symmetry, Gradient 2): rt=6.02 minutes.

LC/MS (Luna 2, Gradient 4): rt=1.99 minutes, 469 (MH)$^+$.

Example 81

3-(Aminomethyl)benzoyl-D-phenylglycine 3-ethoxycarbonyl-4,5-dimethylthiophen-2-amide trifluoroacetate salt From 3-ethoxycarbonyl-4,5-dimethylthiophen-2-amine.

$^1$H NMR (d$_6$ DMSO): 11.32 (1H, NHAr); 9.37 (1H, d, J=7 Hz, NHCOAr); 8.10 (2H, br s, NH$_2$); 7.98 (2H, s, Ar); 7.58–7.27 (7H, m, Ar); 5.95 (1H, d, J=7 Hz, α-CH); 4.20 (2H, m, CH$_2$N & CH$_2$CH$_3$); 2.19 & 2.11 (2×3H, 2×s, 2×ArCH$_3$); 1.17 (3H, t, J=7 Hz, CH$_2$CH$_3$).

HPLC (Luna 2, Gradient 1): rt=4.72 minutes.

LC/MS (Luna 2, Gradient 4): rt=2.23 minutes, 466 (MH)$^+$.

Example 82

3-(Aminomethyl)benzoyl-D-phenylglycine 5-acetyl-4-methylthiazol-2-amide trifluoroacetate salt From 5-acetyl-4-methylthiazol-2-amine.

$^1$H NMR (d$_3$ acetonitrile): 8.92 (1H, d, J=6 Hz, NHCH); 7.95 (2H, br s, NH$_2$); 7.78–7.65 (2H, m, Ar); 7.40–7.14 (7H, m, Ar); 5.61 (1H, d, J=6 Hz, α-CH); 3.87 (2H, br d, J=5 Hz, CH$_2$NH$_2$); 2.32 (3H, s, CH$_3$); additional methyl group concealed by solvent peak between 2.20 and 2.30 ppm.

HPLC (Luna 2, Gradient 1): rt=3.55 minutes.

LC/MS (Luna 2, Gradient 4): rt=1.78 minutes, 423 (MH)$^+$.

Example 83

3-(Aminomethyl)benzoyl-D-phenylglycine 5-phenylthiazol-2-amide trifluoroacetate salt From 5-phenylthiazol-2-amine.

$^1$H NMR (d$_3$ acetonitrile): 12.81 (1H, s, H-bonded NHAr); 9.07 (1H, d, J=6 Hz, NHCO); 8.12 (2H, br s, CH$_2$NH$_2$); 8.07–7.84 (3H, m, Ar); 7.62–7.28 (12H, m, Ar); 5.88 (1H, d, J=6 Hz, α-CH); 4.10 (2H, m, CH$_2$NH$_2$).

HPLC (Luna 2, Gradient 1): rt=4.36 minutes.

LC/MS (Luna 2, Gradient 4): rt=2.23 minutes, 443 (MH)$^+$.

Example 84

3-(Aminomethyl)benzoyl-D-phenylglycine 4,5-dimethyl-thiazol-2-amide trifluoroacetate salt From 4,5-dimethylthiazol-2-amine.

$^1$H NMR (d$_4$ methanol): 9.01 (0.5H due to partial exchange, d, J=6 Hz, NHCH); 7.99–7.93 (2H, m, Ar); 7.61–7.43 (7H, m, Ar); 5.85 (1H, s superimposed upon d, J=6 Hz, α-CH); 4.18 (2H, s, CH$_2$NH$_2$); 2.29 & 2.18 (2×3H, 2×s, 2× CH$_3$).

HPLC (Luna 2, Gradient 1): rt=3.67 minutes.

LC/MS (Luna 2, Gradient 4): rt=1.96 minutes, 395 (MH)$^+$.

Example 85

3-(Aminomethyl)benzoyl-D-phenylglycine 4-methyl-5-ethoxycarbonylthiazol-2-amide trifluoroacetate salt From 4-methyl-5-ethoxycarbonylthiazol-2-amine.

$^1$H NMR (d$_3$ acetonitrile): 8.20 (1H, d, J=6 Hz, NHCH); 8.02 (1H, s, Ar); 7.76 (1H, d, J=7 Hz, Ar); 7.52–7.30 (7H, m, Ar); 5.78 (1H, d, J=6 Hz, α-CH); 4.16 (2H, q, J=6 Hz, CH$_2$CH$_3$); 4.11 (2H, s, CH$_2$NH$_2$); 2.45 (3H, s, ArCH$_3$); 1.21 (3H, t, J=6 Hz, CH$_2$CH$_3$).

HPLC (Luna 2, Gradient 1): rt=3.73 minutes.

LC/MS (Luna 2, Gradient 4): rt=2.13 minutes, 453 (MH)$^+$.

Example 86

3-(Aminomethyl)benzoyl-D-phenylglycine 3-cyano-4-methyl-5-ethoxycarbonylthiophen-2-amide trifluoroacetate salt From 3-cyano-4-methyl-5-ethoxycarbonylthiophen-2-amine.

$^1$H NMR (d$_3$ acetonitrile): 8.57 (1H, d, J=6 Hz, NHCH); 8.40 (1H, Ar); 8.12 (1H, d, J=7 Hz, Ar); 7.81–7.59 (7H, m, Ar); 6.15 (1H, d, J=6 Hz, α-CH); 4.45 (2H, q, J=7 Hz); 4.40 (2H, s, CH$_2$NH$_2$); 2.68 (3H, s, ArCH$_3$); 1.48 (3H, t, J=7 Hz, CH$_2$CH$_3$).

HPLC (Luna 2, Gradient 1): rt=4.305 minutes.

LC/MS (Luna 2, Gradient 4): rt=2.15 minutes, 477 (MH)$^+$.

Example 87

3-(Aminomethyl)benzoyl-D-phenylglycine 4-(methoxycarbonylmethyl)-5-methylthiazol-2-amide trifluoroacetate salt From 4-methoxycarbonyl-5-methylthiazol-2-amine.

$^1$H NMR (d$_3$ acetonitrile): 8.02–7.97 (2H, m, Ar & NHCH); 7.87 (1H, d, J=8 Hz, Ar); 7.59–7.33 (7H, m, Ar); 7.21 (2H, br s, NH$_2$); 5.81 (1 h, d, J=6 Hz, α-CH); 4.18 (2H, s, CH$_2$NH-2); 3.58 (3H, s, CO$_2$CH$_3$); 3.55 (2H, s, CH$_2$CO); 2.31 (3H, s, ArCH$_3$).

HPLC (Luna 2, Gradient 1): rt=3.54 minutes.

LC/MS (Luna 2, Gradient 4): rt=2.05 minutes, 453 (MH)$^+$.

Example 88

3-(Aminomethyl)benzoyl-D-phenylglycine 5-t-butyl-2-methoxycarbonylthiophen-3-amide trifluoroacetate salt From 5-t-butyl-2-methoxycarbonylthiophen-3-amine.

$^1$H NMR (d$_3$ acetonitrile): 10.42 (1H, s, NHAr); 8.21 (1H, d, J=6 Hz, NHCH); 8.04 (1H, s, Ar); 7.80–7.65 (5H, m, 3× Ar & NH$_2$); 7.52–7.30 (7H, m, Ar); 5.68 (1H, d, J=6 Hz, α-CH); 4.12 (2H, s, CH$_2$NH$_2$); 3.72 (3H, s, CO$_2$CH$_3$); 1.29 (9H, s, C(CH$_3$)$_3$).

HPLC (Luna 2, Gradient 1): rt=4.93 minutes.

LC/MS (Luna 2, Gradient 4): rt=2.48 minutes, 480 (MH)$^+$.

Example 89

3-(Aminomethyl)benzoyl-D-phenylglycine 5,6-dihydro-3-methoxycarbonyl-4H-cyclopenta(b)thiophen-2-amide trifluoroacetate salt From 5,6-dihydro-3-methoxycarbonyl-4H-cyclopenta(b)thiophen-2-amine.

$^1$H NMR (d$_3$ acetonitrile): 8.30 (1H, d, J=6 Hz, NHCH); 8.04 (1H, Ar); 7.85 (1H, d, J=8 Hz, Ar); 7.62–7.30 (7H, m, Ar); 5.80 (1H, d, J=6 Hz, α-CH); 4.16 (2H, s, CH$_2$NH$_2$); 3.72 (3H, s, CH$_3$); 2.87 & 2.84 (2×2H, 2×t, 2×J=6 Hz, CH$_2$CH$_2$CH$_2$); 2.30 (2H, pentet, J=6 Hz, CH$_2$CH$_2$CH$_2$).

HPLC (Symmetry, Gradient 2): rt=6.56 minutes.

LC/MS (Luna 2, Gradient 4): rt=2.26 minutes, 464 (MH)$^+$.

Example 90

3-(Aminomethyl)benzoyl-D-phenylglycine 3-ethoxycarbonyl-tetrahydrobenzo(b)thiophene-2-amide trifluoroacetate salt From 3-ethoxycarbonyl-tetrahydrobenzo(b)thiophene-2-amine.

$^1$H NMR (d$_3$ acetonitrile): 8.25 (0.6H due to partial exchange, d, J=6 Hz, NHCH); 8.06 (1H, s, Ar); 7.86 (1H, d, J=7 Hz, Ar); 7.52–7.23 (7H, m, Ar); 5.79 (1H, s superimposed upon d, J=6 Hz, α-CH); 4.18–4.04 (4H, m, CH$_2$NH$_2$ & CH$_2$CH$_3$); 2.65 & 2.50 (2×2H, 2×br s, CH$_2$CH$_2$CH$_2$CH$_2$); 1.82–1.70 (4H, m, CH$_2$CH$_2$CH$_2$CH$_2$).

HPLC (Luna 2, Gradient 1): rt=5.15 minutes.

LC/MS (Luna 2, Gradient 4): rt=2.42 minutes, 492 (MH)$^+$.

Example 91

3-(Aminomethyl)benzoyl-D-phenylglycine 2-acetyl-5-phenylthiophen-3-amide trifluoroacetate salt From 2-acetyl-5-phenylthiophen-3-amine.
$^1$H NMR ($d_3$ acetonitrile): 8.34 (1H, s, thiophene CH); 8.30 (1H, d, J=6 Hz, NHCH); 8.12 (1H, s, Ar); 7.85 (1H, d, J=8 Hz, Ar); 7.70–7.33 (12H, m, Ar); 5.75 (1H, d, J=6 Hz, α-CH); 4.16 (2H, s, CH$_2$NH$_2$); 2.35 (3H, s, CH$_3$).
HPLC (Luna 2, Gradient 1): rt=4.75 minutes.
LC/MS (Luna 2, Gradient 4): rt=2.64 minutes, 484 (MH)$^+$.

Example 92

3-(Aminomethyl)benzoyl-D-phenylglycine 3-benzyloxycarbonyl-tetrahydrobenzo(b)thiophene-2-amide trifluoroacetate salt From 3-benzyloxycarbonyl-tetrahydrobenzo(b)thiophene-2-amine.
$^1$H NMR ($d_3$ acetonitrile): 8.02–7.95 (2H, m, 1×Ar & N HCH); 7.92 (1H, d, J=7 Hz, Ar); 7.72–7.32 (12H, m, Ar); 5.81 (1H, d, J=6 Hz, α-CH); 5.22 (2H, s, CH$_2$Ar); 4.18 (2H, s, CH$_2$NH$_2$); 2.70 & 2.59 (2×2H, 2× t, 2×J=5 Hz C H$_2$CH$_2$CH$_2$CH$_2$); 1.82–1.68 (4H, m, CH$_2$CH$_2$CH$_2$CH$_2$).
HPLC (Luna 2, Gradient 1): rt=5.40 minutes.
LC/MS (Luna 2, Gradient 4): rt=2.75 minutes, 554 (MH)$^+$.

Example 93

3-(Aminomethyl)benzoyl-D-phenylglycine N-methylanilide trifluoroacetate salt

From N-methyl aniline.
$^1$H NMR ($d_4$ MeOH): 7.70 (2H, s, Ar); 7.45–7.30 (3H, m, Ar); 7.21 (3H, m, Ar); 7.08 (3H, m, Ar); 6.90 (3H, m, Ar); 5.50 (1H, s, CHPh); 3.97 (2H, s, CH$_2$NH$_2$); 3.14 (3H, s, Me)
HPLC (Luna 2, Gradient 1): rt=3.91 minutes.
HPLC (Symmetry, Gradient 2): rt=5.88 minutes.
LC/MS (Luna 2, Gradient 4): rt=1.72 minutes, 374 (MH)$^+$.

Example 94

3-(Aminomethyl)benzoyl-D-phenylglycine N-methylindan-5-amide trifluoroacetate salt From 5-N-methylaminoindane, prepared as described below.

5-N-methylaminoindane

Formic acid (98%, 0.90 mL, 1.10 g, 24 mmol) was added dropwise to a stirred solution of acetic anhydride (1.85 mL, 2.0 g, 20 mmol) in THF (20 mL) at 0° C. After the addition the solution was heated at 60° C. for 2 hours. The mixture was cooled to room temperature and THF (2 mL) was added, followed by a solution of 5-aminoindane (1.0 g, 7.5 mmol) dissolved in THF (4 mL) and allowed to stir overnight.
The solvent was evaporated under reduced pressure to give a cream-coloured solid. This was dissolved in THF (10 mL), cooled to 0° C., and borane:dimethyl sulphide complex in THF (2.0M, 8.45 mL, 17 mmol) was added dropwise. The resulting mixture was heated at reflux for 3 hours before being cooled to 0° C. Methanol (5 mL) was added and the mixture stirred for 1 hour. Ethereal HCl (1.0 M, 10 mL) was added and the mixture was warmed to 60° C. briefly, before being cooled back to room temperature. Methanol 20 mL) was added and the solvents evaporated under reduced pressure. The solid residue was made basic (pH>12) with aqueous sodium hydroxide (2 N), then extracted with ether (2×20 mL). The combined dried extracts were absorbed onto silica and purified by flash chromatography using dichloromethane as eluent to give the amine as a straw-coloured oil upon evaporation (900 mg, 81%).

3-(Aminomethyl)benzoyl-D-phenylglycine N-methylindan-5-amide trifluoroacetate salt $^1$H NMR ($d_4$ MeOH): 7.91 (2H, m, Ar); 7.65 (1H, m, Ar); 7.55 (1H, m, Ar); 7.35–7.20 (4H, m, Ar); 7.1 (2H, m, Ar); 6.87 (2H, br s, Ar); 5.73 (2H, d, J=7 Hz, CHPh); 4.18 (2H, s, CH$_2$NH$_2$); 3.30 (3H, s, Me); 2.95 (2H, t, J=7.5 Hz, indane C(1)H$_2$ or C(3)H$_2$); 2.85 (2H, t, J=7.5 Hz, indane C(1)H$_2$ or C(3)H$_2$); 2.13 (2H, quintet, J=7.5 Hz, indane C(2)H$_2$).
HPLC (Luna 2, Gradient 1): rt=4.11 minutes.
HPLC (Symmetry, Gradient 2): rt=6.30 minutes.
LC/MS (Luna 2, Gradient 4): rt=2.10 minutes, 414 (MH)$^+$.

Example 95

3-(Aminomethyl)benzoyl-D-phenylglycine 1-methoxycarbonylmethyl-2,3-dihydroindol-6-amide trifluoroacetate salt From 6-amino-1-methoxycarbonylmethylindoline, prepared as described below.

6-amino-1-methoxycarbonylmethylindoline

A suspension of 6-nitroindoline (1.0 g, 6.1 mmol) and sodium hydrogen carbonate (0.6 g, 7.1 mmol) in DMF (60 ml) was stirred at room temperature. Methyl bromoacetate (0.68 mL, 1.09 g, 7.1 mmol) was added slowly and the mixture was heated at 90° C. for 1 hour. The mixture was cooled, the solvents evaporated under reduced pressure, and the residue partitioned between ethyl acetate (40 mL) and water (20 mL). The organic layer was dried over MgSO$_4$ and then evaporated to give an orange solid. The solid was dissolved in methanol (100 ml), 5% Pd/C (50 mg, cat.) was added and the suspension was stirred under an atmosphere of hydrogen for 2 hours, during which time the yellow colour disappeared. The catalyst was removed by filtration through celite and the solvent was evaporated to give the amine as a brown oil (0.95 g, 75%).

3-(Aminomethyl)benzoyl-D-phenylglycine 1-methoxycarbonylmethyl-2,3-dihydroindol-6-amide trifluoroacetate salt $^1$H NMR ($d_4$ MeOH): 7.75 (2H, br s, Ar); 7.38 (4H, m, Ar); 7.20 (3H, m, Ar); 6.75 (2H, d, J=8 Hz, Ar); 6.55 (2H, m, Ar); 5.61 (1H, s, CHPh); 3.96 (3H, s, CH$_3$); 3.75 (2H, s, CH$_2$NH$_2$); 3.5 (2H, s, CH$_2$CO$_2$Me); 3.3 (2H, t, J=8.0 Hz, indoline C(2)H$_2$); 2.73 (2H, t, J=8.0 Hz, indoline C(3)H$_2$).
HPLC (Symmetry, Gradient 2): rt=6.06 minutes.
LC/MS (Luna 2, Gradient 4): rt=1.83 minutes, 473 (MH)$^+$.

Example 96

3-(Aminomethyl)benzoyl-D/L-phenylglycine 3-morpholinoyl-tetrahydrobenzo(b)thiophene-2-amide trifluoroacetate salt

3-(BOC-Aminomethyl)benzoyl-D-phenylglycine 3-(hydroxycarbonyl)tetrahydrobenzo(b)thiophen-2-amide A solution of 3-(BOC-aminomethyl)benzoyl-D/L-phenylglycine 3-benzyloxycarbonyl-tetrahydrobenzo(b)thiophen-2-amide (a protected form of example 92 and an intermediate in its synthesis) (1.00 g, 1.6 mmol) in methanol (20 mL) was stirred over 10% palladium on carbon under a hydrogen atmosphere for two hours. The mixture was filtered and the methanol evaporated under reduced pressure to afford the acid (0.86 g, quant.) which was used without further purification.

$^1$H NMR (d$_6$ DMSO): 11.91 (1H, br s CO$_2$H); 9.46 (1H, d, J=6 Hz, NHCH); 7.90 (1H, d, J=6 Hz, NHBoc); 7.86 (1H, s, Ar); 7.55–7.32 (7H, m, Ar); 5.92 (1H, d, J=6 Hz, α-CH); 4.20 (2H, d, J=6 Hz, CH$_2$NH$_2$); 2.71 & 2.59 (2×2H, 2×br s, CH$_2$CH$_2$CH$_2$CH$_2$); 1.72–1.60 (4H, m, CH$_2$CH$_2$CH$_2$CH$_2$); 1.34 (9H, s, C(CH$_3$)$_3$)-3-(Aminomethyl)benzoyl-D-phenylglycine 3-morpholinoyl-tetrahydrobenzo(b)thiophene-2-amide trifluoroacetate salt.

A solution of the carboxylic acid (55 mg, 0.10 mmol) in DMF (2 mL) was stirred at room temperature and diisopropylethylamine (52 µL, 39 mg, 0.30 mmol), morpholine (87 µL, 87 mg, 1.00 mmol) and O-(7-azabenzotriazol-1-yl)-N',N',N',N'-tetramethyluronium hexafluorophosphate (114 mg, 0.30 mmol). The reaction was allowed to stir at room temperature until HPLC indicated complete consumption of starting material (5 days). Ethyl acetate (20 mL) was then added, and the solution extracted with 1N HCl (20 mL); sodium bicarbonate (sat., aq., 20 mL) and water (20 mL); dried over MgSO$_4$, concentrated under reduced pressure, and purified by flash column chromatography.

A solution of the amide in dichloromethane (2 mL) was treated with trifluoroacetic acid (2 mL) for an hour. The excess TFA and dichloromethane were evaporated and the residue purified by trituration with diethyl ether to afford 3-(Aminomethyl)benzoyl-D/L-phenylglycine 3-morpholinoyl-tetrahydrobenzo(b)thiophene-2-amide as its trifluoroacetate salt.

$^1$H NMR (d$_3$ acetonitrile): 9.02 ppm (1H, s, NHAr); 7.85–7.70 (3H, m, NHCH & 2×Ar); 7.50–7.25 (7H, m, Ar); 5.64 (1H, d, J=6 Hz, α-CH); 4.03 (2H, br s, CH$_2$NH$_2$); 3.40–2.89 (8H, m, 2×CH$_2$O & CH$_2$CH$_2$CH$_2$CH$_2$); 2.52–2.45 & 2.30–2.15 (2×2H, 2×m, 2× morpholine CH$_2$N); 1.75–1.60 (4H, m, CH$_2$CH$_2$CH$_2$CH$_2$).

HPLC (Luna 2, Gradient 1): rt=3.68 minutes.

LC/MS (Luna 2, Gradient 4): rt=1.91 minutes, 533 (MH)$^+$.

Examples 97–101 were prepared from 3-(N-BOC-aminomethyl)benzoyl-D/L-phenylglycine 3-(hydroxycarbonyl) tetrahydrobenzo(b)thiophen-2-amide in the same manner as example 96, using the indicated amine.

Example 97

3-(Aminomethyl)benzoyl-D-phenylglycine 3-benzylamido-tetrahydrobenzo(b)thiophen-2-amide trifluoroacetate salt Prepared from benzylamine.

$^1$H NMR (d$_3$ acetonitrile): 8.02–7.91 (3H, m, 2×Ar & NHCH); 7.60–7.25 (12H, m, Ar); 6.73 (1H, t, J=5 Hz, NHBn); 5.79 (1H, d, J=6 Hz, α-CH); 4.41 (2H, d, J=5 Hz, CH$_2$Ar); 4.16 (2H, s, CH$_2$NH$_2$); 2.71 & 2.62 (2×2H, 2×br s, CH$_2$CH$_2$CH$_2$CH$_2$); 1.85–1.76 (4H, m, CH$_2$CH$_2$CH$_2$CH$_2$).

HPLC (Luna 2, Gradient 1): rt=4.47 minutes.

LC/MS (Luna 2, Gradient 4): rt=2.40 minutes, 553 (MH)$^+$.

Example 98

3-(Aminomethyl)benzoyl-D-phenylglycine 3-pyridylmethylamido-tetrahydrobenzo(b)thiophen-2-amide bis-trifluoroacetate salt Prepared from 3-pyridylmethylamine.

$^1$H NMR (d$_3$ acetonitrile): 8.37 (1H, s, Ar); 8.34 (1H, d, J=5 Hz, NHCH); 8.25 (1H, d, J=6 Hz, Ar); 7.78–7.14 (11H, m, Ar); 6.81 (1H, t, J=5 Hz, NHBn); 5.58 (1H, d, J=5 Hz, α-CH); 4.42 (2×1H, 2×dd, 2×J=8 Hz, 5 Hz, NHCH$_2$Ar); 4.04 (2H, s, CH$_2$NH$_2$); 2.58 & 2.46 (2×2H, 2×br s, CH$_2$CH$_2$CH$_2$CH$_2$); 1.62–1.53 (4H, m, CH$_2$CH$_2$CH$_2$CH$_2$).

HPLC (Luna 2, Gradient 1): rt=3.32 minutes.

LC/MS (Luna 2, Gradient 4): rt=1.59 minutes, 554 (MH)$^+$.

Example 99

3-(Aminomethyl)benzoyl-D-phenylglycine 3-piperidinoyl-tetrahydrobenzo(b)thiophen-2-amide trifluoroacetate salt Prepared from piperidine.

$^1$H NMR (d$_3$ acetonitrile): 9.20 (1H, s, NHAr); 8.15–7.26 (9H, m, Ar); 5.82 (1H, br s, α-CH); 4.06 (2H, br s, CH$_2$NH$_2$); 3.20–1.15 (18H, m, piperidyl and cyclohexyl protons)

HPLC (Luna 2, Gradient 1): rt=3.94 minutes.

LC/MS (Luna 2, Gradient 4): rt=2.02 minutes, 531 (MH)$^+$.

Example 100

3-(Aminomethyl)benzoyl-D-phenylglycine 3-cyclopropylmethylamido-tetrahydrobenzo(b)thiophen-2-amide trifluoroacetate salt Prepared from cyclopropylmethylamine.

$^1$H NMR (d$_3$ acetonitrile): 7.76–7.58 (3H, m, 2×Ar & NHCH); 7.40–7.12 (7H, m, Ar); 6.18 (1H, t, J=5 Hz, NHBn); 5.50 (1H, d, J=5 Hz, α-CH); 4.00 (2H, br s, CH$_2$NH$_2$); 2.92 (2H, t, J=5 Hz, CH$_2$CPr); 2.48 & 2.40 (2×2H, 2×br s, CH$_2$CH$_2$CH$_2$CH$_2$); 1.65–1.55 (4H, m, CH$_2$CH$_2$CH$_2$CH$_2$); 0.81–0.65, 0.28–0.17 & 0.05 to −0.05 (1H, 2H & 2H, 3×m, cPr protons).

HPLC (Luna 2, Gradient 1): rt=4.19 minutes.

LC/MS (Luna 2, Gradient 4): rt=2.18 minutes, 517 (MH)$^+$.

Example 101

3-(Aminomethyl)benzoyl-D-phenylglycine 3-(1,3-dimethylbutyl)amido-tetrahydrobenzo(b)thiophen-2-amide trifluoroacetate salt Prepared from racemic 1,3-dimethylbutylamine.

$^1$H NMR ($d_3$ acetonitrile): 7.88–7.75 (3H, m, 2×Ar & NHCH); 7.48–7.25 (7H, m, Ar); 5.97 (1H, d, J=5 Hz, α-CH); 5.68 & 5.65 (2×0.5H, 2×d, 2×J=4 Hz, NHHex); 4.12–4.02 (2H, m, CH$_2$NH$_2$); 4.01–3.90 (1H, m, CH$_3$CHNH); 2.59 & 2.47 (4H, m, CH$_2$CH$_2$CH$_2$CH$_2$); 1.73–1.62 (4H, m, CH$_2$CH$_2$CH$_2$); 1.53–0.70 (12H, m, remaining hexyl protons).

HPLC (Luna 2, Gradient 1): rt=4.63 minutes.

LC/MS (Luna 2, Gradient 4): rt=2.53 minutes, 547 (MH)$^+$.

Example 102

3-(Aminomethyl)benzoyl-D-phenylglycine 3-carboxy-tetrahydrobenzo(b)thiophen-2-amide trifluoroacetate salt A solution of 3-(BOC-aminomethyl)benzoyl-D/L-phenylglycine 3-(hydroxycarbonyl)tetrahydrobenzo(b)thiophen-2-amide (50 mg, 0.9 mmol), the compound from which examples 96–100 were made, in dichloromethane (2 mL) was treated with trifluoroacetic acid (2 mL) for an hour at room temperature. The solvents were evaporated and the residue triturated with diethyl ether to afford the title compound as an off-white solid.

$^1$H NMR ($d_3$ acetonitrile): 8.25–8.17 (2H, m, Ar); 8.01 (1H, d, J=6 Hz, NHCH); 7.75–7.52 (7H, m, Ar); 6.00 (1H, d, J=6 Hz, α-CH); 4.35 (2H, br s, CH$_2$NH$_2$); 2.85 & 2.71 (2×2H, 2×br s, CH$_2$CH$_2$CH$_2$CH$_2$); 1.92–1.80 (4H, m, CH$_2$CH$_2$CH$_2$CH$_2$.

HPLC (Luna 2, Gradient 1): rt=4.31 minutes.

LC/MS (Luna 2, Gradient 4): rt=2.07 minutes, 464 (MH)$^+$.

Examples 103–118 were prepared from the intermediate 3-(N-BOC-aminomethyl)benzoyl-D/L-phenylglycine 2,3-dihydroindol-6-amide, described for example 35, using the indicated carboxylic acid or derivative, using standard chemical methods and protecting other functionality where required.

Example 103

3-(Aminomethyl)benzoyl-D/L-phenylglycine 1-(3-acetylamino)propionyl-2,3-dihydroindol-6-amide hydrochloride salt From N-acetyl-β-alanine.

$^1$H NMR (CD$_3$CN): 8.78 ppm (1H, br s, NH); 8.40 (1H, br s, NH); 7.82 (2H, br s, Ar); 7.72 (1H, d, J=10 Hz, Ar); 7.62–7.53 (2H, m, Ar); 7.51 (1H, d, J=10 Hz, Ar); 7.45–7.27 (4H, m, Ar); 7.20 (1H, d, J=9 Hz, indoline C(4)H or C(5)H); 7.10 (1H, d, J=9 Hz, indoline C(4)H or C(5)H ); 6.68 (1H, br s, NH); 5.71 (1H, d, J=8 Hz, CHPh); 4.00 (2H, t, J=9 Hz, indoline C(2)H$_2$); 3.83 (2H, s, CH$_2$NH$_2$); 3.42 (2H, q, J=6 Hz, AcNHCH$_2$CH$_2$); 3.06 (2H, t, J=11 Hz, indoline C(3)H$_2$); 2.54 (2H, t, J=6 Hz, AcNHCH$_2$CH$_2$); 1.86 (3H, s, CH$_3$CO).

HPLC (Symmetry C8, Gradient 2): rt=5.57 min.

LC/MS (Luna 2, Gradient 4): rt=1.62 min, 514 (MH)$^+$.

Example 104

3-(Aminomethyl)benzoyl-D/L-phenylglycine 1-amidoacetyl-2,3-dihydroindol-6-amide hydrochloride salt From malonic acid monoamide.

$^1$H NMR (CD$_3$CN): 8.66 ppm (1H, br s, NH); 8.35 (1H, br s, NH); 7.94 (1H, s, Ar); 7.85 (1H, s Ar); 7.78–7.65 (3H, m, Ar); 7.60–7.52 (2H, m, Ar); 7.50 (1H, d, J=8 Hz, Ar); 7.46–7.31 (4H, m, Ar); 7.25 (1H, d, J=10 Hz, indoline C(4)H or C(5)H); 7.12 (1H, d, J=10 Hz, indoline C(4)H or C(5)H); 6.77 (1H, br s, C(O)NH$_a$H$_b$); 5.85 (1H, br s, C(O)NH$_a$H$_b$); 5.67 (1H, d, J=9 Hz, CHPh); 4.08 (2H, t, J=10 Hz, indoline C(2)H$_2$); 3.86 (2H, s, CH$_2$NH$_2$); 3.38 (2H, s, C(O)CH$_2$C(O)); 3.11 (2H, t, J=10 Hz, indoline C(3)H$_2$).

HPLC (Symmetry C8, Gradient 2): rt=5.12 min.

LC/MS (Luna 2, Gradient 4): rt=1.67 min, 486 (MH)$^+$.

Example 105

3-(Aminomethyl)benzoyl-D/L-phenylglycine 1-(γ-L-aspartoyl)-2,3-dihydroindol-6-amide bis(hydrochloride) salt From N-BOC-aspartic acid 1-t-butyl ester.

$^1$H NMR (D$_2$O): 7.89 ppm (1H, d, J=8 Hz, Ar); 7.62 (1H, s, Ar); 7.60 (1H, d, J=8 Hz, Ar); 7.52–7.11 (7H, m, Ar); 6.95–6.72 (2H, m, indoline C(4)H and C(5)H); 5.53 (1H, s, CHPh); 4.44 (1H, m, CH(NH$_2$)CO$_2$H); 4.01 (2H, s, CH$_2$NH$_2$); 3.85–3.50 (2H, m, indoline C(2)H$_2$); 3.00–2.55 (4H, m, indoline C(3)H$_2$ and C(O)CH$_2$CH(NH$_2$)CO$_2$H).

HPLC (Symmetry C8, Gradient 2): rt=5.26 min.

LC/MS (Luna 2, Gradient 4): rt=1.29 min, 516 (MH)$^+$.

Example 106

3-(Aminomethyl)benzoyl-D/L-phenylglycine 1-(β-glutamoyl)-2,3-dihydroindol-6-amide bis(hydrochloride) salt From N-BOC-β-glutamic acid 5-benzyl ester.

$^1$H NMR (D$_2$O): 7.83 ppm (1H, d, J=10 Hz, Ar); 7.63 (2H, br s, 3-(aminomethyl)-phenyl C(2)H and C(6)H); 7.55–7.17 (6H, m, Ar); 6.88 (1H, br s, Ar); 6.82 (1H, d, J=9 Hz, indoline C(4)H or C(5)H); 6.64 (1H, d, J=8 Hz, indoline C(4)H or C(5)H); 5.55 (1H, s, CHPh); 4.00 (2H, s, CH$_2$NH$_2$); 3.80 (1H, quintet, J=6 Hz, CHNH$_2$); 3.30–3.06 (2H, br m, indoline C(2)H$_2$); 2.71 (2H, d, J=6 Hz, β-glutamoyl C(2)H$_2$ or C(4)H$_2$); 2.60–2.25 (4H, br m, indoline C(3)H$_2$ and β-glutamoyl C(2)H$_2$ or C(4)H$_2$).

HPLC (Symmetry C8, Gradient 2): rt=5.39 min.

LC/MS (Luna 2, Gradient 4): rt=1.18 min, 530 (MH)$^+$.

Example 107

3-(Aminomethyl)benzoyl-D/L-phenylglycine 1-(L-homoprolinoyl)-2,3-dihydroindol-6-amide bis(hydrochloride) salt From N-BOC-homoproline.

$^1$H NMR (D$_2$O): 7.76 ppm (1H, s, Ar); 7.56 (2H, br s, Ar); 7.40–7.14 (7H, m, Ar); 6.83–6.67 (2H, m, indoline C(4)H and C(5)H); 5.43 (1H, s, CHPh); 3.92 (2H, s, CH$_2$NH$_2$); 3.61–3.53 (1H, m, pyrrolidine C(2)H); 3.42–3.29 (1H, m, indoline C(2)H$_2$); 3.05 (2H, t, J=6 Hz, pyrrolidine C(5)H$_2$); 2.55–2.41 (4H, m, C(O)CH$_2$Pyrrolidine and indoline C(3)

H$_2$); 1.98–1.87 (1H, m, pyrrolidine C(3)H or C(4)H); 1.80–1.66 (2H, m, pyrrolidine C(3)H or C(4)H); 1.48–1.35 (1H, m, pyrrolidine C(3)H or C(4)H).

HPLC (Symmetry C8, Gradient 2): rt=5.36 min.
LC/MS (Luna 2, Gradient 4): rt=1.32 min, 512 (MH)$^+$.

Example 108

3-(Aminomethyl)benzoyl-D/L-phenylglycine 1-(D-pipecoloyl)-2,3-dihydroindol-6-amide bis(hydrochloride) salt From N-BOC-D-pipecolic acid.
$^1$H NMR (D$_2$O): 8.05 ppm (1H, s, Ar); 7.80 (2H, br s, Ar); 7.72–7.30 (7H, m, Ar); 7.03 (1H, d, J=8 Hz, indoline C(4)H or C(5)H); 6.88 (1H, d, J=8 Hz, indoline C(4)H or C(5)H); 5.72 (1H, s, CHPh); 4.18 (2H, s, CH$_2$NH$_2$); 3.84–3.53 (2H, m, indoline C(2)H$_2$); 3.43–2.60 (7H, m, indoline C(3)H$_2$, piperidine C(2)H$_2$, C(3)H and C(6)H$_2$); 2.00–1.48 (4H, m, piperidine C(4)H$_2$ and C(5)H$_2$).

HPLC (Symmetry C8, Gradient 2): rt=5.38 min.
LC/MS (Luna 2, Gradient 4): rt=1.24 min, 512 (MH)$^+$.

Example 109

3-(Aminomethyl)benzoyl-D/L-phenylglycine 1-(trans-2-aminocyclohexanoyl)-2,3-dihydroindol-6-amide bis(hydrochloride) salt From N-BOC-trans-2-aminocyclohexane carboxylic acid.
$^1$H NMR (D$_2$O): 7.78 (1H, d, J=9 Hz, Ar); 7.48 (2H, br s, Ar); 7.36–6.95 (7H, m, Ar); 6.67 (1H, d, J=8 Hz, indoline C(4)H or C(5)H); 6.62 (1H, d, J=8 Hz, indoline C(4)H or C(5)H); 5.32 (1H, s, CHPh); 3.88 (2H, s, CH$_2$NH$_2$); 3.77–3.41 (2H, m, indoline C(2)H$_2$); 3.14 (1H, td, J=12, 5 Hz, cHex C(2)H); 2.64–2.42 (2H, m, indoline C(3)H$_2$); 2.32 (1H, br s, cHex C(1)H); 1.74 (1H, br d, J=11 Hz, cHex H); 1.62 (1H, br s, cHex H); 1.43 (2H, br d, J=12 Hz, cHex H's); 1.25–0.82 (4H, m, cHex H's).

HPLC (Symmetry C8, Gradient 2): rt=5.25 min.
LC/MS (Luna 2, Gradient 4): rt=2.80 min, 526 (MH)$^+$.

Example 110

3-(Aminomethyl)benzoyl-D/L-phenylglycine 1-(cis-2-aminocyclohexanoyl)-2,3-dihydroindol-6-amide bis(hydrochloride) salt From N-BOC-cis-2-aminocyclohexane carboxylic acid.
$^1$H NMR (D$_2$O): 7.80 (1H, d, J=11 Hz, Ar); 7.53 (1H, br s, Ar); 7.49 (1H, d, J=8 Hz, Ar); 7.38–7.27 (3H, m, Ar); 7.25–7.11 (4H, m, Ar); 6.71 (1H, d, J=10 Hz, indoline C(4)H or C(5)H); 6.60 (1H, d, J=10 Hz, indoline C(4)H or C(5)H); 5.44 (1H, s, CHPh); 3.86 and 3.80 (2H, AB quartet, J=14 Hz, CH$_2$NH$_2$); 3.46–3.28 (3H, m, indoline C(2)H$_2$ and cHex C(2)H); 2.54–2.38 (3H, m, indoline C(3)H$_2$ and cHex C(1)H); 1.75–1.60 (1H, m, cHex H); 1.48–1.15 (6H, m, cHex H's); 1.10–0.97 (1H, m, cHex H).

HPLC (Symmetry C8, Gradient 2): rt=5.14 min.
LC/MS (Luna 2, Gradient 4): rt=2.72 min, 526 (MH)$^+$.

Example 111

3-(Aminomethyl)benzoyl-D/L-phenylglycine 1-(piperidin-4-ylacetyl)-2,3-dihydroindol-6-amide bis-trifluoroacetate salt From piperidin-4-ylacetic acid.
$^1$H NMR (D$_2$O): 8.01 (1H, s, NHAr); 7.70 (2H, s, Ar); 7.52–7.31 (10H, m, Ar); 7.12 & 6.96 (2×1H, 2×d, J=6 Hz, Ar); 5.51 (1H, s, α-CH); 4.12 (2H, s, CH$_2$NH$_2$); 3.94 (2H, t, J=7 Hz, indoline NCH$_2$); 3.31 (1H, d, J=10 Hz, CH$_2$C=O); 3.01 (2H, t, J=7 Hz, indoline ArCH$_2$); 2.99–2.83, 2.40–2.32, 2.08–1.94, 1.90–1.80 & 1.39–1.18 (2H, 2H, 1H, 2H & 2H, 5×m, piperidyl ring protons).

HPLC (Luna 2, Gradient 1): rt=5.06 minutes.
LC/MS (Luna 2, Gradient 4): rt=1.45 minutes, 526 (MH)$^+$.

Example 112

3-(Aminomethyl)benzoyl-D/L-phenylglycine 1-[(4-aminomethyl)phenylacetyl]-2,3-dihydroindol-6-amide bis-trifluoroacetate salt From 4-(BOC-aminomethyl)phenylacetic acid.
$^1$H NMR (d$_6$ DMSO): 10.30 (1H, s, NHAr); 8.85 (1H, d, J=8 Hz, NHCOAr); 8.28 & 8.01 (2×1H, 2×s, Ar); 7.96 (1H, d, J=8 Hz, Ar); 7.68–7.14 (13H, m, Ar); 5.81 (1H, d, J=8 Hz, α-CH); 4.24–4.01 (6H, m, 3×CH$_2$NH$_2$); 3.84 (2H, s, ArCH$_2$); 3.06 (2H, t, J=7 Hz, indoline ArCH$_2$).

HPLC (Symmetry, Gradient 2): rt=5.51 minutes.
LC/MS (Luna 2, Gradient 4): rt=1.62 minutes, 548 (MH)$^+$.

Example 113

3-(Aminomethyl)benzoyl-D/L-phenylglycine 1-[(4-acetylaminomethyl)phenylacetyl]-2,3-dihydroindol-6-amide trifluoroacetate salt From 4-(acetylaminomethyl)phenylacetic acid.
$^1$H NMR (D$_2$O): 7.90 (1H, s, NH); 7.59–7.21 (10H, m, Ar); 6.98 & 6.85 (2×2H, 2×d, 2×J=9 Hz, para-substituted ring protons); 6.78 & 6.75 (2×1H, 2×d, 2×J 6 Hz, indoline CHCH); 5.48 (1H, s, α-CH); 4.11 & 4.01 (2×2H, 2×s, 2×ArCH$_2$N); 3.67 (2H, t, J=6 Hz, indoline CH$_2$N); 3.37 (2H, s, CH$_2$CO); 2.62 (2H, t, J=6 Hz, indoline ArCH$_2$); 1.81 (3H, s, CH$_3$).

HPLC (Symmetry, Gradient 2): rt=5.87 minutes.
LC/MS (Luna 2, Gradient 4): rt=1.94 minutes, 590 (MH)$^+$.

Example 114

3-(Aminomethyl)benzoyl-D/L-phenylglycine 1-[(4-isopropyl)phenylacetyl]-2,3-dihydroindol-6-amide trifluoroacetate salt From 4-(isopropyl)phenylacetic acid.
$^1$H NMR (d$_3$ acetonitrile): 9.06 (1H, s, NHAr); 8.34 (1H, s, Ar); 8.06 (1H, d, J=7 Hz, NHCOAr); 8.01–7.04 (15H, Ar); 5.71 (1H, d, J=6 Hz, α-CH); 4.17–4.06 (4H, m, 2×CH$_2$N); 3.70 (2H, s, CH$_2$CO); 3.08 (2H, t, J=7 Hz, indoline ArCH$_2$); 2.90 (1H, septet, J=7 Hz, CHMe$_2$); 1.19 (6H, d, J=7 Hz, 2×CH$_3$).

HPLC (Symmetry, Gradient 2): rt=6.89 minutes.
LC/MS (Luna 2, Gradient 4): rt=2.64 minutes, 561 (MH)$^+$.

Example 115

3-(Aminomethyl)benzoyl-D/L-phenylglycine 1-[(3,4-dihydroxyphenyl)acetyl]-2,3-dihydroindol-6-amide trifluoroacetate salt From 3,4-dihydroxyphenylacetic acid.
$^1$H NMR (d$_6$ DMSO): 10.50 (1H, s, H-bonded OH); 9.00–8.90 (2H, m, Ar); 8.90 (1H, br s, OH); 8.45 (1H, s, NH); 8.25 (2H, br s, NH$_2$); 8.16 (1H, s, NH); 8.07 (1H, d, J=8 Hz, Ar); 7.76–7.46 (9H, m, Ar); 6.79–6.71 (2H, m, Ar); 6.59 (1H, d, J=8 Hz, Ar); 5.93 (1H, d, J=7 Hz, α-CH); 4.27–4.12 (4H, m, 2×CH$_2$N); 3.70 (1H, s, CH$_2$CO); 3.15 (2H, t, J=7 Hz, indoline ArCH$_2$).
HPLC (Symmetry, Gradient 2): rt=5.90 minutes.
LC/MS (Luna 2, Gradient 4): rt=1.94 minutes, 551 (MH)$^+$.

Example 116

3-(Aminomethyl)benzoyl-D/L-phenylglycine 1-(4-aminocyclohexyl)acetyl-2,3-dihydroindol-6-amide bis-trifluoroacetate salt From 4-(BOC-aminocyclohexyl)acetic acid.
$^1$H NMR (d$_3$ acetonitrile): 9.04 (1H, s, NHAr); 8.15 (1H, Ar); 7.90–6.85 (11H, m, Ar); 5.54 (1H, d, J=6 Hz, α-CH);); 3.95–3.74 (5H, m, 2×CH$_2$NH$_2$ & CHNH$_2$); 2.87 (2H, t, J=7 Hz, indoline ArCH$_2$); 2.65–1.84 (11H, m, cyclohexyl protons & adjacent CH$_2$).
HPLC (Luna 2, Gradient 1): rt=3.23 minutes.
LC/MS (Luna 2, Gradient 4): rt=1.45 minutes, 540 (MH)$^+$.

Example 117

3-(Aminomethyl)benzoyl-D/L-phenylglycine 1-(isobutyrylaminoacetyl)-2,3-dihydroindol-6-amide trifluoroacetate salt From N-isobutyryl glycine.
$^1$H NMR (d$_4$ MeOH): 8.23 (1H, s, Ar); 8.85 (2H, m, Ar); 7.50 (4H, m, Ar); 7.30 (4H, m, Ar); 7.10 (1H, d, J=8 Hz, Ar); 5.72 (1H, s, CHPh); 4.10–4.01 (6H, m, CH$_2$NH$_2$, CH$_2$indoline, COCH$_2$); 3.10 (2H, t, J=8 Hz, CH$_2$indoline); 2.50 (1H, septet, J=7 Hz, CH(Me)$_2$); 1.10 (6H, d, J=7 Hz, CH(CH$_3$)$_2$).
HPLC (Luna 2, Gradient 1): rt=3.39 minutes.
HPLC (Symmetry, Gradient 2): rt=5.75 minutes.
LC/MS (Luna 2, Gradient 4): rt=1.72 minutes, 528 (MH)$^+$ Example 118

3-(Aminomethyl)benzoyl-D/L-phenylglycine 1-[hydroxyacetyl(aminoacetyl)]-2,3-dihydroindol-6-amide trifluoroacetate salt From N-(2-benzyloxyacetyl)glycine.
$^1$H NMR (d$_4$ MeOH): 8.15 (1H, s, Ar); 7.78 (2H, m, Ar); 7.42 (4H, m, Ar); 7.32 (4H, m, Ar); 7.0 (1H, d, J=8 Hz, Ar); 5.65 (1H, s, CHPh); 4.05–3.95 (6H, m, CH$_2$NH$_2$, indoline C(2)H$_2$, COCH$_2$NH); 3.88 (2H, s, COCH$_2$OH); 3.10 (2H, t, J=8.5 Hz, indoline C(3)H$_2$).

HPLC (Luna 2, Gradient 4): rt=3.805 minutes.
LC/MS (Luna 2, Gradient 4): rt=1.51 minutes, 516 (MH)$^+$.

Example 119

3-(Aminomethyl)benzoyl-D/L-phenylglycine 1-methanesulfonyl-2,3-dihydroindol-6-amide trifluoroacetate salt A solution of 3-(N-BOC-aminomethyl)benzoyl-D/L-phenylglycine 2,3-dihydroindolyl-6-amide (100 mg, 0.2 mmol) in dichloromethane (5 mL) was treated with triethylamine (42 μl, 0.3 mmol) and methanesulfonyl chloride (23.2 μl, 0.3 mmol). The mixture was stirred overnight at room temperature, then diluted with further dichloromethane (10 mL). The solution was washed with water (2×15 mL) and brine (10 mL). The organic solvent was dried over magnesium sulfate and the solvent removed under reduced pressure. The crude amide was dissolved in dichloromethane (5 mL) and treated with trifluoroacetic acid (1 mL) for 2 hours, until HPLC indicated no starting material remained. The mixture was evaporated under reduced pressure, and the resulting gum triturated with diethyl ether (2×30 mL) to afford an off-white solid, which was isolated by filtration. Purification via preparative HPLC yielded the title compound as a white solid (38 mg, 32%).
$^1$H NMR (d$_6$ DMSO): 10.48 ppm (1H, s); 8.89 (1H, d, J=6 Hz, Ar); 8.03 (3H, br s, NH$_3$$^+$); 7.95 (1H, d, J=8 Hz, Ar); 7.66 (1H, s); 7.63–7.30 (7H, m, Ar); 7.18 (1H, d, J=8 Hz, Ar); 5.85 (1H, d, J=7 Hz, CHPh); 4.09 (2H, s, CH$_2$NH$_2$); 3.92 (2H, t, J=8 Hz, indolyl CH$_2$); 3.04 (2H, t, J=8 Hz, indolyl CH$_2$); 2.97 (3H, s, CH$_3$).
HPLC (Luna 2, Gradient 4): rt=2.37 minutes
LC/MS (Luna 2, Gradient 4): rt=1.70 minutes, 479 (MH)$^+$.

Examples 120–125 were prepared in a similar manner to Example 119, using the indicated sulphonyl chloride.

Example 120

3-(Aminomethyl)benzoyl-D/L-phenylglycine 1-ethanesulfonyl-2,3-dihydroindol-6-amide trifluoroacetate salt From ethanesulfonyl chloride.
$^1$H NMR (d$_6$ DMSO): 10.51 ppm (1H, s); 8.95 (1H, d, J=7 Hz, Ar); 8.20 (2H, s(br), NH$_2$); 8.08 (1H, s); 9.00 (1H, d, J=8 Hz); 7.68–7.32 (9H, m, Ar); 7.21 (1H, d, J=9 Hz); 5.90 (1H, d, J=8 Hz, CHPh); 4.14 (2H, s, CH$_2$NH$_2$); 4.01 (2H, t, J=8 Hz, indolyl CH$_2$); 3.21 (2H, q, J=7.5 Hz, CH$_2$CH$_3$); 3.09 (2H, t, J=9 Hz, indolyl CH$_2$); 1.24 (3H, t, J=7.5 Hz, CH$_3$).
HPLC (Luna 2, Gradient 4): rt=2.65 minutes
LC/MS (Luna 2, Gradient 4): rt=1.78 minutes, 493 (MH)$^+$.

Example 121

3-(Aminomethyl)benzoyl-D/L-phenylglycine 1-benzenesulfonyl-2,3-dihydroindol-6-amide trifluoroacetate salt From benzenesulfonyl chloride.
$^1$H NMR (d$_6$ DMSO): 10.40 ppm (1H, s); 8.87 (1H, d, J=7.5 Hz, Ar); 7.93 (3H, m); 7.88 (1H, d, J=8 Hz, Ar); 7.83 (1H, d, J=1.5 Hz, Ar); 7.71 (2H, d, J=9 Hz); 7.51–7.26 (10H, m, Ar); 7.10 (1H, d, J=4 Hz, Ar); 6.96 (1H, d, J=8 Hz); 5.79

(1H, d, J=8 Hz, CHPh); 4.00 (2H, s, CH$_2$NH$_2$); 3.78 (2H, t, J=8 Hz, indolyl CH$_2$); 2.73 (2H, t, J=8 Hz, indolyl CH$_2$).

HPLC (Luna 2, Gradient 4): rt=3.02 minutes

LC/MS (Luna 2, Gradient 4): rt=2.03 minutes, 541 (MH)$^+$.

Example 122

3-(Aminomethyl)benzoyl-D/L-phenylglycine 1-benzylsulfonyl-2,3-dihydroindol-6-amide trifluoroacetate salt From α-toluenesulfonyl chloride.

$^1$H NMR (d$_6$ DMSO): 10.43 ppm (1H, s); 8.92 (1H, d, J=7.5 Hz, Ar); 8.22 (2H, br s, NH$_2$); 8.05 (1H, s); 7.97 (1H, d, J=7.5 Hz, Ar); 7.61–7.25 (13H, m); 7.14 (1H, d, J=8 Hz, Ar); 5.88 (1H, d, J=8 Hz, CHPh); 4.53 (2H, s, CH$_2$Ph); 4.10 (2H, s, CH$_2$NH$_2$); 3.80 (2H, t, J=8.5 Hz, indolyl CH$_2$); 2.94 (2H, t, J=8.5 Hz, indolyl CH$_2$).

HPLC (Luna 2, Gradient 4): rt=3.07 minutes

LC/MS (Luna 2, Gradient 4): rt=2.05 minutes, 555 (MH)$^+$.

Example 123

3-(Aminomethyl)benzoyl-D/L-phenylglycine 1-N,N-dimethylsulfamoyl-2,3-dihydroindol-6-amide trifluoroacetate salt From dimethylsulfamoyl chloride.

$^1$H NMR (d$_6$ DMSO): 10.42 ppm (1H, s); 8.90 (1H, d, J=8 Hz, Ar); 8.14 (2H, br s, NH$_2$); 8.02 (1H, s, Ar); 7.94 (1H, d, J=7.5 Hz); 7.63–7.51 (5H, m, Ar); 7.41–7.34 (3H, m, Ar); 7.23 (1H, d, J=8 Hz); 7.12 (1H, d, J=8 Hz); 5.85 (1H, d, J=7.5 Hz, CHPh); 4.08 (2H, d, J=5 Hz, CH$_2$NH$_2$); 3.90 (2H, t, J=8.5 Hz, indolyl CH$_2$); 3.03 (2H, t, J=8.5 Hz, indolyl CH$_2$); 2.79 (6H, s, 2×CH$_3$).

HPLC (Luna 2, Gradient 4): rt=2.73 minutes

LC/MS (Luna 2, Gradient 4): rt=1.83 minutes, 506 (MH)$^+$.

Example 124

3-(Aminomethyl)benzoyl-D/L-phenylglycine 1-(8-quinolyl-sulfonyl)-2,3-dihydroindol-6-amide trifluoroacetate salt From 8-quinolinesulfonyl chloride.

$^1$H NMR (d$_6$ DMSO): 10.30 ppm (1H, s); 9.01 (1H, d, J=2.5 Hz, Ar); 8.88 (1H, d, J=8 Hz, Ar); 8.48 (2H, d, J=7 Hz, Ar); 8.27 (1H, d, J=7 Hz, Ar); 8.03 (2H, br s, NH$_2$); 7.74 (1H, d, J=7 Hz, Ar); 7.73–7.33 (10H, m, Ar); 7.06 (1H, d, J=7 Hz); 6.98 (1H, d, J=7 Hz); 4.70–4.56 (2H, m, indolyl CH$_2$); 4.09 (2H, d, J=5.5 Hz, CH$_2$NH$_2$); 2.99 (2H, t, J=8.5 Hz, indolyl CH$_2$).

HPLC (Luna 2, Gradient 4): rt=2.55 minutes

LC/MS (Luna 2, Gradient 4): rt=1.95 minutes, 592 (MH)$^+$.

Example 125

3-(Aminomethyl)benzoyl-D/L-phenylglycine 1-(2-naphthyl-sulfonyl)-2,3-dihydroindol-6-amide trifluoroacetate salt From 2-naphthalenesulfonyl chloride.

$^1$H NMR (d$_6$ DMSO): 10.52 ppm (1H, s); 9.00 (1H, d, J=7.5 Hz, Ar); 8.61 (1H, s, Ar); 8.17 (2H, br s, NH$_2$); 8.11–7.99 (6H, m, Ar); 7.80 (1H, d, J=7.5 Hz); 7.72–7.38 (9H, m, Ar); 7.11 (1H, d, J=7.5 Hz); 7.02 (1H, d, J=7.5 Hz); 5.90 (1H, d, J=7.5 Hz, CHPh); 4.12 (2H, s, CH$_2$NH$_2$); 3.96 (2H, t, J=8 Hz, indolyl CH$_2$); 2.85 (2H, t, J=8 Hz, indolyl CH$_2$).

HPLC (Luna 2, Gradient 4): rt=2.82 minutes

LC/MS (Luna 2, Gradient 4): rt=2.20 minutes, 591 (MH)$^+$.

Examples 126–128 were prepared from 3-(N-BOC-aminomethyl)benzoyl-D/L-phenylglycine 2,3-dihydroindolyl-6-amide in a similar manner as example 119, except that the indicated chloroformate was used in place of the sulphonyl chloride.

Example 126

3-(Aminomethyl)benzoyl-D/L-phenylglycine 1-methoxycarbonyl-2,3-dihydroindol-6-amide trifluoroacetate salt From methyl chloroformate.

$^1$H NMR (d$_6$ DMSO): 10.48 ppm (1H, s); 8.88 (1H, d, J=7.5 Hz); 8.17 (2H, br s, NH$_2$); 8.04 (1H, s); 7.96 (1H, d, J=7.5 Hz, Ar); 7.63–7.28 (8H, m, Ar); 7.12 (1H, d, 8 Hz); 5.87 (1H, d, J=7.5 Hz, CHPh); 4.10 (2H, d, J=4.5 Hz, CH$_2$NH$_2$); 3.95 (2H, t, J=8.5 Hz, indolyl CH$_2$); 3.73 (3H, s, CH$_3$); 3.02 (2H, t, J=8.5 Hz, indolyl CH$_2$).

HPLC (Luna 2, Gradient 4): rt=2.35 minutes

LC/MS (Luna 2, Gradient 4): rt=1.80 minutes, 459 (MH)$^+$.

Example 127

3-(Aminomethyl)benzoyl-D/L-phenylglycine 1-phenoxy-carbonyl-2,3-dihydroindol-6-amide trifluoroacetate salt From phenyl chloroformate.

$^1$H NMR (d$_6$ DMSO): 10.42 ppm (1H, s); 8.87 (1H, d, J=7.5 Hz, Ar); 8.16 (2H, br s, NH$_2$); 8.02 (1H, s, Ar); 7.94 (1H, d, J=7.5 Hz, Ar); 7.60–7.18 (13H; m, Ar); 5.85 (1H, d, J=7.5 Hz, CHPh); 4.21 (2H, br s, indolyl CH$_2$); 4.09 (2H, d, J=4 Hz, CH$_2$NH$_2$); 3.12 (2H, t, J=7.5 Hz, indolyl CH$_2$).

HPLC (Luna 2, Gradient 4): rt=2.71 minutes

LC/MS (Luna 2, Gradient 4): rt=2.15 minutes, 521 (MH)$^+$.

Example 128

3-(Aminomethyl)benzoyl-D/L-phenylglycine 1-allyloxy-carbonyl-2,3-dihydroindol-6-amide trifluoroacetate salt From allyl chloroformate.

$^1$H NMR (d$_6$ DMSO): 10.40 ppm (1H, s); 8.87 (1H, d, J=7.5 Hz, Ar); 8.16 (2H, br s, NH$_2$); 8.04 (1H, s, Ar); 7.96 (1H, d, J=8 Hz, Ar); 7.61–7.28 (8H, m, Ar); 7.13 (1H, d, J=8 Hz, Ar); 6.10–5.95 (1H, m, CH=CH$_2$); 5.35 (1H, dd, J=17

Hz, 1.5 Hz, CH=C$\underline{H}_2$); 5.24 (1H, dd, J=10.5 Hz, 1.5 Hz, CH=C$\underline{H}_2$); 4.67 (2H, d, J=4.5 Hz, OCH$_2$); 4.10 (2H, d, J=4 Hz, C$\underline{H}_2$NH$_2$); 3.99 (2H, t, J=8.5 Hz, indolyl CH$_2$); 3.06 (2H, t, J=8.5 Hz, indolyl CH$_2$).

HPLC (Luna 2, Gradient 4): rt=2.55 minutes

LC/MS (Luna 2, Gradient 4): rt=1.98 minutes, 485 (MH)$^+$.

Example 129

3-(Aminomethyl)benzoyl-D/L-phenylglycine 1-amido-2,3-dihydroindol-6-amide trifluoroacetate salt A solution of 3-(N-BOC-aminomethyl)benzoyl-D/L-phenylglycine 2,3-dihydroindolyl-6-amide (150 mg, 0.3 mmol) in anhydrous tetrahydrofuran (5 mL) was treated under argon with trimethylsilylisocyanate (81.2 μl, 0.6 mmol). The mixture was stirred overnight. The off-white precipitate was collected by filtration, and dissolved in dichloromethane (10 mL). The solution was treated with trifluoroacetic acid (2 mL) for 4 hours until no starting material remained by HPLC. The solvent was evaporated under reduced pressure, and trituration of the residue with diethyl ether (3×20 mL) afforded the title compound as an off white solid (136 mg, 81.3%).

$^1$H NMR (d$_6$ DMSO): 10.32 ppm (1H, s); 8.84 (1H, d, J=8 Hz, Ar); 8.15 (2H, br s, NH$_2$); 8.02 (2H, d, J=12 Hz); 7.98 (1H, d, J=8 Hz, Ar); 7.63–7.31 (8H, m, Ar); 7.03 (1H, d, J=8 Hz); 6.29 (2H, s, C(O)NH$_2$); 5.86 (1H, d, J=8 Hz, CHPh); 4.10 (2H, d, J=5 Hz, C$\underline{H}_2$NH$_2$); 3.85 (2H, t, J=8.5 Hz, indolyl CH$_2$); 3.03 (2H, t, J=8.5 Hz, indolyl CH$_2$).

HPLC (Luna 2, Gradient 4): rt=2.09 minutes

LC/MS (Luna 2, Gradient 4): rt=1.13 minutes, 444 (MH)$^+$.

Example 130

3-(Aminomethyl)benzoyl-D/L-phenylglycine 1-benzyl-2,3-dihydroindol-6-amide trifluoroacetate salt To a stirred suspension of 3-(N-BOC-aminomethyl)benzoyl-D/L-phenylglycine 2,3-dihydroindolyl-6-amide (100 mg, 0.20 mmol) and sodium hydrogen carbonate (40 mg, 0.47 mmol) in DMF (10 mL) at room temperature was added a solution of benzyl bromide (60 μL, 85 mg, 0.5 mmol) in DMF (5 mL). The mixture was heated at 65° C. for 1 hour and allowed to cool overnight. The solvent was removed under reduced pressure and the residue partitioned between water (15 mL) and ethyl acetate (30 mL). The organic layer was dried over MgSO$_4$ and evaporated under reduced pressure to give a golden oil. The oil was dissolved in dichloromethane (20 mL) and treated with TFA (4 mL) overnight. The solvent was evaporated to give an oil, which was purified by preparative HPLC to give an off-white solid (57 mg, 47%).

$^1$H NMR (d$_4$ MeOH): 8.20 (2H, d, J=9 Hz, Ar); 7.81 (3H, m, Ar); 7.57 (9H, m, Ar); 7.27 (2H, m, Ar); 7.12 (1H, d, J=8 Hz, Ar); 6.03 (1H, s, CHPh); 5.50 (2H, s, CH$_2$Ph); 4.41 (2H, s, C$\underline{H}_2$NH$_2$); 3.60 (2H, t, J=7.5 Hz, indoline C(2)H$_2$); 3.15 (2 H, t, J=7.5 Hz, indoline C(3)H$_2$).

HPLC (Luna 2, Gradient 4): rt=4.00 minutes.

HPLC (Symmetry, Gradient 2): rt=6.62 minutes.

LC/MS (Luna 2, Gradient 4): rt=2.26 minutes, 491 (MH)$^+$.

Example 131

3-(Aminomethyl)benzoyl-D/L-4-methylphenylglycine indan-5-amide hydrochloride salt N-Formyl-5-aminoindane To a solution of 5-aminoindane (7.53 g, 56.5 mmol) in DMF (100 mL) was added formic acid (2.2 mL, 58.3 mmol), 1-(3-dimethylaminopropyl)-3-ethylcarbodiimide hydrochloride (10.94 g, 57 mmol) and diisopropylethylamine (19.7 mL, 0.11 mol). The resulting solution was stirred overnight and then partitioned between saturated aqueous citric acid (100 mL) and ethyl acetate (200 mL). The organic layer was separated and washed with aqueous sodium bicarbonate solution (100 mL) and water (3×100 mL), then concentrated under reduced pressure to give the formamide as a thick oily solid (8.5 g, 93%).

Indan-5-isonitrile

To a solution of N-formyl-5-aminoindane (12 g, 74.5 mmol) in dichloromethane (100 mL) was added triethylamine (23 mL, 0.17 mol) and the solution was cooled to 0° C. under nitrogen. Phosphorous oxychloride (7 mL, 75 mmol) was added dropwise over 10 minutes, keeping the temperature at 0° C. The mixture was stirred at this temperature for 1 hour. A solution of sodium carbonate (15.6 g, 0.18 mol) in water (50 mL) was then added dropwise, keeping the temperature below 30° C. The mixture was diluted with water (100 mL) and then separated. The aqueous layer was extracted with dichloromethane (2×50 mL) and the combined organic extracts then washed with brine (200 mL), dried over magnesium sulphate and concentrated under reduced pressure. The crude oil was purified by vacuum distillation to give the product as a clear oil which solidified at low temperature (7.8 g, 72%); bp. 100–105° C. (0.05 mBar).

$^1$H NMR (CDCl$_3$): 7.10 (4H, m, Ar); 2.82 (4H, t, J=8 Hz, C(1)H$_2$, C(3)H$_2$); 2.03 (2H, quintet, J=8 Hz, C(2)H$_2$).

3-(BOC-aminomethyl)benzoyl-D/L-N-(2,4-dimethoxybenzyl)-4-methylphenylglycine indan-5-amide A solution of p-tolualdehyde (168 mg, 1.4 mmol) and 2,4-dimethoxybenzyl-amine (207 μL, 230 mg, 1.4 mmol) in dichloromethane (1 mL) was allowed to stand overnight. The solution was diluted to 5 mL with dichloromethane and dried over magnesium sulfate. The solvent was decanted off, the solids rinsed with dichloromethane (2×1 mL) and the solution diluted further to 10 mL. 3-(BOC-aminomethyl) benzoic acid (350 mg, 1.4 mmol) and indane-5-isonitrile (4 mL of a 5 g/100 mL solution in dichloromethane, 200 mg, 1.4 mmol) were added. The solution was stirred under argon for 14 days before being evaporated under reduced pressure onto silica gel (5 g). Purification by Biotage Flash 40 chromatography, eluting with 2:1 to 1:1 hexane:ethyl acetate afforded 3-(BOC-aminomethyl)benzoyl-D/L-N-(2,4-dimethoxybenzyl)-4-methylphenylglycine indan-5-amide as a white foamy solid (297 mg, 32%).

3-(Aminomethyl)benzoyl-D/L-4-methylphenylglycine indan-5-amide hydrochloride salt A solution of 3-(BOC-aminomethyl)benzoyl-D/L-N-(2,4-dimethoxybenzyl)-4-methylphenylglycine indan-5-amide (290 mg, 0.43 mmol) in dichlormethane (3 mL) was stirred at room temperature and trifluoroacetic acid (3 mL) was added. After 90 minutes the excess trifluoroacetic acid and dichlormethane were removed under reduced pressure. The purple oily residue was taken up in methanol (2 mL) and purified by SCX acid ion-exchange chromatography, eluting with methanol and then 5%-10% 2 N $NH_3$/methanol in dichlormethane, to afford 3-(aminomethyl)benzoyl-D/L-4-methylphenylglycine indan-5-amide as its free base. This was taken up in acetonitrile (5 mL) and water (10 mL) was added, followed by 5% HCl (aq.) to afford a pale yellow solution. The acetonitrile was removed under reduced pressure and the aqueous solution was lyophilised to afford 3-(aminomethyl)benzoyl-D/L-4-methylphenylglycine indan-5-amide as its hydrochloride salt (92 mg, 0.20 mmol, 48%).

$^1$H NMR ($CD_3CN$): 8.47 ppm (1H, br s, Ar); 7.72 (1H, s, Ar); 7.67–7.53 (2H, m, Ar); 7.46–7.28 (4H, m, Ar); 7.13 (2H, d, J=10 Hz, tolyl C(2)H's or C(3)H's); 7.07 (1H, d, J=10 Hz, indane C(6)H or C(7)H); 5.55 (1H, s, C$\underline{H}$Tol); 3.74 (2H, s, C$\underline{H}_2NH_2$); 2.81 (2H, t, J=6 Hz, indane C(1)$H_2$ or C(3)$H_2$); 2.77 (2H, t, J=6 Hz, indane C(1)$H_2$ or C(3)$H_2$); 2.27 (3H, s, $CH_3$Ar); 2.10–1.95 (2H, m, indane C(2)$H_2$).

HPLC (Luna 2, Gradient 1): rt=4.53 min.

LC/MS (Luna 2, Gradient 4): rt=2.13 min, 414 $(MH)^+$.

Examples 132–146 were prepared in a similar manner, starting with the indicated aldehyde.

Example 132

3-(Aminomethyl)benzoyl-D/L-2-chlorophenylglycine indan-5-amide hydrochloride salt From 2-chlorobenzaldehyde.

$^1$H NMR ($d_6$ DMSO): 10.27 ppm (1H, br s, C(O)N$\underline{H}$-Indane); 9.08 (1H, br d, J=10 Hz, C(O)N$\underline{H}$CHAr); 7.92 (1H, s, Ar); 7.78 (1H, d, J=10 Hz, Ar); 7.57 (1H, s, Ar); 7.55–7.44 (3H, m, Ar); 7.42–7.30 (4H, m, Ar); 7.14 (1H, d, J=9 Hz, indane C(6)H or C(7)H); 6.07 (1H, d, J=10 Hz, C(O)NHC$\underline{H}$Ar); 4.11 (2H, br s, $CH_2N\underline{H}_2$); 3.74 (2H, s, C$\underline{H}_2NH_2$); 2.83 (2H, t, J=6 Hz, indane C(1)$H_2$ or C(3)$H_2$); 2.80 (2H, t, J=6 Hz, indane C(1)$H_2$ or C(3)$H_2$); 2.00 (2H, quintet, J=6 Hz, indane C(2)$H_2$).

HPLC (Luna 2, Gradient 1): rt=4.46 min.

LC/MS (Luna 2, Gradient 4): rt=2.02 min, 434 $(MH)^+$.

Example 133

3-(Aminomethyl)benzoyl-D/L-4-ethylphenylglycine indan-5-amide hydrochloride salt From 4-ethylbenzaldehyde.

$^1$H NMR ($d_6$ DMSO): 10.30 ppm (1H, s, C(O)N$\underline{H}$-Indane); 8.88 (1H, d, J=9 Hz, C(O)N$\underline{H}$CHAr); 8.23 (3H, br s, $NH_2$ and Ar); 8.06 (1H, s, Ar); 7.99 (1H, d, J=9 Hz, Ar); 7.65 (1H, d, J=10 Hz, Ar); 7.55 (1H, s, Ar); 7.52 (2H, d, J=10 Hz, EtPh C(2)H's or C(3)H's); 7.34 (1H, d, J=10 Hz, indane C(6)H or C(7)H); 7.27 (2H, d, J=10 Hz, EtPh C(2)H's or C(3)H's); 7.15 (1H, d, J=10 Hz, indane C(6)H or C(7)H); 5.85 (1H, d, J=8 Hz, C(O)NHC$\underline{H}$Ar); 4.14 (2H, s, C$\underline{H}_2NH_2$); 2.85 (2H, t, J=6 Hz, indane C(1)$H_2$ or C(3)$H_2$); 2.82 (2H, t, J=6 Hz, indane C(1)$H_2$ or C(3)$H_2$); 2.63 (2H, q, J=9 Hz, C$\underline{H}_2CH_3$); 2.01 (2H, quintet, indane C(2)$H_2$); 1.18 (3H, t, J=9 Hz, $CH_2C\underline{H}_3$).

HPLC (Luna 2, Gradient 1): rt=4.77 min.

LC/MS (Luna 2, Gradient 4): rt=2.23 min, 428 $(MH)^+$.

Example 134

3-(Aminomethyl)benzoyl-D/L-4-isopropylphenylglycine indan-5-amide hydrochloride salt From 4-isopropylbenzaldehyde.

$^1$H NMR ($CD_3CN$): 8.53 ppm (1H, br s, NH); 7.78 (1H, s, Ar); 7.65 (2H, d, J=8 Hz, Ar); 7.48–7.30 (4H, m, Ar); 7.23 (2H, d, J=10 Hz, $^i$PrPh C(2)H's or C(3)H's); 7.18 (1H, d, J=9 Hz, indane C(6)H or C(7)H); 7.08 (1H, d, J=9 Hz, indane C(6)H or C(7)H); 5.58 (1H, d, J=7 Hz, C$\underline{H}$Ar); 3.78 (2H, s, C$\underline{H}_2NH_2$); 2.85 (1H, septet, J=9 Hz, C$\underline{H}(CH_3)_2$); 2.79 (2H, t, J=6 Hz, indane C(1)$H_2$ or C(3)$H_2$); 2.77 (2H, t, J=6 Hz, indane C(1)$H_2$ or C(3)$H_2$); 1.96 (2H, quintet, J=6 Hz, indane C(2)$H_2$); 1.17 (6H, d, J=9 Hz, $CH(C\underline{H}_3)_2$).

HPLC (Luna 2, Gradient 1): rt=4.96 min.

LC/MS (Luna 2, Gradient 4): rt=2.45 min, 442 $(MH)^+$.

Example 135

3-(Aminomethyl)benzoyl-D/L-3-hydroxyphenylglycine indan-5-amide hydrochloride salt From 3-hydroxybenzaldehyde.

$^1$H NMR ($CD_3CN$): 8.51 ppm (1H, br s, NH); 7.76 (1H, s, Ar); 7.70–7.58 (2H, m, Ar); 7.46 (1H, d, J=9 Hz, Ar); 7.40–7.32 (2H, m, Ar and OH); 7.20–7.15 (2H, m, Ar); 7.08 (1H, d, J=8 Hz, Ar); 7.00–6.92 (2H, m, Ar); 6.73 (1H, d, J=9 Hz, Ar); 5.56 (1H, d, J=8 Hz, C$\underline{H}$Ar); 3.78 (2H, s, C$\underline{H}_2NH_2$); 2.80 (2H, t, J=7 Hz, indane C(1)$H_2$ or C(3)$H_2$); 2.77 (2H, t, J=6 Hz, indane C(1)$H_2$ or C(3)$H_2$); 1.98 (2H, quintet, J=6 Hz, indane C(2)$H_2$).

HPLC (Luna 2, Gradient 1): rt=4.01 min.

LC/MS (Luna 2, Gradient 4): rt=1.91 min, 416 $(MH)^+$.

Example 136

3-(Aminomethyl)benzoyl-D/L-4-isopropoxyphenylglycine indan-5-amide hydrochloride salt From 4-isopropoxybenzaldehyde.

$^1$H NMR ($CD_3CN$): 8.44 ppm (1H, br s, NH); 7.86 (1H, s, Ar); 7.64 (1H, d, J=10 Hz, Ar); 7.56 (1H, d, J=8 Hz, Ar); 7.50–7.30 (4H, m, Ar); 7.18 (1H, d, J=10 Hz, indane C(6)H or C(7)H); 7.09 (1H, d, J=10 Hz, indane C(6)H or C(7)H); 6.86 (2H, d, J=10 Hz, $^i$PrOPh C(2)H's or C(3)H's); 5.53 (1H, d, J=8 Hz, C$\underline{H}$Ar); 4.54 (1H, septet, J=6 Hz, OC$\underline{H}(CH_3)_2$); 3.77 (2H, s, C$\underline{H}_2NH_2$); 2.81 (2H, t, J=7 Hz, indane C(1)$H_2$ or C(3)$H_2$); 2.78 (2H, t, J=6 Hz, indane C(1)$H_2$ or C(3)$H_2$); 1.96 (2H, quintet, J=7 Hz, indane C(2)$H_2$); 1.20 (6H, d, J=9 Hz, $OCH(C\underline{H}_3)_2$).

HPLC (Luna 2, Gradient 1): rt=4.83 min.

LC/MS (Luna 2, Gradient 4): rt=2.29 min, 458 $(MH)^+$.

Example 137

3-(Aminomethyl)benzoyl-D/L-4-phenoxyphenylglycine indan-5-amide hydrochloride salt From 4-phenoxybenzaldehyde.

$^1$H NMR (Free base, $CDCl_3$): 8.51 ppm (1H, br s, NH); 7.84 (1H, s, Ar); 7.77 (1H, d, J=6 Hz, N$\underline{H}$CHAr); 7.60–7.49 (2H, m, Ar); 7.48–7.38 (1H, m, Ar); 7.37–7.25 (4H, m, Ar); 7.22–7.09 (3H, m, Ar); 7.05–6.92 (4H, m, Ar); 6.10 (1H, d, J=8 Hz, C$\underline{H}$Ar); 3.95 (2H, s, C$\underline{H}_2NH_2$); 2.85 (4H, t, J=7 Hz, indane C(1)$H_2$ and C(3)$H_2$); 2.07 (2H, quintet, J=7 Hz, indane C(2)$H_2$); 1.52 (2H, br s, $NH_2$).

HPLC (Luna 2, Gradient 1): rt=5.19 min.
LC/MS (Luna 2, Gradient 4): rt=2.48 min, 492 (MH)$^+$.

Example 138

3-(Aminomethyl)benzoyl-D/L-2,4-dimethylphenylglycine indan-5-amide hydrochloride salt From 2,4-dimethylbenzaldehyde.
$^1$H NMR (Free base, CDCl$_3$): 7.72 ppm (1H, s, Ar); 7.64 (1H, d, J=10 Hz, Ar); 7.45–7.25 (5H, m, Ar and NH); 7.09–7.02 (2H, m, Ar); 6.99 (2H, br s, Ar); 5.81 (1H, d, J=7 Hz, C$\underline{H}$Ar); 3.83 (2H, s, C$\underline{H}_2$NH$_2$); 2.83–2.71 (4H, m, indane C(1)H$_2$ and C(3)H$_2$); 2.44 (3H, s, CH$_3$Ar); 2.25 (3H, s, CH$_3$Ar); 2.00 (2H, quintet, J=7 Hz, indane C(2)H$_2$); 1.40 (2H, br s, NH$_2$).
HPLC (Luna 2, Gradient 1): rt=4.50 min.
LC/MS (Luna 2, Gradient 4): rt=2.10 min, 428 (MH)$^+$.

Example 139

3-(Aminomethyl)benzoyl-D/L-2,5-dimethylphenylglycine indan-5-amide hydrochloride salt From 2,5-dimethylbenzaldehyde.
$^1$H NMR (Free base, CDCl$_3$): 7.57 ppm (1H, s, Ar); 7.50 (1H, d, J=9 Hz, Ar); 7.30–7.13 (4H, m, Ar); 7.05 (1H, s, NH); 6.95–6.78 (4H, m, Ar); 5.68 (1H, d, J=8 Hz, C$\underline{H}$Ar); 3.68 (2H, s, C$\underline{H}_2$NH$_2$); 2.70–2.55 (4H, m, indane C(1)H$_2$ and C(3)H$_2$); 2.27 (3H, s, CH$_3$Ar); 2.09 (3H, s, CH$_3$Ar); 1.84 (2H, quintet, J=7 Hz, indane C(2)H$_2$); 1.27 (2H, br s, NH$_2$).
HPLC (Luna 2, Gradient 1): rt=4.10 min.
LC/MS (Luna 2, Gradient 4): rt=1.99 min, 428 (MH)$^+$.

Example 140

3-(Aminomethyl)benzoyl-D/L-6-methylpyridin-2-ylglycine indan-5-amide bis(hydrochloride) salt From 6-methylpyridine-2-carboxaldehyde.
$^1$H NMR (Free base, CDCl$_3$): 9.70 ppm (1H, br s, N$\underline{H}$-Indane); 8.27 (1H, d, J=7 Hz, N$\underline{H}$CHAr); 7.97 (1H, s, Ar); 7.89 (1H, d, J=9 Hz, Ar); 7.67–7.48 (4H, m, Ar); 7.27–7.10 (4H, m, Ar); 5.85 (1H, d, J=7 Hz, C$\underline{H}$Py); 4.00 (2H, s, C$\underline{H}_2$NH$_2$); 2.90 (2H, t, J=7 Hz, indane C(1)H$_2$ or C(3)H$_2$); 2.88 (2H, t, J=7 Hz, indane C(1)H$_2$ or C(3)H$_2$); 2.66 (3H, s, CH$_3$Py); 2.09 (2H, quintet, J=7 Hz, indane C(2)H$_2$); 1.64 (2H, br s, NH$_2$).
HPLC (Luna 2, Gradient 1): rt=3.28 min.
LC/MS (Luna 2, Gradient 4): rt=2.05 min, 415 (MH)$^+$.

Example 141

3-(Aminomethyl)benzoyl-D/L-imidazol-4-ylglycine indan-5-amide bis(hydrochloride) salt From imidazole-4-carboxaldehyde.
$^1$H NMR (Free base, CDCl$_3$): 9.90 ppm (1H, br s, N$\underline{H}$-Indane); 8.39 (1H, br s, NH); 7.83 (1H, s, Ar); 7.72 (1H, d, J=9 Hz, Ar); 7.40 (2H, d, J=10 Hz, Ar); 7.36–7.25 (2H, m, Ar); 7.24 (1H, d, J=8 Hz, indane C(6)H or C(7)H); 7.04 (1H, d, J=8 Hz, indane C(6)H or C(7)H); 6.93 (1H, s, Ar); 6.02 (1H, br d, J=5 Hz, C$\underline{H}$-Im); 3.78 (2H, s, C$\underline{H}_2$NH$_2$); 2.80 (2H, t, J=7 Hz, indane C(1)H$_2$ or C(3)H$_2$); 2.78 (2H, t, J=7 Hz, indane C(1)H$_2$ or C(3)H$_2$); 2.00 (2H, quintet, J=7 Hz, indane C(2)H$_2$).

HPLC (Luna 2, Gradient 1): rt=3.65 min.
LC/MS (Luna 2, Gradient 4): rt=1.45 min, 390 (MH)$^+$.

Example 142

3-(Aminomethyl)benzoyl-D/L-naphth-2-ylglycine indan-5-amide hydrochloride salt

From naphthalene-2-carboxaldehyde.
$^1$H NMR (Free base, CDCl$_3$): 8.52 ppm (1H, br s, NH); 7.97 (1H, s, Ar); 7.80 (1H, d, J=8 Hz, Ar); 7.75 (1H, s, Ar); 7.69 (2H, d, J=10 Hz, Ar); 7.66–7.55 (2H, m, Ar); 7.45 (1H, d, J=8 Hz, Ar); 7.41–7.29 (3H, m, Ar); 7.26 (1H, s, Ar); 7.05 (1H, d, J=8 Hz, indane C(6)H or C(7)H); 6.95 (1H, d, J=8 Hz, indane C(6)H or C(7)H); 6.93 (1H, s, Ar); 6.19 (1H, d, J=9 Hz, C$\underline{H}$-Np); 4.35 (2H, s, C$\underline{H}_2$NH$_2$); 2.72 (2H, t, J=7 Hz, indane C(1)H$_2$ or C(3)H$_2$); 2.69 (2H, t, J=7 Hz, indane C(1)H$_2$ or C(3)H$_2$); 1.92 (2H, quintet, J=7 Hz, indane C(2)H$_2$); 1.55 (2H, br s, NH$_2$).
HPLC (Luna 2, Gradient 4): rt=2.80 min.
LC/MS (Luna 2, Gradient 4): rt=2.29 min, 450 (MH)$^+$.

Example 143

3-(Aminomethyl)benzoyl-D/L-1,3-benzodioxazol-5-ylglycine indan-5-amide hydrochloride salt From piperonal.
$^1$H NMR (Free base, CDCl$_3$): 9.32 ppm (1H, br s, NH); 7.97 (1H, d, J=9 Hz, Ar); 7.79 (1H, s, Ar); 7.75 (1H, d, J=10 Hz, Ar); 7.47 (1H, d, J=8 Hz, Ar); 7.41–7.30 (2H, m, Ar); 7.08–6.98 (2H, m, Ar); 6.68 (1H, d, J=10 Hz, Ar); 6.16 (1H, d, J=8 Hz, C$\underline{H}$-Np); 5.85 (2H, d, J=11 Hz, OCH$_2$O); 3.84 (2H, s, C$\underline{H}_2$NH$_2$); 2.80 (2H, t, J=7 Hz, indane C(1)H$_2$ or C(3)H$_2$); 2.76 (2H, t, J=7 Hz, indane C(1)H$_2$ or C(3)H$_2$); 2.00 (2H, quintet, J=7 Hz, indane C(2)H$_2$); 1.85 (2H, br s, NH$_2$).
HPLC (Luna 2, Gradient 4): rt=2.59 min.
LC/MS (Luna 2, Gradient 4): rt=2.13 min, 444 (MH)$^+$.

Example 144

3-(Aminomethyl)benzoyl-D/L-5-methylfuran-2-ylglycine indan-5-amide hydrochloride salt From 5-methylfuran-2-carboxaldehyde.
$^1$H NMR (Free base, CDCl$_3$): 9.02 ppm (1H, br s, NH); 7.78 (2H, br s, NH and Ar); 7.65 (1H, d, J=9 Hz, Ar); 7.39 (1H, s, Ar); 7.37 (1H, d, J=8 Hz, Ar); 7.28 (1H, t, J=7 Hz, 3-aminomethylphenyl C(5)H); 7.19 (1H, d, J=10 Hz, Ar); 7.00 (1H, d, J=9 Hz, indane C(6)H or C(7)H); 6.29 (1H, d, J=3 Hz, furyl C(3)H or C(4)H); 6.15 (1H, d, J=8 Hz, C$\underline{H}$-Fur); 5.79 (1H, d, J=3 Hz, furyl C(3)H or C(4)H); 3.82 (2H, s, CH$_2$NH$_2$); 2.75 (2H, t, J=7 Hz, indane C(1)H$_2$ or C(3)H$_2$); 2.72 (2H, t, J=7 Hz, indane C(1)H$_2$ or C(3)H$_2$); 2.40 (2H, br s, NH$_2$); 2.10 (3H, s, CH$_3$-Fur); 1.93 (2H, quintet, J=7 Hz, indane C(2)H$_2$).
HPLC (Luna 2, Gradient 1): rt=4.09 min.
LC/MS (Luna 2, Gradient 4): rt=2.05 min, 404 (MH)$^+$.

Example 145

3-(Aminomethyl)benzoyl-D/L-benzofuran-2-ylglycine indan-5-amide hydrochloride salt From benzofuran-2-carboxaldehyde.

$^1$H NMR (Free base, CDCl$_3$): 9.27 ppm (1H, br s, NH); 7.96 (1H, d, J=8 Hz, NHCHAr); 7.72 (1H, s, Ar); 7.66 (1H, d, J=9 Hz, Ar); 7.40–7.23 (5H, m, Ar); 7.18–7.04 (2H, m, Ar); 6.97 (1H, d, J=8 Hz, Ar); 6.92 (1H, d, J=9 Hz, indane C(6)H or C(7)H); 6.76 (1H, s, benzofuran C(3)H); 6.45 (1H, d, J=8 Hz, CHAr); 3.76 (2H, s, CH$_2$NH$_2$); 2.77–2.60 (4H, m, indane C(1)H$_2$ and C(3)H$_2$); 2.10 (3H, s, CH$_3$-Fur); 2.01–1.89 (2H, m, indane C(2)H$_2$); 1.64 (2H, br s, NH$_2$).

HPLC (Luna 2, Gradient 1): rt=4.13 min.
LC/MS (Luna 2, Gradient 4): rt=2.15 min, 440 (MH)$^+$.

Example 146

3-(Aminomethyl)benzoyl-D/L-3-methylbenzo (b) thiophen-2-ylglycine indan-5-amide hydrochloride salt From 3-methylbenzo(b)thiophene-2-carboxaldehyde.

$^1$H NMR (Free base, CDCl$_3$): 8.39 ppm (1H, br s, NH); 7.74–7.62 (4H, m, NH and Ar); 7.58 (1H, d, J=8 Hz, Ar); 7.38 (1 H, d, J=9 Hz, Ar); 7.35–7.23 (4H, m, Ar); 7.09 (1H, d, J=10 Hz, indane C(6)H or C(7)H); 6.99 (1H, d, J=10 Hz, indane C(6)H or C(7)H); 6.40 (1H, d, J=8 Hz, CHAr); 3.79 (2H, s, CH$_2$NH$_2$); 2.75 (2H, t, J=6 Hz, indane C(1)H$_2$ or C(3)H$_2$); 2.73 (2H, t, J=6 Hz, indane C(1)H$_2$ or C(3)H$_2$); 2.50 (3H, s, CH$_3$Ar); 2.00–1.88 (2H, m, indane C(2)H$_2$); 1.55 (2H, br s, NH$_2$).

HPLC (Luna 2, Gradient 1): rt=4.33 min.
LC/MS (Luna 2, Gradient 4): rt=2.34 min, 470 (MH)$^+$.

Example 147

3-(Aminomethyl)benzoyl-D/L-(4-hydroxycarbonyl)-phenylglycine indan-5-amide trifluoroacetate salt

3-(BOC-aminomethyl)benzoyl-D/L-N-(2,4-dimethoxybenzyl)-4-(methoxycarbonyl)phenylglycine indan-5-amide 4-Methoxycarbonylbenzaldehyde was reacted in the same way as p-tolualdehyde in Example 131, to afford 3-(N-BOC-aminomethyl)benzoyl-D/L-N-(2,4-dimethoxybenzyl)-4-(methoxycarbonyl)phenylglycine indan-5-amide.

3-(BOC-aminomethyl)benzoyl-D/L-N-(2,4-dimethoxybenzyl)-4-(hydroxycarbonyl)phenylglycine indan-5-amide To a stirred solution of the methyl ester (0.55 g, 0.77 mmol) in 1:1 THF/water (30 mL) was added lithium hydroxide monohydrate (65 mg, 1.5 mmol). The solution was warmed to 70° C. for 2 hours, then cooled to room temperature overnight. The reaction mixture was acidified with 5% aqueous HCl and extracted with ethyl acetate (2×100 mL). The dried extracts were evaporated to give an oily foam.

Trifluoroacetic acid (4 mL) was added to a stirred solution of the foam (40 mg) in dichloromethane (20 mL) and allowed to stand overnight, resulting in the solution turning deep pink. The solution was evaporated to give a reddish oil which was triturated with ether to give a grey solid, which was purified by preparative HPLC to give a white solid (34 mg, 8%).

3-(Aminomethyl)benzoyl-D/L-4-(hydroxycarbonyl) phenyl-glycine indan-5-amide trifluoroacetate salt $^1$H NMR (d$_4$ MeOH): 8.13 ppm (2H, d, J=9 Hz, Ar); 8.03 (2H, s, Ar); 7.81–7.62 (4H, m, Ar); 7.34 (1H, dd, J=9, 5 Hz, Ar); 7.20 (1H, d, J=8 Hz, Ar); 5.97 (1H, s, CHPh); 4.25 (1H, s, CH$_2$NH$_2$); 2.92 (4H, m, indane C(1)H$_2$ and C(3)H$_2$); 2.12 (quintet, J=7 Hz, indane C(2)H$_2$).

HPLC (Luna 2, Gradient 1): rt=3.64 minutes.
LC/MS (Luna 2, Gradient 4): rt=1.83 minutes, 445 (MH)$^+$.

Example 148

3-(Aminomethyl)benzoyl-D/L-(4-hydroxymethyl) phenylglycine indan-5-amide trifluoroacetate salt To a stirred solution of 3-(BOC-aminomethyl)benzoyl-D/L-N-2,4-dimethoxybenzyl-(4-hydroxycarbonyl)phenylglycine indan-5-amide (0.49 g, 0.71 mmol) in THF (15 mL) at 0° C. was added 1.0M borane/THF complex (5 mL, 5 mmol) dropwise, then left for 2 hrs. To the resulting solution was added 1:1 acetic acid/water (10 mL), left overnight, then evaporated under reduced pressure. The resulting slushy solid was partitioned between water (30 mL) and ethyl acetate (50 mL). The organic layer was dried over MgSO$_4$ and evaporated to give an off-white foam. The foam was dissolved in dichloromethane (20 mL) and treated with trifluoroacetic acid (4 mL) for 4 hours, then evaporated to give an oil. The oil was purified by preparative HPLC to give a white solid (100 mg, 30%).

$^1$H NMR (d$_4$ MeOH): 7.90 (2H, m, Ar); 7.62–7.49 (4H, m, Ar); 7.35 (3H, m, Ar); 7.18 (1H, d, J=8 Hz, Ar); 7.08 (1H, d, J=8 Hz, Ar); 5.78 (1H, s, CHPh); 4.57 (2H, s, CH$_2$OH); 4.13 (1H, s, CH$_2$NH$_2$); 2.83 (1H, m, J=7 Hz, 2× indane CH$_2$); 2.02 (2H, quintet, J=7 Hz, indane CH$_2$).

HPLC (Luna 2, Gradient 1): rt=3.78 minutes.
HPLC (Symmetry, Gradient 2): rt=5.89 minutes.
LC/MS (Luna 2, Gradient 4): rt=1.88 minutes, 430 (MH)$^+$.

Example 149

3-(Aminomethyl)benzoyl-D/L-2-phenylthiazol-4-ylglycine indan-5-amide trifluoroacetate salt Prepared in a similar manner to Example 61 except that α-N-BOC-D/L-2-phenylthiazol-4-ylglycine, synthesised as described below, was used in place of D/L-4-(N-BOC-aminomethyl)-α-(N-benzyloxycarbonyl)phenylglycine.

Ethyl oximinoacetoacetate

This was prepared from ethyl acetoacetate (10.00 g) using the method of Fischer (*Organic Synthesis Coll.* Vol. 3, 513–516) to yield the titled compound (12.45 g).

$^1$H NMR (CDCl$_3$) 1.25 (3H, t), 2.35 (3H, s), 4.3 (2H, q), 8.8 (1H, br.).

Ethyl-γ-chloro-α-oximinoacetoacetate

This was prepared from ethyl oximinoacetoacetate (1.73 g) using the method of Hatanaka et al. (*Journal of Medicinal Chemistry*, 1973, 16(9), 978–984) to yield the titled compound (1.44 g).

$^1$H NMR (CDCl$_3$) 1.25 (3H, t), 4.3 (2H, q), 4.55 (2H, s), 9.45 (1H, s), contains 20% starting material by NMR.

N-BOC-D/L-2-phenylthiazol-4-ylglycine

A solution of ethyl γ-chloro-α-oximinoacetoacetate (2.10 g, 10.8 mmol) and thiobenzamide (1.49 g, 10.8 mmol) in dry benzene (15 mL) was heated to reflux. After 4 hours, the reaction mixture was poured onto NaHCO$_3$ (sat., aq., 50 mL); The resulting mixture was extracted with ethyl acetate (2×50 mL); and the combined extracts dried over MgSO$_4$ and evaporated under reduced pressure. Flash chromatography (ethyl acetate:hexane 1:4, R$_f$ 0.30) then afforded impure ethyl α-oximino-2-phenylthiazole-4-acetate (3.22 g). The crude oxime was then dissolved in methanol (15 mL) and formic acid (50% aq., 15 mL) was added. The mixture was cooled to 0° C. and zinc dust (2.00 g, 30.6 mmol) was added portionwise over 30 minutes. The reaction mixture was allowed to warm to room temperature, and stirred for 6 hours. The solution was then filtered, basified to pH 9 with solid NaHCO$_3$, and extracted with ethyl acetate (3×80 mL). The combined extracts were then dried and evaporated to afford D/L-2-phenylthiazol-4-ylglycine ethyl ester (1.43 g, 5.45 mmol, 50% from the chloro-oxime). The ester (194 mg, 0.74 mmol) was then dissolved in tetrahydrofuran (5 mL). Triethylamine (120 μL, 87 mg, 0.86 mmol) was added, followed by di-t-butyl dicarbonate (180 mg, 0.82 mmol). After stirring at room temperature for 4 days, water (20 mL) was added and the solution extracted with dichloromethane (2×20 mL). The combined extracts were evaporated and purified by flash column chromatography (ethyl acetate:hexane 1:4, R$_f$ 0.45) to afford N-t-butyloxycarbonyl-D/L-2-phenylthiazol-4-ylglycine ethyl ester (158 mg, 0.44 mmol, 59%) as a clear oil. The oil was dissolved in tetrahydrofuran (2 mL) and LiOH.H$_2$O (80 mg as a solution in 2 mL water) was added. After stirring at room temperature for 2 hours, water (10 mL) was added, and the solution extracted with ethyl acetate (5 mL). The aqueous layer was then acidified to pH 4 with 2N HCl, and extracted with ethyl acetate (2×20 mL); The latter extracts were combined and evaporated to afford N-BOC-D/L-2-phenylthiazol-4-ylglycine (116 mg, 0.35 mmol, 75%) as a white powder.

$^1$H NMR (CDCl$_3$): 10.81 (1H, br s, CO$_2$H); 7.80–7.71 & 7.30–7.22 (2H & 3H, m, Ph); 7.21 (1H, s, thiazole CH); 5.99 (1H, br d, J=6 Hz, NHBoc); 5.39 (1H, br d, J=6 Hz, α-CH); 1.31 (9H, s, C(CH$_3$)$_3$).

3-(Aminomethyl)benzoyl-D/L-2-phenylthiazol-4-ylglycine indan-5-amide trifluoroacetate salt $^1$H NMR (d$_3$ acetonitrile): 9.00 (1H, s, NHAr); 8.15 (1H, d, J=6 Hz, NHCH); 8.02 (1H, s, Ar); 7.99–7.88 (2H, m, Ar); 7.59–7.40 (7H, m, Ar); 7.25 & 7.11 (2×1H, 2×d, 2×J 7 Hz, indanyl CHCH); 6.01 (1H, d, J=6 Hz); 4.15 (2H, br s, CH$_2$NH$_2$); 2.90–2.79 (4H, m, CH$_2$CH$_2$CH$_2$); 2.00 (2H, pentet, J=6 Hz, CH$_2$CH$_2$CH$_2$).

HPLC (Luna 2, Gradient 1): rt=4.22 minutes.

LC/MS (Luna 2, Gradient 4): rt=2.29 minutes, 483 (MH)$^+$.

Example 150

3-(Aminomethyl)benzoyl-D/L-(2-methylthiazol-4-yl)glycine indan-5-amide trifluoroacetate salt Synthesised from N-BOC-D/L-2-methylthiazol-4-ylglycine, which was prepared in an analogous manner to N-BOC-D/L-2-phenylthiazol-4-ylglycine above, except that thioacetamide was used in place of thiobenzamide.

$^1$H NMR (d$_4$ MeOH): 8.00 ppm (2H, m, Ar); 7.8–7.57 (2H, m, Ar); 7.48 (2H, d, J=8 Hz, Ar); 7.30 (1H, d, J=9 Hz, Ar); 7.16 (1H, d, J=8 Hz, Ar); 6.01 (1H, s, CHPh); 4.21 (2H, s, CH$_2$NH$_2$); 2.90 (2H, t, J=8 Hz, indane C(1)H$_2$ or C(3)H$_2$); 2.88 (2H, t, J=8 Hz, indane C(1)H$_2$ or C(3)H$_2$); 2.74 (3H, s, Me); 2.10 (2H, quintet, J=8 Hz, indane C(2)H$_2$).

HPLC (Luna, Gradient 3): rt=5.92 (92%)

LC/MS (Luna 2, Gradient 4): rt=1.88 minutes, 421 (MH)$^+$.

Example 151

3-(Aminomethyl)benzoyl-D/L-(4-aminocarbonyl) phenylglycine indan-5-amide trifluoroacetate salt

3-(N-BOC-Aminomethyl)benzoyl-D/L-(4-methoxycarbonyl)phenylglycine indan-5-amide Prepared in a manner analogous to the preparation of 3-(N-BOC-aminomethyl)benzoyl-D/L-4-(N-BOC-aminomethyl)phenylglycine indan-5-amide, an intermediate in the preparation of Example 61, except that α-N-BOC-D/L-(4-methoxycarbonyl)phenylglycine was used instead of α-N-Z-D/L-(4-BOC-aminomethyl)phenylglycine; appropriate deprotection methods were used where required.

3-(N-BOC-Aminomethyl)benzoyl-D/L-(4-hydroxycarbonyl)phenylglycine indan-5-amide A solution of the methyl ester (500 mg, 0.90 mmol) in tetrahydrofuran (15 mL) was treated with a solution of LiOH in water (1 mL of 1M, 1.0 mmol) and the mixture heated at reflux for three hours. After cooling to room temperature, the solution was diluted with water (50 mL), made acidic with 1N HCl and extracted with ethyl acetate (3×15 mL). The solvents were dried over MgSO$_4$ and evaporated under reduced pressure to afford the acid as an off-white solid (390 mg, 80%) which was used without further purification.

3-(N-BOC-Aminomethyl)benzoyl-D/L-(4-aminocarbonyl)phenylglycine indan-5-amide A solution of 3-(N-BOC-aminomethyl)benzoyl-D/L-(4-hydroxycarbonyl)phenylglycine indan-5-amide (370 mg, 0.7 mmol) in chloroform (10 mL) was treated with EEDQ (210 mg, 0.85 mmol) and NH$_4$HCO$_3$ (150 mg, 1.9 mmol) and stirred overnight at room temperature. The organic phase was washed with water (3×10 mL), dried (MgSO$_4$) and concentrated under reduced pressure. The residue was purified by flash chromatography using ethyl acetate/chloroform 1/1 as eluant to afford the carboxamide as a colourless solid (52 mg, 14%).

$^1$H NMR (CDCl$_3$): 9.30 ppm (1H, s, NH); 8.85 (2H, s, NH$_2$); 8.10–7.98 (2H, m, Ar); 7.81–7.25 (8H, m, Ar and NH); 7.10 (1H, d, J=7.2 Hz, Ar); 6.98 (1H, d, J=7.2 Hz, Ar); 6.14 (1H, s, CHPh); 5.00 (1H, br s, NH); 4.22 (2H, s, CH$_2$NH$_2$); 2.79–2.63 (4H, m, 2×CH$_2$ indane); 2.00–1.88 (2H, m, CH$_2$ indane); 1.37 (9H, s, C$_4$H$_9$).

3-(Aminomethyl)benzoyl-D/L-(4-aminocarbonyl) phenylglycine indan-5-amide trifluoroacetate salt A solution of 3-(N-BOC-aminomethyl)benzoyl-D/L-(4-aminocarbonyl)phenylglycine indan-5-amide (26 mg, 0.05 mmol) in dichloromethane (3 mL) was stirred at room temperature and trifluoroacetic acid (2 mL) was added. Stirring was continued for a further hour and the solvents were removed under reduced pressure. The TFA salt was purified by flash chromatography using methanol/chloroform 1/4as eluant to afford a colourless solid (20 mg, 91%).

$^1$H NMR ($d_4$ methanol): 7.86–7.72 ppm (3H, m, Ar); 7.67 (1H, d, J=7.2 Hz, Ar); 7.57 (2H, d, J=7.2 Hz, Ar); 7.40 (1H, d, J=7.2 Hz, Ar); 7.34–7.27 (2H, m, Ar); 7.13 (1H, d, J=7.2 Hz, Ar); 7.00 (1H, d, J=7.2 Hz, Ar); 5.79 (1H, s, CHPh); 3.77 (2H, s, C$\underline{H}_2$NH$_2$); 2.83–2.67 (4H, m, 2×CH$_2$ indane); 2.03–1.91 (2H, m, CH$_2$ indane).

HPLC (Luna 2, Gradient 1): rt=1.75 minutes.
LC/MS (Luna 2, Gradient 4): rt=1.83 minutes, 443 (MH)$^+$.

Example 152

3-(Aminomethyl)benzoyl-D/L-4-(aminomethyl)phenylglycine 1-(aminopropionyl)-2,3-dihydroindol-6-amide tris(hydrochloride) salt Prepared in a manner analogous to that of Example 61, except that 1-(3-N-BOC-aminopropyl)-6-amino-2,3-dihydroindole, synthesised as described below, was used in place of 5-aminoindane.

1-(3-N-BOC-Aminopropyl)-6-nitro-2,3-dihydroindole

To a solution of N-BOC-β-alanine (1.15 g, 6.1 mmol) and 6-nitro-2,3-dihydroindole (1.0 g, 6.1 mmol) in DMF (20 mL) was added 1-(3-dimethylaminopropyl)-3-ethylcarbodiimide hydrochloride (1.28 g, 6.7 mmol) and diisopropylethylamine (1.17 mL, 6.7 mmol). The resulting solution was stirred overnight at room temperature. After this time the mixture was partitioned between saturated aqueous citric acid (50 mL) and ethyl acetate (100 mL). The organic layer was separated and washed successively with saturated aqueous sodium bicarbonate solution (50 mL) and water (3×50 mL), dried over MgSO$_4$, and then concentrated under reduced pressure to give the product as a pale foam (1.49 g, 76%).

$^1$H NMR (CDCl$_3$): 8.98 ppm (1H, d, J=1 Hz, C(7)H); 7.82 (1H, dd, J=10, 1 Hz, C(5)H); 7.21 (1H, d, J=10 Hz, C(4)H); 5.33 (1H, br s, NH); 4.07 (2H, t, J=8 Hz, C(2)H$_2$); 3.48 (2H, m, CH$_2$C$\underline{H}_2$NHBoc); 3.22 (2H, t, J=8 Hz, C(3)H$_2$); 2.60 (2H, t, J=5 Hz, C$\underline{H}_2$CH$_2$NHBoc; 1.38 (9H, s, $^t$Bu).

1-(3-N-BOC-aminopropyl)-6-amino-2,3-dihydroindole

To a solution of 1-(3-BOC-aminopropyl)-6-nitro-2,3-dihydroindole (1.49 g, 4.7 mmol) in methanol (40 mL) was added 10% palladium on carbon (catalytic ammount) and the resulting suspension stirred vigorously under an atmosphere of hydrogen. After 3 hours the mixture was purged with nitrogen and filtered through celite to remove the catalyst. The filtrate was concentrated under reduced pressure to give the product as a pale solid (1.35 g, quantitative).

$^1$H NMR (CDCl$_3$): 7.68 ppm (1H, d, J=1 Hz, C(7)H); 6.95 (1H, d, J=10 Hz, C(4)H); 6.39 (1H, dd, J=10, 1 Hz, C(5)H); 5.31 (1H, br s, NH); 4.0 (2H, t, J=8 Hz, C(2)H$_2$, 3.50 (2H, m, CH$_2$C$\underline{H}_2$NHBoc); 3.06 (2H, J=8 Hz, C(5)H$_2$); 2.99 (2H, br s, NH$_2$); 2.61 (2H, t, J=5 Hz, C$\underline{H}_2$CH$_2$NHBoc); 1.42 (9H, s, $^t$Bu).

3-(Aminomethyl)benzoyl-D/L-4-(aminomethyl)phenylglycine 1-(aminopropionyl)-2,3-dihydroindol-6-amide tris(hydrochloride) salt $^1$H NMR (D$_2$O): 7.91 ppm (1H, s, Ar); 7.66 (2H, br s, Ar); 7.50–7.46 (1H, m, Ar); 7.43 (2H, d, J=10 Hz, p-aminomethylphenyl C(2)H's or C(3)H's); 7.37 (1H, d, J=10 Hz, Ar); 7.30 (2H, d, J=10 Hz, p-aminomethylphenyl C(2)H's or C(3)H's); 7.02 (1H, d, J=9 Hz, indoline C(4)H or C(5)H); 6.86 (1H, d, J=9 Hz, indoline C(4)H or C(5)H); 5.54 (1H, s, C$\underline{H}$Ar); 4.01 (2H, s, ArC$\underline{H}_2$NH$_2$); 3.97 (2H, s, ArC$\underline{H}_2$NH$_2$); 3.82 (2H, t, J=9 Hz, CH$_2$C$\underline{H}_2$NH$_2$); 3.10 (2H, t, J=6 Hz, indoline C(2)H$_2$); 2.90 (2H, t, J=9 Hz, C$\underline{H}_2$CH$_2$NH$_2$); 2.66 (2H, t, J=6 Hz, indoline C(3)H$_2$).

HPLC (Luna 2, Gradient 4): rt=1.42 min.
LC/MS (Luna 2, Gradient 4): rt=0.86 min, 501 (MH)$^+$.

Example 153

3-(Aminomethyl)benzoyl-D/L-piperidin-4-ylglycine 4-isopropylanilide

Prepared in a manner analogous to Example 69, except that 4-isopropylaniline was used in place of 5-aminoindane.

$^1$H NMR ($d_4$ methanol): 8.04–7.93 ppm (2H, m, Ar); 7.73–7.50 (4H, m, Ar); 7.20 (2H, d, J=7.5 Hz, Ar); 4.67 (1H, d, J=7.5 Hz, CH); 4.19 (2H, s, C$\underline{H}_2$NH$_2$); 3.56–3.41 (2H, m, CH$_2$ pip); 3.12–2.97 (2H, m, CH$_2$ pip); 2.87 (1H, quintet, CH ipr); 2.44–2.26 (1H, m, Ar); 2.22–1.98 (2H, m, CH$_2$ pip); 1.87–1.58 (2H, m, CH$_2$ pip); 1.28–1.21 (6H, app. d, 2×CH$_3$).

HPLC (Luna 2, Gradient 1): rt=2.18 minutes.
LC/MS (Luna 2, Gradient 4): rt=1.37 minutes, 409 (MH)$^+$.

Example 154

3-(Aminomethyl)benzoyl-D/L-piperidin-4-ylglycine 1-acetyl-2,3-dihydroindol-6-amide bis(trifluoroacetate) salt Prepared in a manner analogous to Example 69 except that 1-acetyl-2,3-dihydroindol-6-amine was used in place of 5-aminoindane.

$^1$H NMR ($d_6$ DMSO): 8.65 ppm (1H, br s, NH); 8.34–8.17 (3H, m, NH); 8.00 (1H, s, Ar); 7.93 (1H, d, J=7.5 Hz, Ar); 7.63 (1H, d, J=7.2 Hz, Ar); 7.55–7.46 (3H, m, Ar); 7.15 (1H, d, J=7.5 Hz, Ar); 4.58 (1H, d, J=7.5 Hz, CH); 4.14–4.01 (4H, m, C$\underline{H}_2$NH$_2$, CH$_2$ indoline); 3.40–3.27 (2H, m, CH$_2$ pip); 3.15–3.02 (2H, m, CH$_2$ indoline); 2.96–2.73 (2H, m, CH$_2$ pip); 2.16 (3H, s, COCH$_3$); 2.02–1.89 (1H, m, CH pip); 1.80–1.68 (1H, m, CH pip); 1.64–1.33 (3H, m, CH, CH$_2$ pip).

HPLC (Luna 2, Gradient 1): rt=2.65 minutes.
LC/MS (Luna 2, Gradient 4): rt=0.54 minutes, 450 (MH)$^+$.

Example 155

3-(Aminomethyl)benzoyl-D/L-piperidin-4-glycine 1-(aminoacetyl)-2,3-dihydroindol-6-amide tris(trifluoroacetate) salt Prepared in a manner analogous to Example 69 except that 1-(N-BOC-aminoacetyl)-2,3-dihydroindol-6-amine was used in place of 5-aminoindane.

$^1$H NMR ($d_4$ methanol): 8.46 ppm (1H, s, Ar); 8.03–7.91 (2H, m, Ar); 7.70 (1H, d, J=7.2 Hz, Ar); 7.65–7.54 (1H, m, Ar); 7.40 (1H, d, J=7.5 Hz, Ar); 7.21 (1H, d, J=7.5 Hz, Ar); 4.65 (1H, d, J=7.5 Hz, CH); 4.21 (2H, s, C$\underline{H}_2$NH$_2$); 4.16–4.07 (2H, m, CH$_2$ indoline); 4.02 (2H, s, C$\underline{H}_2$NH$_2$); 3.55–3.40 (2H, m, CH$_2$ pip); 3.28–3.17 (2H, m, CH$_2$ indoline); 3.10–2.92 (2H, m, CH$_2$ pip); 2.40–2.25 (1H, m, CH pip); 2.23–1.93 (2H, m, CH$_2$ pip); 1.86–1.60 (2H, m, CH$_2$ pip).

HPLC (Luna 2, Gradient 1): rt=2.03 minutes.
LC/MS (Luna 2, Gradient 4): rt=0.64 minutes, 465 (MH)$^+$.

Example 156

3-(Aminomethyl)benzoyl-D/L-1-acetylpiperidin-4-ylglycine indan-5-amide trifluoroacetate salt 3-(N-Z-Aminomethyl)benzoyl-D/L-1-BOC-piperidin-4-ylglycine indan-5-amide This compound was prepared in an analogous fashion to 3-(N-BOC-aminomethyl)benzoyl-D/L-(N-BOC-piperidin-4-yl)glycine indan-5-amide, an intermediate in the synthesis of Example 69, except that 3-(N-Z-aminomethyl)benzoic acid was used in the final coupling reaction.

3-(N-Z-Aminomethyl)benzoyl-D/L-1-acetylpiperidin-4-ylglycine indan-5-amide

A solution of 3-(N-Z-aminomethyl)benzoyl-D/L-1-BOC-piperidin-4-ylglycine indan-5-amide (65 mg, 0.1 mmol) in dichloromethane (3 mL) was stirred at room temperature and trifluoroacetic acid (2 mL) was added. Stirring was continued for an hour and the solvents were removed under reduced pressure. The residue was taken up in dichloromethane (5 mL) and treated with triethylamine (0.055 mL, 0.4 mmol) and acetyl chloride (0.014 mL, 0.2 mmol) and allowed to stir for 1 hour. The solution was washed with water (3×5 mL), dried (MgSO$_4$) and concentrated under reduced pressure. The residue was purified by flash chromatography using methanol/dichloromethane 1/9 as eluent to afford a colourless solid (45 mg, 78%).

$^1$H NMR ($d_4$ methanol): 7.82–7.68 ppm (2H, m, Ar); 7.51–7.20 (9H, m, Ar); 7.16 (1H, d, J=7.2 Hz, Ar); 5.09 (2H, s, OCH$_2$Ph); 4.65–4.47 (2H, m, CH and NH); 4.31 (2H, s, C$\underline{H}_2$NH$_2$); 4.00–3.85 (1H, m, CH pip); 3.14–2.97 (1H, m, CH pip); 2.92–2.77 (4H, m, 2×CH$_2$ indane); 2.66–2.48 (1H, m, CH pip); 2.32–2.17 (1H, m, CH pip); 2.15–1.90 (6H, m, COCH$_3$, CH$_2$ ind, CH pip); 1.85–1.67 (1H, m, CH pip); 1.53–1.20 (2H, m, CH$_2$ pip).

3-(Aminomethyl)benzoyl-D/L-1-acetylpiperidin-4-ylglycine indan-5-amide trifluoroacetate salt 10% Palladium on carbon (20 mg) was added to a solution of 3-(N-Carbobenzyloxy-aminomethyl)benzoyl-D/L-1-acetylpiperidin-4-ylglycine indan-5-amide (45 mg, 0.08 mmol) in methanol (20 mL) and the suspension was stirred under a hydrogen atmosphere overnight. The mixture was filtered and the filter was washed with methanol (20 mL). The combined filtrates were concentrated under reduced pressure and the amine was purified by flash chromatography using methanol/dichloromethane 1/9 as eluant to afford a colourless solid. Trifluoroacetic acid (1 mL) was added and the solution was concentrated under reduced pressure to give the TFA salt (16 mg, 36%).

$^1$H NMR ($d_4$ methanol): 7.98–7.87 ppm (2H, m, Ar); 7.73–7.20 (4H, m, Ar); 7.10 (1H, d, J=7.2 Hz, Ar); 4.55 (1H, s, CH); 4.15 (2H, s, C$\underline{H}_2$NH$_2$); 4.00–3.82 (2H, m, CH$_2$ pip); 3.15–2.95 (1H, m, CH pip); 2.89–2.71 (4H, m, 2×CH$_2$ indane); 2.66–2.48 (1H, m, CH pip); 2.29–2.11 (1H, m, CH pip); 2.10–1.85 (6H, m, COCH$_3$, CH$_2$ ind, CH pip); 1.81–1.62 (1H, m, CH pip); 1.50–1.19 (2H, m, CH$_2$ pip).

HPLC (Luna 2, Gradient 1): rt=3.64 minutes.
LC/MS (Luna 2, Gradient 4): rt=1.75 minutes, 449 (MH)$^+$.

Examples 157–159 were prepared in a manner analogous to Example 156, except that the indicated carboxylic acid derivative was used to form the amide of the piperidine nitrogen, under appropriate conditions.

Example 157

3-(Aminomethyl)benzoyl-D/L-(1-propanoyl)piperidin-4-ylglycine indan-5-amide trifluoroacetate salt From propanoyl chloride.

$^1$H NMR ($d_4$ methanol): 7.80 ppm (2H, s, Ar); 7.59–7.41 (2H, m, Ar); 7.36 (1H, s, Ar); 7.16 (1H, d, J=7.2 Hz, Ar); 7.03 (1H, d, J=7.2 Hz, Ar); 4.53–4.39 (2H, m, CH, CH pip); 4.04 (2H, s, C$\underline{H}_2$NH$_2$); 3.07–2.90 (1H, m, CH pip); 2.86–2.70 (4H, m, 2×CH$_2$ ind); 2.61–2.43 (1H, m, CH pip); 2.36–2.22 (2H, m, COC$\underline{H}_2$CH$_3$); 2.19–2.04 (1H, m, CH pip); 2.01–1.79 (3H, m, CH$_2$ ind, CH pip); 1.76–1.60 (1H, m, CH pip); 1.41–1.10 (2H, m, CH$_2$ pip); 0.93 (3H, t, J=7.5 Hz, COCH$_2$C$\underline{H}_3$).

HPLC (Luna 2, Gradient 1): rt=3.54 minutes.
LC/MS (Luna 2, Gradient 4): rt=1.96 minutes, 463 (MH)$^+$.

Example 158

3-(Aminomethyl)benzoyl-D/L-(1-isobutyryl)piperidin-4-ylglycine indan-5-amide

From isobutyryl chloride.

$^1$H NMR ($d_4$ methanol): 7.75 ppm (1H, s, Ar); 7.67 (1H, d, J=7.2 Hz, Ar); 7.42 (1H, d, J=7.2 Hz, Ar); 7.38–7.29 (2H, m, Ar); 7.18 (1H, d, J=7.5 Hz, Ar); 7.03 (1H, d, J=7.5 Hz, Ar); 4.57–4.41 (1H, m, CH); 4.09–3.95 (1H, m, CH pip); 3.81 (2H, s, C$\underline{H}_2$NH$_2$); 3.10–2.94 (1H, m, CH pip); 2.91–2.67 (5H, m, CH ipr, 2×CH$_2$ ind); 2.62–2.43 (1H, m, CH pip); 2.25–2.07 (1H, m, CH pip); 2.04–1.59 (4H, m, CH$_2$ ind, 2×CH pip); 1.43–1.12 (2H, m, CH$_2$ pip); 0.98 (6H, m, 2×CH$_3$).

HPLC (Luna 2, Gradient 1): rt=3.39 minutes.
LC/MS (Luna 2, Gradient 4): rt=1.88 minutes, 477 (MH)$^+$.

Example 159

3-(Aminomethyl)benzoyl-D/L-(1-aminoacetyl)piperidin-4-ylglycine indan-5-amide bis(trifluoroacetate) salt From N-BOC-glycine.

$^1$H NMR (d$_4$ methanol): 7.94–7.81 ppm (2H, m, Ar); 7.58 (1H, d, J=7.2 Hz, Ar); 7.54–7.44 (1H, m, Ar); 7.38 (11H, s, Ar); 7.20 (1H, d, J=7.5 Hz, Ar); 7.08 (1H, d, J=7.2 Hz, Ar); 4.54–4.40 (1H, m, CH); 4.10 (2H, s, CH$_2$NH$_2$); 3.95–3.76 (2H, m, COCH$_2$NH$_2$); 3.74–3.65 (1H, m, CH pip); 3.12–2.96 (1H, m, CH pip); 2.84–2.58 (5H, m, 2×CH$_2$ ind, CH pip); 2.26–2.07 (1H, m, CH pip); 2.04–1.84 (3H, m, CH$_2$ ind, CH pip); 1.79–1.69 (1H, m, CH pip); 1.53–1.04 (2H, m, CH$_2$ pip).

HPLC (Luna 2, Gradient 1): rt=2.65 minutes.

LC/MS (Luna 2, Gradient 4): rt=1.35 minutes, 464 (MH)$^+$.

Example 160

3-(Aminomethyl)benzoyl-D/L-phenylglycine benzothiazol-2-amide trifluoroacetate salt α-N-BOC-D/L-Phenylglycine benzothiazol-2-amide A solution of N-BOC-D-phenylglycine (750 mg, 3.0 mmol) in anhydrous tetrahydrofuran (20 mL) was stirred at room temperature under argon. Isobutyl chloroformate (0.52 mL, 4.0 mmol) and diisopropylethylamine (0.81 mL, 4.7 mmol) were added and the solution was stirred for 30 minutes. A solution of 2-aminobenzothiazole (500 mg, 3.3 mmol) in tetrahydrofuran (10 mL) was added to the mixed anhydride solution and stirred overnight at room temperature. Ethyl acetate (50 mL) was added and the organic phase was washed with water (25 mL), 5% HCl solution (25 mL), saturated aqueous NaHCO$_3$ (25 mL) and water (25 mL), before being dried (MgSO$_4$) and concentrated under reduced pressure. The residue was purified by flash chromatography using ethyl acetate/hexane 1/1 as eluant to afford the coupled product as a yellow oil (785 mg, 68%).

$^1$H NMR (CDCl$_3$): 7.71 ppm (1H, d, J=7.2 Hz, Ar); 7.42 (1H, d, J=7.2 Hz, Ar); 7.36 (8H, m, Ar and NH); 6.29 (1H, br s, CH); 5.60 (1H, br s, NH); 1.30 (9H, s, C$_4$H$_9$).

3-(N-BOC-Aminomethyl)benzoyl-D/L-phenylglycine benzothiazol-2-amide

A solution of the α-N-BOC-D/L-phenylglycine benzothiazol-2-amide (785 mg, 2.24 mmol) in dichloromethane (5 mL) was treated with trifluoroacetic acid (2 mL) and stirred for 1 hour at room temperature. The solution was concentrated under reduced pressure and the residual TFA salt was taken up in dimethylformamide (15 mL). This solution was treated with triethylamine (0.92 mL, 6.6 mmol), 1-(3-dimethylaminopropyl)-3-ethylcarbodiimide hydrochloride (478 mg, 2.5 mmol), 3-(N-BOC-aminomethyl)benzoic acid (562 mg, 2.24 mmol) and DMAP (50 mg) and stirred overnight at room temperature. The solution was partitioned between ethyl acetate (25 mL) and water (25 mL) and the organic phase was washed with 5% HCl solution (25 mL), saturated aqueous NaHCO$_3$ (25 mL) and water (25 mL) before being dried (MgSO$_4$) and concentrated under reduced pressure to afford a yellow oil. The residue was purified by flash chromatography using ethyl acetate/hexane 1/1 as eluant to afford a colourless solid (185 mg, 16%).

$^1$H NMR (CDCl$_3$): 7.87–7.73 ppm (2H, m, Ar and NH); 7.66–7.45 (3H, m, Ar and NH); 7.40–7.30 (3H, m, Ar); 7.26–7.00 (6H, m, Ar); 6.11 (1H, d, J=6.9 Hz, CHPh); 4.98 (1H, br s, NH); 4.02 (2H, d, J=6.5 Hz, CH$_2$NH$_2$).

3-(Aminomethyl)benzoyl-D/L-phenylglycine benzothiazol-2-amide trifluoroacetate salt A solution of 3-(N-BOC-aminomethyl)benzoyl-D/L-phenyl-glycine benzothiazol-2-amide (156 mg, 0.3 mmol) in dichloromethane (3 mL) was stirred at room temperature and trifluoroacetic acid (2 mL) was added. Stirring was continued for a further hour and the solvents were removed under reduced pressure to afford a yellow oil which was triturated with diethyl ether to give the trifluoroacetate salt as a colourless solid (120 mg, 96%).

$^1$H NMR (d$_4$ methanol): 7.82–7.67 (3H, m, Ar); 7.56 (1H, d, J=7.2 Hz, Ar); 7.53–7.21 (8H, m, Ar); 7.19–7.09 (1H, m, CHPh); 3.89 (2H, s, CH$_2$NH$_2$).

HPLC (Luna 2, Gradient 1): rt=3.95 minutes.

LC/MS (Luna 2, Gradient 4): rt=1.88 minutes, 417 (MH)$^+$.

Examples 161–166 were prepared in a manner analogous to Example 160 except that the indicated amine was used in place of 2-aminobenzothiazole.

Example 161

3-(Aminomethyl)benzoyl-D/L-phenylglycine 5,6-dimethylbenzothiazol-2-amide trifluoroacetate salt From 2-amino-5,6-dimethylbenzothiazole.

$^1$H NMR (d$_4$ methanol): 7.80–7.63 ppm (2H, m, Ar); 7.47–7.07 (9H, m, Ar); 5.71 (1H, s, CHPh); 3.92 (2H, s, CH$_2$NH$_2$); 2.12 (6H, s, 2×CH$_3$).

HPLC (Luna 2, Gradient 1): rt=4.39 minutes.

LC/MS (Luna 2, Gradient 4): rt=2.10 minutes, 445 (MH)$^+$.

Example 162

3-(Aminomethyl)benzoyl-D/L-phenylglycine 6-methoxy benzothiazol-2-amide trifluoroacetate salt From 2-amino-6-methoxybenzothiazole.

$^1$H NMR (CDCl$_3$): 8.18 ppm (3H, br s, Ar and NH); 7.90 (1H, s, Ar); 7.79 (1H, s, Ar); 7.71 (1H, d, J=7.2 Hz, Ar); 7.63–7.28 (8H, m, Ar and NH); 7.24 (1H, s, Ar); 7.10 (1H, d, J=7.2 Hz, Ar); 5.72 (1H, d, J=6.5 Hz, CHPh); 4.09 (2H, s, CH$_2$NH$_2$); 3.88 (3H, s, OCH$_3$).

HPLC (Luna 2, Gradient 1): rt=4.26 minutes.

LC/MS (Luna 2, Gradient 4): rt=1.94 minutes, 447 (MH)$^+$.

Example 163

3-(Aminomethyl)benzoyl-D/L-phenylglycine 6-methylbenzothiazol-2-amide trifluoroacetate salt From 2-amino-6-methylbenzothiazole.

$^1$H NMR (d$_4$ methanol): 8.02–7.90 ppm (2H, m, Ar); 7.70–7.54 (6H, m, Ar); 7.48–7.37 (3H, m, Ar); 7.25 (1H, d, J=7.2 Hz, Ar); 5.92 (1H, s, CHPh); 4.19 (2H, s, CH$_2$NH$_2$); 2.46 (3H, s, CH$_3$).

HPLC (Luna 2, Gradient 1): rt=4.21 minutes.
LC/MS (Luna 2, Gradient 4): rt=2.26 minutes, 431 (MH)+.

Example 164

3-(Aminomethyl)benzoyl-D/L-phenylglycine 4-methoxybenzothiazol-2-amide trifluoroacetate salt From 2-amino-4-methoxybenzothiazole.
$^1$H NMR ($d_4$ methanol): 7.88 ppm (1H, d, J=7.2 Hz, Ar); 7.79 (1H, d, J=7.2 Hz, Ar); 7.64–7.14 (9H, m, Ar); 6.94 (1H, d, J=7.2 Hz, Ar); 5.89 (1H, s, CHPh); 4.03 (2H, s, C$\underline{H}_2$NH$_2$); 3.93 (3H, s, OCH$_3$).
HPLC (Luna 2, Gradient 1): rt=3.95 minutes.
LC/MS (Luna 2, Gradient 4): rt=1.88 minutes, 447 (MH)+.

Example 165

3-(Aminomethyl)benzoyl-D/L-phenylglycine 4-methylbenzothiazol-2-amide trifluoroacetate salt From 2-amino-4-methylbenzothiazole.
$^1$H NMR ($d_4$ methanol): 7.95 ppm (1H, s, Ar); 7.89 (1H, d, J=7.2 Hz, Ar); 7.69–7.33 (8H, m, Ar); 7.27–7.12 (2H, m, Ar); 5.91 (1. H, s, CHPh); 4.03 (2H, s, C$\underline{H}_2$NH$_2$); 2.60 (3H, s, CH$_3$).
HPLC (Luna 2, Gradient 1): rt=4.31 minutes.
LC/MS (Luna 2, Gradient 4): rt=2.18 minutes, 431 (MH)+.

Example 166

3-(Aminomethyl)benzoyl-D/L-phenylglycine 4-chlorobenzothiazol-2-amide trifluoroacetate salt From 2-amino-4-chlorobenzothiazole.
$^1$H NMR ($d_4$ methanol): 8.00–7.85 ppm (2H, m, Ar); 7.82–7.74 (1H, d, J=7.2 Hz, Ar); 7.67–7.35 (8H, m, Ar); 7.25 (1H, t, J=7.2 Hz, Ar); 5.89 (1H, s, CHPh); 4.10 (2H, s, C$\underline{H}_2$NH$_2$).
HPLC (Luna 2, Gradient 1): rt=4.29 minutes.
LC/MS (Luna 2, Gradient 4): rt=2.05 minutes, 451 (MH)+.

Example 167

3-(Aminomethyl)benzoyl-DL-phenylglycine tetrahydrobenzothiazol-2-amide

From 4,5,6,7-tetrahydrobenzothiazol-2-amine, the synthesis of which is described below.

4,5,6,7-Tetrahydro-1,3-benzothiazol-2-amine

A stirred mixture of 2-chlorocyclohexanone (200 mg, 1.5 mmol) and thiourea (114 mg, 1.5 mmol) in tetrahydrofuran (20 ml) was heated at reflux for 6 hours. The solution was concentrated under reduced pressure and the amine was purified by flash column chromatography using ethylacetate/hexane 1/1 as eluent to afford a colourless oil (169 mg, 74%).

$^1$H NMR (CDCl$_3$): 5.06 (2H, br s, NH$_2$); 2.40–2.23 (4H, m, 2×CH$_2$); 1.64–1.51 (4H, m, 2×CH$_2$).

3-(Aminomethyl)benzoyl-DL-phenylglycine tetrahydrobenzothiazol-2-amide $^1$H NMR ($d_4$ methanol): 8.01–7.92 (2H, m, Ar); 7.68 (1H, d, J=7.2 Hz, Ar); 7.61–7.51 (3H, m, Ar); 7.47–7.34 (3H, m, Ar); 5.90 (1H, s, CH); 4.20 (2H, s, C$\underline{H}_2$NH$_2$); 2.69 (2H, br s, CH$_2$); 2.60 (2H, br s, CH$_2$); 1.98 (4H, br s, 2×CH$_2$).
HPLC (Luna 2, Gradient 1): rt=3.55 minutes. LCMS (Luna 2, Gradient 4): rt=1.88 minutes, 421 (M+H)+.

The compounds exemplified hereinabove have been found to be inhibitors of tryptase by the method of Tapparelli et al., (1993) J. Biol. Chem., 268, 4734 to 4741.

The invention claimed is:
1. A tryptase inhibitor compound of formula (I)

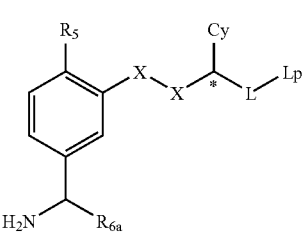

where:
R$_5$ represents amino, hydroxy, aminomethyl, hydroxymethyl or hydrogen;
R$_{6a}$ represents hydrogen or methyl;
X—X is selected from the group consisting of —CH=CH—, —CONR$_{1a}$—, —NH—CO—, —NR$_{1a}$—CH$_2$—, —CH$_2$—NR$_{1a}$—, —CH$_2$O—, —OCH$_2$—, —COO—, —OC=O— and —CH$_2$CH$_2$—;
R$_{1a}$ represents hydrogen, (1–6C)alkyl or phenyl(1–6C)alkyl;
L is CO or CONR$_{1d}$(CH$_2$)$_m$ in which m is 0 or 1 and R$_{1d}$ is hydrogen, (1–6C)alkyl or phenyl(1–6C)alkyl;
Cy is phenyl optionally substituted by R$_{3a}$ or R$_{3i}$X$_i$ in which X$_i$ is a bond, O, NH or CH$_2$ and R$_{3i}$ is phenyl optionally substituted by R$_{3a}$;
each R$_{3a}$ independently is hydrogen, hydroxyl, (1–6C) alkoxy, (1–6C)alkyl, (2–6C)alkenyl, (2–6C)alkynyl, (1–6C)alkanoyl, (1–6C) alkylaminoalkyl, hydroxy (1–6C)alkyl, carboxy, (1–6C) alkoxyalkyl, (1–6C) alkoxycarbonyl, (1–6C) alkylaminocarbonyl, amino (1–6C)alkyl CONH$_2$, CH$_2$CONH$_2$, aminoacetyl, (1–6C)alkanoylamino, (1–6C) alkoxycarbonylamino, amino, halo, cyano, nitro, thiol, 1–6C) alkylthio, (1–6C) alkylsulphonyl, (1–6C) alkylsulphenyl, imidazolyl, hydrazido, (1–6C) alkylimidazolyl, (1–6C) alkylsulphonamido, (1–6C) alkylaminosulphonyl, aminosulphonyl, (1–6C) haloalkoxy, or (1–6C) haloalkyl;
X$_i$ is a bond, O, NH or CH$_2$; and R$_{3i}$ is phenyl optionally substituted by R$_{3a}$; and
Lp is a heterocyclic group, or a combination of a heterocyclic group and one or more alkyl, alkenyl, carbocyclic or heterocyclic groups linked by a spiro linkage or a single or double bond or by C=O, O, OCO, COO, S, SO, SO$_2$, CONR$_{1e}$, NR$_{1e}$—CO— or NR$_{1e}$ linkage (where R$_{1e}$ is as defined for R$_{1a}$), optionally substituted by one or more oxo or R$_3$ groups in which R$_3$ is an amino acid residue, N-(1–6C)alkylaminocarbonyl, N,N-di(1–6C)alkylaminocarbonyl, N-(1–6C)alkylaminoalkanoyl, N-(1–6C)alkanoylamino(1–6C)alkanonyl, C-hydroxyamino(1–6C)alkanoyl, hydroxy(2–6C)alkanoylamino(1–6C)alkanoyl, di(1–6C)alkylaminosulfonyl, hydrogen, hydroxyl, (1–6C)alkoxy, (1–6C)alkanoyloxy, (1–6C) alkyl, (2–6C) alkenyl (2–6C) alkynyl, (3–6C)alkenyloxycarbonyl, (1–6C)alkanoyl, amino(1–6C)alkyl, amido (CONH$_2$), amino(1–6C)alkanoyl, aminocarbonyl(1–5C)alkanoyl, hydroxy (1–6C)alkyl, carboxy, hydroxy(1–6C)alkanoyl, (1–6C) alkoxy(1–6C)alkyl, (1–6C)alkoxycarbonyl(1–5C) alkyl, (1–6C)alkoxycarbonyl, (1–6C)alkanoylamino, amino, halo, cyano, nitro, thiol, (1–6C)alkylthio, (1–6C)alkylsulfonyl, (1–6C)alkylsulphenyl or hydrazido;

or a physiologically tolerable salt thereof.

2. A compound as claimed in claim 1, in which R$_5$ is amino or hydrogen.

3. A compound as claimed in claim 2, in which R$_5$ is hydrogen.

4. A compound as claimed in claim 1, in which R$_{6a}$ is hydrogen.

5. A compound as claimed in claim 1, in which X—X is CONH.

6. A compound as claimed in claim 1, in which the alpha carbon atom (*) has the conformation that would result from construction from a D-α-aminoacid NH$_2$—CH(Cy)—COOH where the NH$_2$ represents part of X—X.

7. A compound as claimed in claim 1, in which R$_{3a}$ is hydrogen; hydroxyl; methoxy; ethoxy; isopropoxy; methyl; ethyl; isopropyl; acetyl; propanoyl; isopropanoy; methylaminomethyl; dimethylaminomethyl; hydroxymethyl; carboxy; methoxymethyl; methoxycarbonyl; ethoxycarbonyl; methylaminocarbonyl; dimethylaminocarbonyl; aminomethyl; CONH$_2$; CH$_2$CONH$_2$; aminoacetyl; formylamino; acetylamino; methoxycarbonylamino; ethoxycarbonylamino; t-butoxycarbonylamino; amino; fluoro; chloro; cyano; nitro; thiol; methylthio; methylsulphonyl; ethylsulphonyl; methylsulphenyl; imidazol-4-yl; hydrazido; 2-methylimidazol-4-yl; methylsulphonylamido; ethylsulphonylamido; methylaminosulphonyl; ethylaminosulphonyl; aminosulphonyl; trifluoromethoxy or trifluoromethyl; and R$_{3i}$X$_i$ is phenyl, phenoxy, phenylamino or benzyl.

8. A compound as claimed in claim 7, in which Cy is phenyl, 4-aminophenyl, 3-hydroxyphenyl, 4-methylphenyl, 2,4-dimethylphenyl, 3,6-dimethylphenyl, 4-ethylphenyl, 4-isopropylphenyl, 4-hydroxphenyl, 3-aminomethylphenyl, 4-aminomethylphenyl, 4-(H$_2$NCO)phenyl, 4-hydroxymethylphenyl, 3-hydroxymethylphenyl, 2-hydroxymethylphenyl, 4-carboxyphenyl, 4-isopropoxyphenyl, 2-chlorophenyl, 4-phenylphenyl or 4-phenoxyphenyl.

9. A compound as claimed in claim 1, in which Cy represents an optionally R$_{3a}$ substituted phenyl group.

10. A compound as claimed in claim 9, in which R$_{3a}$ is selected from: hydrogen, hydroxyl, methoxy, ethoxy, methyl, ethyl, methylaminomethyl, dimethylaminomethyl, hydroxymethyl, methoxymethyl, methylaminocarbonyl, dimethylaminocarbonyl, aminomethyl, CONH$_2$, CH$_2$CONH$_2$, aminoacetyl, formylamino, acetylamino, methoxycarbonylamino, ethoxycarbonylamino, t-butoxycarbonylamino, amino, fluoro, chloro, cyano, nitro, thiol, methylthio, methylsulphenyl, imidazol-4-yl, hydrazido, 2-methylimidazol-4-yl, methylsulphonylamido, ethylsulphonylamido, methylaminosulphonyl, ethylaminosulphonyl, aminosulphonyl, trifluoromethoxy or trifluoromethyl.

11. A compound as claimed in claim 10, in which Cy is selected from the group consisting of phenyl, 4-aminophenyl, 4-hydroxyphenyl, 3-aminomethylphenyl, 4-aminomethylphenyl, 4-hydroxymethylphenyl, 3-hydroxymethylphenyl, 2-hydroxymethylphenyl and 4-phenylphenyl.

12. A compound as claimed in claim 1, in which L represents CO, CONH, CONCH$_3$ or CONHCH$_2$.

13. A compound as claimed in claim 12, in which L is CO, CONH or CONCH$_3$.

14. A compound as claimed in claim 1, in which R$_3$ is selected from the group consisting of N-acetylalaninoyl; serinoyl; threoninoyl; aspartoyl; glutamoyl; N-(1,3-dimethyl)butylamino-carbonyl; N-methyl-N-ethylaminocarbonyl; N-methylaminoacetyl; 2-N-acetylaminoacetyl; 2-N-acetylaminopropanoyl; 2-N-(2-methylpropanoyl) aminoacetyl; 2-amino-3hydroxypropanoyl; 2-amino-3-hydroxybutanoyl; 2-hydroxyacetylaminoacetyl; dimethylaminosulfonyl; hydrogen; hydroxyl; methoxy; acetoxy; methyl; ethyl; propyl; 2-propyl; 2,2-dimethylethyl; allyl; propynyl; allyloxycarbonyl; acetyl; propionyl; isobutyryl; aminomethyl; CONH$_2$; aminoacetyl; aminopropionyl; 2-aminopropionyl; aminocarbonylacetyl; hydroxymethyl; 1-hydroxyethyl; carboxy; 2-hydroxyacetyl; 2-hydroxypropanoyl; methoxymethyl; methoxycarbonylmethyl; methoxycarbonyl; ethoxycarbonyl; formylamino; acetylamino; amino; chloro; cyano; nitro; thiol; methylthio; methylsulphonyl; ethylsulfonyl; methylsulphenyl; and hydrazido.

15. A compound as claimed in claim 5, in which in which L represents CO and Lp represents

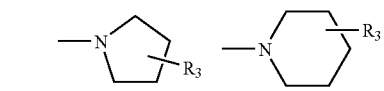

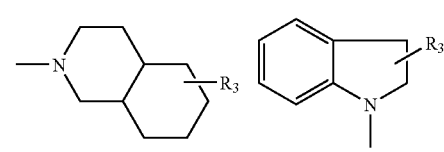

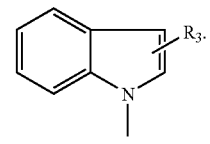

16. A compound as claimed in claim 15, in which R$_3$ represents hydrogen, hydroxyl or (1–6C)alkylaminocarbonyl.

17. A compound as claimed in claim 5, in which L represents CONH and Lp represents

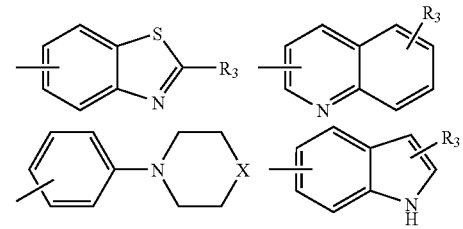

-continued

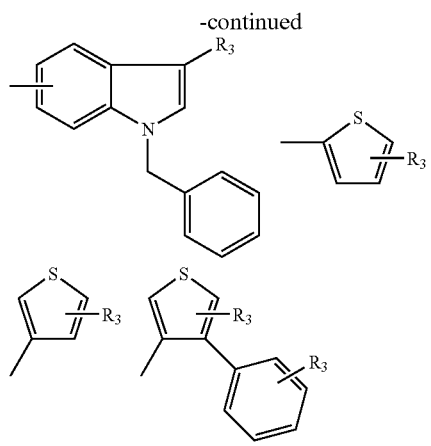

in which X is CH or N.

18. A compound as claimed in claim 17, in which each $R_3$ is selected independently from the group consisting of hydrogen, amino, hydroxy, (1–6C)alkyl, (1–6C)alkanoyl, (1–6C)alkanoyloxy, (1–5C)alkoxycarbonyl(1–6C)alkyl, amino(1–6C)alkyl and cyano.

19. A compound as claimed in claim 5, in L represents $CONR_{1d}$ and Lp represents

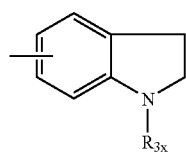

in which $R_{3x}$ represents $R_3$ or a group of formula $$—(X_{1y})_p\text{-}(G_1)\text{-}R_j$$

in which p is 0 or 1 ; $X_{1y}$ represents CO, COO, CONH or $SO_2$; $G_1$ represents (1–3C)alkanediyl, $CH_2OCH_2$ or, when p is 1, a bond; and $R_j$ represents a carbocyclic or heterocyclic group, optionally substituted by $R_3$.

20. A compound as claimed in claim 19, in which L represents CONH and $R_{3x}$, represents $R_3$ or a group of formula $$—(CO)_p\text{-}(G_1)\text{-}R_j$$

in which p is 0 or 1; $G_1$ represents (1–3C)alkanediyl or, when p is 1, a bond; and $R_j$ represents a carbocyclic or heterocyclic group, optionally substituted by $R_3$.

21. A compound as claimed in claim 19, in which Lp is selected from

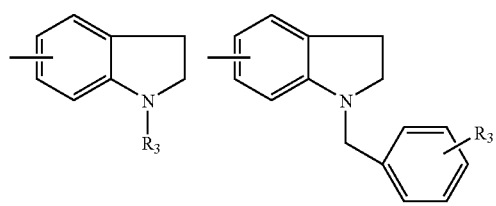

-continued

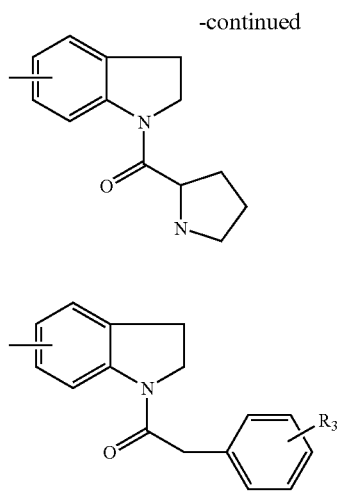

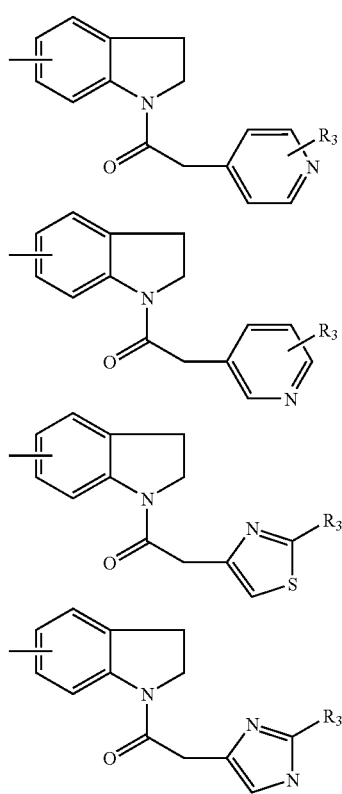

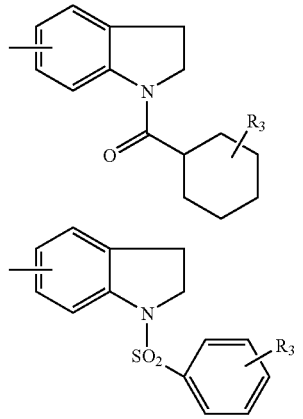

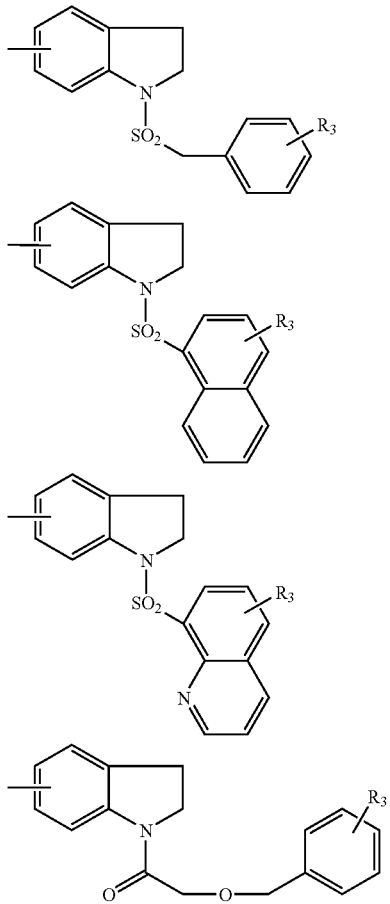

in which (i) when R₃ is a substituent on the 1-position of a 2,3-dihydroindolyl group, it represents an amino acid residue; (1–6C)alkylaminocarbonyl; N-(1–6C)alkylamino(1–6C)alkanoyl; N-alkanoylaminoalkanonyl; C-hydroxyamino(1–6C)alkanoyl; hydroxy(1–6C)alkanoylamino(1–6C)alkanoyl; di(1–6C)alkylaminosulfonyl; hydrogen; (1–6C)alkyl; (1–6C)alkanoyl; (1–6C)alkoxycarbonyl; (1–6C)acyloxymethoxycarbonyl; amino(1–6C)alkyl; amido (CONH₂); amino(1–6C)alkanoyl; aminocarbonyl(1–6C)alkanoyl; hydroxy(1–6C)alkyl; hydroxy(1–6C)alkanoyl; (1–6C)alkoxy(1–6C)alkyl; (1–6C)alkoxycarbonyl(1–6C)alkyl; (1–6C)alkoxycarbonyl; (1–6C)alkanoylamino; or (1–6C)alkylsulfonyl; and (ii) when R₃ is a substituent on a cyclohexyl, phenyl, naphthyl, thiazolyl, imidazolyl, pyridyl or quinolinyl group, it is hydrogen, hydroxy, amino, alkanoylamino, alkyl, aminoalkyl or alkanoylaminoalkyl.

22. A pharmaceutical composition, which comprises a compound as claimed in claim 1 together with at least one pharmaceutically acceptable carrier or excipient.

23. A method of treatment of the human or non-human animal body to combat a condition responsive to a tryptase inhibitor, which comprises administering to said body an effective amount of a compound as claimed in claim 1.

24. A method of treatment of the human or non-human animal body to combat a condition selected from asthma, allergic rhinitis, eczema, psoriasis, atopic dermatitis, urticaria, rheumatoid arthritis, conjunctivitis, inflammatory bowel disease, neurogenic inflammation, and atherosclerosis, which comprises administering to said body a compound of formula (I)

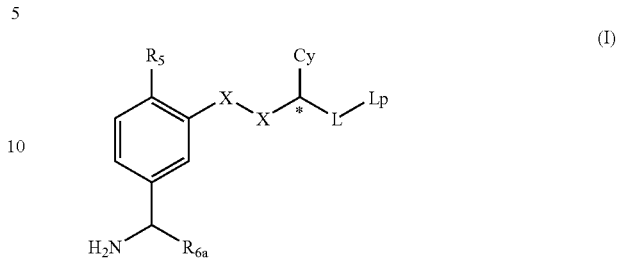

where:
R₅ represents amino, hydroxy, aminomethyl, hydroxymethyl or hydrogen;
R₆ₐ represents hydrogen or methyl;
X—X is selected from the group consisting of —CH=CH—, —CONR₁ₐ—, —NH—CO—, —NR₁ₐ—CH₂—, —CH₂—NR₁ₐ—, —CH₂O—, —OCH₂—, —COO—, —OC=O— and —CH₂CH₂—;
R₁ₐ represents hydrogen, (1–6C)alkyl or phenyl(1–6C)alkyl;
L is CO or CONR₁d(CH₂)ₘ in which m is 0 or 1 and R₁d is hydrogen, (1–6C)alkyl or phenyl(1–6C)alkyl;
Cy is phenyl optionally substituted by R₃ₐ or R₃ᵢXᵢ in which Xᵢ is a bond, O, NH or CH₂ and R₃ᵢ is phenyl optionally substituted by R₃ₐ;
each R₃ₐ independently is hydrogen, hydroxyl, (1–6C)alkoxy, (1–6C)alkyl, (2–6C)alkenyl, (2–6C)alkynyl, (1–6C)alkanoyl, (1–6C)alkylaminoalkyl, hydroxy(1–6C)alkyl, carboxy, (1–6C)alkoxyalkyl, (1–6C)alkoxycarbonyl, (1–6C) alkylaminocarbonyl, amino(1–6C)alkyl CONH₂, CH₂CONH₂, aminoacetyl, (1–6C)alkanoylamino, (1–6C)alkoxycarbonylamino, amino, halo, cyano, nitro, thiol, (1–6C)alkylthio, (1–6C) alkylsulphonyl, (1–6C)alkylsulphenyl, imidazolyl, hydrazido, (1–6C)alkylimidazolyl, (1–6C)alkylsulphonamido, (1–6C) alkylaminosulphonyl, aminosulphonyl, (1–6C) haloalkoxy, or (1–6C) haloalkyl; and
Lp is a heterocyclic group, or a combination of a heterocyclic group and one or more alkyl, alkenyl, carbocyclic or heterocyclic groups linked by a spiro linkage or a single or double bond or by C=O, O, OCO, COO, S, SO, SO₂, CONR₁ₑ, NR₁ₑ—CO— or NR₁ₑ linkage (where R₁ₑ is as defined for R₁ₐ), optionally substituted by one or more oxo or R₃ groups in which R₃ is an amino acid residue, N-(1–6C)alkylaminocarbonyl, N,N-di(1–6C)alkylaminocarbonyl, N-(1–6C)alkylaminoalkanoyl, N-(1–6C)alkanoylamino(1–6C)alkanonyl, C-hydroxyamino(1–6C)alkanoyl, hydroxy(2–6C)alkanoylamino(1–6C)alkanoyl, di(1–6C)alkylaminosulfonyl, hydrogen, hydroxyl, (1–6C)alkoxy, (1–6C)alkanoyloxy, (1–6C)alkyl, (2–6C)alkenyl (2–6C)alkynyl, (3–6C)alkenyloxycarbonyl, (1–6C)alkanoyl, amino(1–6C)alkyl, amido(CONH₂), amino(1–6C)alkanoyl, aminocarbonyl(1–5C)alkanoyl, hydroxy(1–6C)alkyl, carboxy, hydroxy(1–6C)alkanoyl, (1–6C)alkoxy(1–6C)alkyl, (1–6C)alkoxycarbonyl(1–5C)alkyl, (1–6C)alkoxycarbonyl, (1–6C)alkanoylamino, amino, halo, cyano, nitro, thiol, (1–6C)alkylthio, (1–6C)alkylsulfonyl, (1–6C)alkylsulphenyl or hydrazido;
or a physiologically tolerable salt thereof.

25. A method as claimed in claim 24, in which
$R_5$ is hydrogen;
$R_{6a}$ is hydrogen;
X—X is CONH; and
$R_3$ is selected from the group consisting of N-acetylalaninoyl; serinoyl; threoninoyl; aspartoyl; glutamoyl; N-(1,3-dimethyl)butylamino-carbonyl;
N-methyl-N-ethylaminocarbonyl; N-methylaminoacetyl; 2-N-acetylaminoacetyl; 2-N-acetylaminopropanoyl; 2-N-(2-methylpropanoyl)aminoacetyl; 2-amino-3-hydroxypropanoyl; 2-amino-3-hydroxybutanoyl; 2-hydroxyacetylaminoacetyl; dimethylaminosulfonyl; hydrogen; hydroxyl; methoxy; acetoxy; methyl; ethyl; propyl; 2-propyl; 2,2-dimethylethyl; allyl; propynyl; allyloxycarbonyl; acetyl; propionyl; isobutyryl; aminomethyl; $CONH_2$; aminoacetyl; aminopropionyl; 2-aminopropionyl; aminocarbonylacetyl; hydroxymethyl; 1-hydroxyethyl; carboxy; 2-hydroxyacetyl; 2-hydroxypropanoyl; methoxymethyl; methoxycarbonylmethyl; methoxycarbonyl; ethoxycarbonyl; formylamino; acetylamino; amino; chloro; cyano; nitro; thiol; methylthio; methylsulphonyl; ethylsulfonyl; methylsulphenyl; and hydrazido.

26. A method as claimed in claim 24, in which
Cy represents an optionally $R_{3a}$ substituted phenyl group; and
$R_{3a}$ is selected from: hydrogen, hydroxyl, methoxy, ethoxy, methyl, ethyl, methylaminomethyl, dimethylaminomethyl, hydroxymethyl, methoxymethyl, methylaminocarbonyl, dimethylaminocarbonyl, aminomethyl, $CONH_2$, $CH_2CONH_2$, aminoacetyl, formylamino, acetylamino, methoxycarbonylamino, ethoxycarbonylamino, t-butoxycarbonylamino, amino, fluoro, chloro, cyano, nitro, thiol, methylthio, methylsulphenyl, imidazol-4-yl, hydrazido, 2-methylimidazol-4-yl, methylsulphonylamido, ethylsulphonylamido, methylaminosulphonyl, ethylaminosulphonyl, aminosulphonyl, trifluoromethoxy or trifluoromethyl.

27. A method as claimed in claim 24, in which the condition is asthma.

* * * * *